(12) United States Patent
Xue

(10) Patent No.: US 7,700,624 B2
(45) Date of Patent: Apr. 20, 2010

(54) 3-AMINOCYCLOPENTANECRBOXAMIDES AS MODULATORS OF CHEMOKINE RECEPTORS

(75) Inventor: Chu-Biao Xue, Hockessin, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 11/613,330

(22) Filed: Dec. 20, 2006

(65) Prior Publication Data

US 2007/0149532 A1 Jun. 28, 2007

Related U.S. Application Data

(60) Provisional application No. 60/752,320, filed on Dec. 21, 2005, provisional application No. 60/752,477, filed on Dec. 21, 2005.

(51) Int. Cl.
  A61K 31/497    (2006.01)
  A61K 31/445    (2006.01)
  C07D 403/12    (2006.01)
  C07D 241/04    (2006.01)
  C07D 211/02    (2006.01)

(52) U.S. Cl. .................. 514/318; 514/253.01; 514/247; 514/254.11; 544/295; 544/358; 544/360; 546/195

(58) Field of Classification Search ................ 544/360, 544/295, 358; 514/247, 253.01, 318, 254.11; 546/195
See application file for complete search history.

(56) References Cited

U.S. PATENT DOCUMENTS

| 5,510,332 A | 4/1996 | Kogan et al. | |
|---|---|---|---|
| 2006/0004018 A1* | 1/2006 | Xue et al. ............ | 514/253.1 |
| 2006/0020133 A1* | 1/2006 | Xue et al. ............ | 544/295 |

FOREIGN PATENT DOCUMENTS

| WO | WO9601644 | 1/1996 |
|---|---|---|
| WO | WO9620216 | 7/1996 |
| WO | WO9620218 | 7/1996 |
| WO | WO9631206 | 10/1996 |
| WO | WO9515973 | 6/1998 |
| WO | WO9853814 | 12/1998 |
| WO | WO9853817 | 12/1998 |
| WO | WO9854207 | 12/1998 |
| WO | WO2005067502 | 7/2005 |

OTHER PUBLICATIONS

Wolf, Manfred E. "Burger's Medicinal Chemistry", 5th edition, part 1, pp. 975-977 (1995).*
Banker et al., "Modern Pharmaceutics", 3rd Ed. pp. 596 (1996).*
Springer, T.A., Adhesion receptors of the immune system; Nature 346:425-433 (1990).
Lawrence and Springer, Leukocytes Roll on a Selectin at Physiologic Flow Rates: Distinction from and Prerequisite for Adhesion through Integrins; Cell 65:859-873 (1991).
Butcher, E.C., Leukocyte-Endothelial Cell Recognition: Three (or More) Steps to Specificity and Diversity; Cell 67:1033-1036 (1991).
Luster, A.D., Chemokines-Chemotactic Cytokines That mediate Inflammation; New Eng. J Med., 338, 436-445 (1998).
Rollins, B.J. et al., Recombinant Human MCP-1/JE Induces Chemotaxis, Calcium Flux, and the Respiratory Burst in Human Monocytes; Blood, 90, 909-928 (1997).
Oppenheim, J.J. et al., Properties of the Novel Proinflammatory Supergene "IntercrIne" Cytokine Family; Annu. Rev. Immunol., 9:617-648 (1991).
Schall and Bacon, hemokines, leukocyte trafficking, and inflammation; Curr. Opin. Immunol., 6:865-873 (1994).
Bagiolini, M., et al. Interleukin-8 and Related Chemotactic Cytokines-CXC and CC Chemokines; Adv. Immunol., 55:97-179 (1994).
Valente, A.J., et al., Purification of a Monocyte Chemotactic Factor Secreted by Nonhuman Primate Vascular Cells in Culture; Biochemistry, 27, 4162 (1988).
Matsushima, K., et al., Purification and Characterization of a Novel Monocyte Chemotactic and Activating Factor Produced by a Human . . . ; J Exp. Med., 169, 1485 (1989).
Yoshimura, T., et al., Purification and Amino Acid Analysis of Two Human Monocyte Chemoattractants Produced by Phytohemagglutinin-Stimulated . . . ; J. Immunol., 142, 1956 (1989).
Rollins, B.J., et al., Cloning and expression of JE, a gene inducible by platelet-derived growth factor and whose product has . . . ; Proc. Natl. Acad. Sci. USA 85, 3738 (1988).
Rollins, B.J., et al., Recombinant Human MCP-1/JE Induces Chemotaxis, Calcium Flux and the Respiratory Burst in Human Monocytes; Blood, 78, 112 (1991).
Jiang, Y., et al., Monocyte Chemoattractant Protein-1 regulates adhesion Molecule Expression and Cytokine Production in Human Monocytes; J. Immunol., 148, 2423 (1992).
Vaddi, K., et al., Regulation of Monocyte Integrin Expression by β-Family Chemokines; J. Immunol., 153, 4721 (1994).

(Continued)

*Primary Examiner*—James O Wilson
*Assistant Examiner*—Ebenezer Sackey
(74) *Attorney, Agent, or Firm*—Connolly Bove Lodge & Hutz LLP

(57) ABSTRACT

The present invention is directed to compounds of Formula I:

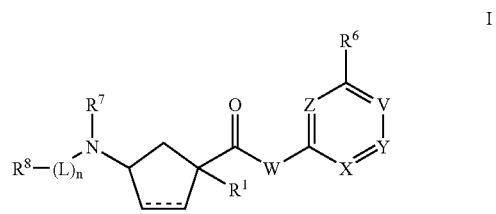

which are modulators of chemokine receptors. The compounds of the invention, and compositions thereof, are useful in the treatment of diseases related to chemokine receptor expression and/or activity.

38 Claims, No Drawings

OTHER PUBLICATIONS

Carr, M.W., et al., Monocyte chemoattractant protein 1 acts as a T-lymphocyte chemoattractant; Proc. Natl. Acad. Sci. USA, 91, 3652 (1994).

Loetscher, P., et al., Monocyte chemotactic proteins MCP-1, MCP-2 and MCP-3 are major attractants for human CD4+ and CD8+ T lymphocytes; FASEB J., 8, 1055 (1994).

Loetscher, P., et al., Activation of NK Cells by CC Chemokines Chemotaxis,Ca2+ MObilization, and Enzyme Release; CaJ. Immunol., 156, 322 (1996).

Allavena, P., et al., Induction of natural killer cell migration by monocyte chemotactic protein-1, -2 and 3*; Eur. J. Immunol., 24, 3233 (1994).

Alam, R., et al., Monocyte Chemotactic and Activating Factor is a Potent Histamine-releasing Factor for Basophils; J. Clin. Invest., 89, 723 (1992).

Bischoll, S.C., et al., Monocyte Chemotactic Protein 1 Is a Potent Activator of Human Basophils; J. Exp. Med., 175, 1271 (1992).

Kuna, P., et al., Monocyte Chemotactic and Activating Factor Is a Poetnnt Histamine-releasing Factor for Human Basophils; J. Exp. Med., 175, 489 (1992).

Hayes, I.M., et al., Human Vascular Smooth Muscle Cells Express Receptors for CC Chemokines; Arterioscler. Thromb. Vasc. Biol., 18, 397 (1998).

Takeya, M., et al., Detection of Monocyte Chemoattractant Protein-1 in Human Atherosclerotic Lesions by an Anti-monocyte Chemoattractant Protein.;Hum. Pathol., 24, 534 (1993).

Yia-Herttuala, S., et al., Expression of monocyte chemoattractant protein 1 in macrophage-rich areas of human and rabbit . . . ; Proc Natl. Acad. Sci. USA (88, 5252 (1991).

Nelken, N. A., Monocyte Chemoattractant Protein-1 in Human Atheromatous Plaques; J. Clin. Invest., 88, 1121 (1991).

Koch, A.E., et al., Enhanced Produced of Monocyte Chemoattractant Protein-1 in Rheumatoid Arthritis; J. Clin. Invest., 90, 772 (1992).

Akahoshi, T., et al., Expression of Monocyte Chemotactic and Activating Factor in Rheumatoid Arthritis; Arthritis Rheum., 36, 762 (1993).

Robinson, E.T., Clin. Exp. Immunol.; Chemokine expression in rheumatoid arthritis (RA): evidence of RANTES and macrophage inflammatory protein (MIP)-13β production.; 101, 398 No date provided.

Noris, M., et al., Monocyte Chemoattractant Protein-1 is Excreted in Excessive Amounts in the Urine of Patients with Lupus Nephritis; Lab. Invest., 73, 804 (1995).

Grimm, M. C., et al., Enhanced expression and production of monocyte chemoattractant protein-1 in inflammatory bowel disease mucosa; J. Leukoc. Biol., 59, 8047 (1996).

Reinecker, H.C., et al., Monocyte-Chemoattractant Protein 1 Gene Expression in Intestinal Epithelial Cells and Inflammatory Bowel Disease . . . ; Gastroenterology, 108, 40 (1995).

Seino, Y., et al., Expression of Leukocyte Chemotactic Cytokines in Myocardial Tissue; Chemokine, 7, 301 (1995).

Jolicoeur, C., et al., Increased Expression of Monocyte Chemotactic Protein-1 in the Endometrium of Women with Endometriosis; Am. J. Pathol., 152, 125 (1998).

Zeyneloglu, H. B., et al., The role of monocyte chemotactic protein-1 in intraperitoneal adhesion formation; Human Reproduction 13, 1194 (1998).

Aukrust, P., et al., Elevated Circulating Levels of C-C Chemokines in Patients With Congestive Heart Failure; Circulation, 97, 1136 (1998).

Marra, F., et al., Increased Expression of Monocyte Chemotactic Protein-1 during Active Hepatic Fibrogenesis; Am. J. Pathol., 152, 423 (1998).

Lahrtz, F., et al., Interleukin-16, produced by synovial fibroblasts, mediates chemoattraction for CD4+ T Lymphocytes in rheumatoid arthritis;Eur. J. Immunol., 27, 2484 (1997).

Wong, M., et al., Evidence for RANTES, Monocyte Chemotactic Protein-1, and Macrophage Inflammatory Protein-1β Expression in Kawasaki Disease; J. Rheumatol., 24, 1179 (1997).

Salkowski, C.A., et al., Pulmonary and Hepatic Gene Expression following Cecal Ligation and Puncture: Monophosphoryl Lipid A Prophylaxis . . . ; Infect. Immun., 66, 3569 (1998).

Schimmer, R.C. et al., Streptococcal Cell Wall-Induced Arthritis: Requirements for IL-4, IL-10, IFN-y, and Monocyte Chemoattractant Protein-1; J. Immunol., 160, 1466 (1998).

Schrier, D.J.,Role of chemokines and cytokines in a reactivation model of arthritis in rats induced by injection with streptococcal cell walls;J. Leukoc. Biol., 63, 359 (1998).

Ogata, H., The Role of Monocyte Chemoattractant Protein-1 (MCP-1) in the Pathogenesis of Collagen-Induced Arthritis in Rats; J. Pathol., 182, 106 (1997).

Karpus, W.J., et al., MIP-1α and MCP-1 differentially regulate acute and relapsing autoimmune encephalomyelitis as well as Th1/Th2 . . . ; J. Leukoc. Biol., 62, 681 (1997).

Lloyd, C.M., et al., RANTES and Monocyte Chemoattractant Protein-1 (MCP-1) Play an Important Role Int he Inflammatory Phase of Crescentic . . . ; J. Exp. Med., 185, 1371 (1997).

Wada, T., et al., Intervention of crescentic glomerulonephritis by antibodies to monocyte chemotactic and activating factor (MCAF/MCP-1); FASEBJ., 10,1418 (1996).

Gonazlo, J.-A., et al., The Coordinated Action of CC Chemokines in the Lung Orchestrates Allergic Inflammation and Airway Hyperresponsiveness; J. Exp. Med., 188, 157 (1998).

Lukacs, N. W., Differential Recruitment of Leukocyte Populations and Alteration of Airway Hyperreactivity by C-C Family Chemokines in Allergic . . . ;J. Immunol., 158, 4398 (1997).

Guzman, L.A., et al., Monocyte Chemotactic Protein Antibody Inhibits Restenosts in the Rabbit Atherosclerotic Model; Circulation, 88 No. 4, Pt. 2(suppl.),Ab.#1988;1-371 (1993).

Rand, M.L., et al., Inhibition of T Cell Recruitment and Cutaneous Delayed-Type Hypersensitivity-Induced Inflammation with Antibodies to . . . ;Am. J. Pathol., 148, 855 (1996).

Kimura, H., et al., Lab. Invest., Alleviation of Monocrotaline-Induced Pulmonary Hypertension by Antibodies to Monocyte Chemotactic and Activating Factor/ . . . ; 78, 571 (1998) .

Zeyneloglu, H.B., et al., The effect of monocyte chemotactic protein 1 in intraperitoneal adhesion formation in a mouse model; Am. J. Obstet. Gynecol., 179, 438 (1998).

Gong, J-H., J. Exp., 4ed., An Antagonist of Monocyte Chemoattractant Protein 1 (MCP-1) Inhibits Arthritis in the MRL Ipr Mouse Model; 186, 131 (1997).

Lu, B., et al., Abnormalities in Monocyte Recruitment and Cytokine Expression in Monocyte Chemoattractant Protein 1-deficient Mice . . . ; J. Exp. Med., 187, 601 (1998).

Gu, L., et al., Absence of Monocyte Chemoattractant Protein-1 Reduces Atherosclerosis in Low Density Lipoprotein Receptor-Deficient Mice; Moll. Cell, 2, 275 (1998).

DeBoer, W.I., Cytokines and Therapy in COPD*: A Promising Combination?; Chest, 121, 209S-318S (2002).

Rovin, B.H., et al., Am. J. Kidney. Dis., Chemotactic Factors and Renal Inflammation; 31, 1065 (1998).

Lloyd, C., et al., The role of chemokines in tissue Inflammation and autoimmunity in renal diseases; Curr. Opin. Nephrol. Hypertens., 7, 281 (1998).

Conti, P., et al, Will MCP-1 and RANTES Take Center Stage in Inflammatory Diseases Including Asthma?; Allergy and Asthma Proc., 19, 121 (1998).

Ransohoff, R.M., et al., Do chemokines mediate leukocyte recruitment in post-traumatic CNS inflammation?; Trends Neurosci, 21, 154 (1998).

Dragic et al., A binding pocket for a small molecule inhibitor of HIV-1 entry within the transmembrane helices of CCR5; Proc. Natl. Acad. Sci. USA 97(10), 5639 (2000).

De Clerq et al., Antivir. Chem. Chemother.; Inhibition of HIV Infection by CXCR4 and CCR5 Chemokine Receptor Antagonists; 12, Suppl. 1, 19 (2001).

Strizki et al., Proc. Natl. Acad. Sci. USA 98(22), 12718 (2001) or Tremblay et al., Antimicrobial Agents and Chemotherapy, 46(5), 1336 (2002).

Billick et al., The Differential Sensitivity of Human and Rhesus Macaque CCR5 to Small-Molecule Inhibitors of Human Immunodeficiency Virus Type.;J. Virol., 78(8), 4134 (2004).

Remington's Pharmaceutical Sciences, 17th ed., Mack Publishing Company, Easton, Pa., 1985 p. 1418 and Journal of Pharmaceutical Science, 66, 2 (1977).

T. Higuchi and V. Stella, "Pro-drugs as Novel Delivery Systems," vol. 14 of the A.C.S. Symposium Series . . . No date provided.

. . . and in Bioreversible Carriers in Drug Design, ed. Edward B. Roche, American Pharmaceutical Association and Pergamon Press, 1987.

T.W. Greene and P.G.M. WUTS, Protective Groups in Organic Synthesis, 3rd. Ed., Wiley & Sons, Inc., New York (1999).

Boring, L., el al., Impaired Monocyte Migration and Reduced Type 1 (Th1) Cytokine Responses in C-C Chemokine Receptor 2 Knockout Mice; J. Clin. Invest., 100, 2552 (1997).

Kurihara, T., et al., Defects in macrophage Recruitment and host Defense in Mice Lacking the CCR2 Chemokine Receptor; J. Exp. Med., 186, 1757 (1997).

Gao, J.-L., et al., Impaired Host Defense, Hematopoiesis, Granulomatous Inflammation and Type 1-Type 2 Cytokine Balance in Mice Lacking CC . . . ; J. Exp. Med., 185, 1959 (1997).

Gerard, C., et al., Targeted Disruption of the β-Chemokine Receptor CCR1 Protects against Pancreatitis-associated Lung Injury; J. Clin. Invest., 100, 2022 (1997).

Boring, L., et al., Decreased lesion formation in CCR2-/- mice reveals a role for chemokines in the initiation of atherosclerosis; Nature, 394, 894 (1998).

Kuziel, W.A., et al.,Severe reduction in leukocyte adhesion and monocyte extravasationin mice deficient in CC chemokine receptor.;Proc. Natl. Acad. Sci., USA, 94, 12053 (1997).

Kurihara, T., et al., Defects in macrophage Recruitment and host Defense in Mice Lacking the CCR2 Chemokine Receptor; J. Exp. Med., 186, 1757 (1997).

Boring, L., et al., Impaired Monocyte Migration and Reduced Type 1 (Th1) Cytokine Responses in C-C Chemokine Receptor 2 Knockout Mice; J. Clin. Invest., 100, 2552 (1997).

Starr-Spires et al., Clin. Lab. Med., HIV-1 entry and entry inhibitors as therapeutic agents; 22(3), 681 (2002).

* cited by examiner

3-AMINOCYCLOPENTANECRBOXAMIDES AS MODULATORS OF CHEMOKINE RECEPTORS

CROSS-REFERENCE TO RELATED PATENTS AND PATENT APPLICATIONS

This application claims the benefit of U.S. Provisional Patent Application Ser. No. 60/752,320 filed Dec. 21, 2005 and U.S. Provisional Patent Application Ser. No. 60/752,477 filed Dec. 21, 2005, all of which are incorporated by reference herein in their entireties.

FIELD OF THE INVENTION

The present invention relates to compounds that modulate the activity of chemokine receptors such as CCR2 and CCR5. In some embodiments, the compounds modulate both CCR2 and CCR5. The compounds can be used, for example, to treat diseases associated with chemokine receptor expression or activity.

BACKGROUND OF THE INVENTION

The migration and transport of leukocytes from blood vessels into diseased tissues is involved in the initiation of normal disease-fighting inflammatory responses. The process, also known as leukocyte recruitment, is also related to the onset and progression of life-threatening inflammatory, as well as debilitating autoimmune diseases. The resulting pathology of these diseases derives from the attack of the body's immune system defenses on normal tissues. Accordingly, preventing and blocking leukocyte recruitment to target tissues in inflammatory, autoimmune disease and cancer would be a highly effective approach to therapeutic intervention.

The different classes of leukocyte cells that are involved in cellular immune responses include monocytes, lymphocytes, neutrophils, eosinophils and basophils. In most cases, lymphocytes are the leukocyte class that initiates, coordinates, and maintains chronic inflammatory responses, and blockage of these cells from entering inflammatory sites is desirable. Lymphocytes attract monocytes to the tissue sites, which, collectively with lymphocytes, are responsible for most of the actual tissue damage that occurs in inflammatory disease. Infiltration of the lymphocytes and/or monocytes is known to lead to a wide range of chronic, autoimmune diseases, and also organ transplant rejection. These diseases include, but are not limited to, rheumatoid arthritis, chronic contact dermatitis, inflammatory bowel disease, lupus, systemic lupus erythematosus, multiple sclerosis, atherosclerosis, psoriasis, sarcoidosis, idiopathic pulmonary fibrosis, dermatomyositis, skin pemphigoid and related diseases, (e.g., *Pemphigus vulgaris, P. foliacious, P. erythematosis*), glomerulonephritides, vasculitides, hepatitis, diabetes, allograft rejection, and graft-versus-host disease.

The process by which leukocytes leave the bloodstream, accumulate at inflammatory sites, and start disease is believed to have at least three steps which have been described as (1) rolling, (2) activation/firm adhesion and (3) transendothelial migration [Springer, T. A., Nature 346:425-433 (1990); Lawrence and Springer, Cell 65:859-873 (1991); Butcher, E. C., Cell 67:1033-1036 (1991)]. The second step is mediated at the molecular level by chemoattractant receptors. Chemoattractant receptors on the surface of leukocytes then bind chemoattractant chemokines which are secreted by cells at the site of damage or infection. Receptor binding activates leukocytes, increases the adhesiveness of the adhesion molecules that mediate transendothelial migration, and promotes directed migration of the cells toward the source of the chemoattractant chemokine.

Chemotactic chemokines (leukocyte chemoattractant/activating factors) also known as chemokines, also known as intercrines and SIS chemokines, are a group of inflammatory/immunomodulatory polypeptide factors of molecular weight 6-15 kDa that are released by a wide variety of cells such as macrophages, monocytes, eosinophils, neutrophils, fibroblasts, vascular endothelial cells, smooth muscle cells, and mast cells, at inflammatory sites (reviewed in Luster, New Eng. J Med., 338, 436-445 (1998) and Rollins, Blood, 90, 909-928 (1997)). Also, chemokines have been described in Oppenheim, J. J. et al., Annu. Rev. Immunol., 9:617-648 (1991); Schall and Bacon, Curr. Opin. Immunol., 6:865-873 (1994); Baggiolini, M., et al., and Adv. Immunol., 55:97-179 (1994). Chemokines have the ability to stimulate directed cell migration, a process known as chemotaxis. Each chemokine contains four cysteine residues (C) and two internal disulfide bonds. Chemokines can be grouped into two subfamilies, based on whether the two amino terminal cysteine residues are immediately adjacent (CC family) or separated by one amino acid (CXC family). These differences correlate with the organization of the two subfamilies into separate gene clusters. Within each gene cluster, the chemokines typically show sequence similarities between 25 to 60%. The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

MCP-1 (also known as MCAF (abbreviation for macrophage chemotactic and activating factor) or JE) is a CC chemokine produced by monocytes/macrophages, smooth muscle cells, fibroblasts, and vascular endothelial cells and causes cell migration and cell adhesion of monocytes (see for example Valente, A. J., et al., Biochemistry, 1988, 27, 4162; Matsushima, K., et al., J. Exp. Med., 1989, 169, 1485; Yoshimura, T., et al., J. Immunol., 1989, 142, 1956; Rollins, B. J., et al., Proc. Natl. Acad. Sci. USA, 1988, 85, 3738; Rollins, B. J., et al., Blood, 1991, 78, 1112; Jiang, Y., et al., J. Immunol., 1992, 148, 2423; Vaddi, K., et al., J. Immunol., 1994, 153, 4721), memory T lymphocytes (see for example Carr, M. W., et al., Proc. Natl. Acad. Sci. USA, 1994, 91, 3652), T lymphocytes (see for example Loetscher, P., et al., FASEB J., 1994, 8, 1055) and natural killer cells (see for example Loetscher, P., et al., J. Immunol., 1996, 156, 322; Allavena, P., et al., Eur. J. Immunol., 1994, 24, 3233), as well as mediating histamine release by basophils (see for example Alam, R., et al., J. Clin. Invest., 1992, 89, 723; Bischoff, S. C., et al., J. Exp. Med., 1992, 175, 1271; Kuna, P., et al., J. Exp. Med., 1992, 175, 489). In addition, high expression of MCP-1 has been reported in diseases where accumulation of monocyte/macrophage and/or T cells is thought to be important in the initiation or progression of diseases, such as atherosclerosis (see for example Hayes, I. M., et al., Arterioscler. Thromb. Vasc. Biol., 1998, 18, 397; Takeya, M. et al., Hum. Pathol., 1993, 24, 534; Yla-Herttuala, S., et al., Proc. Natl. Acad. Sci. USA, 1991, 88, 5252; Nelken, N. A., J. Clin. Invest., 1991, 88, 1121), rheumatoid arthritis (see for example Koch, A. E., et al., J. Clin. Invest., 1992, 90, 772; Akahoshi, T., et al., Arthritis Rheum., 1993, 36, 762; Robinson, E., et al., Clin. Exp. Immunol., 101, 398), nephritis (see for example Noris, M., et al., Lab. Invest., 1995, 73, 804; Wada, T., et al., Kidney Int., 1996, 49, 761; Gesualdo, L., et al., Kidney Int., 1997, 51, 155), nephropathy (see for example Saitoh, A., et al., J. Clin. Lab. Anal., 1998, 12, 1; Yokoyama, H., et al., J. Leukoc. Biol., 1998, 63, 493), pulmonary fibrosis, pulmonary sarcoidosis (see for example Sugiyama, Y., et al., Internal Medicine, 1997, 36, 856), asthma (see for example Karina, M., et al., J. Invest. Allergol. Clin. Immunol., 1997, 7, 254; Stephene, T. H., Am. J. Respir. Crit. Care Med., 1997, 156, 1377; Sousa, A. R., et al., Am. J. Respir. Cell Mol. Biol., 1994, 10, 142), multiple sclerosis (see for example McManus, C., et al., J. Neuroimmunol., 1998, 86, 20), psoriasis (see for example Gillitzer, R., et al., J. Invest. Dermatol., 1993, 101, 127), inflammatory bowel disease (see for example Grimm, M. C., et al., J. Leukoc. Biol., 1996, 59, 804; Reinecker, H. C., et al., Gastroenterology, 1995, 106, 40), myocarditis (see for example Seino, Y., et al., Chemokine, 1995, 7, 301), endometriosis (see for example Jolicoeur, C., et al., Am. J. Pathol., 1998, 152, 125), intraperitoneal adhesion (see for example Zeyneloglu, H. B., et al., Human Reproduction, 1998, 13, 1194), congestive heart failure (see for example Aurust, P., et al., Circulation, 1998, 97, 1136), chronic liver disease (see for example Marra, F., et al., Am. J. Pathol., 1998, 152, 423), viral meningitis (see for example Lahrtz, F., et al., Eur. J. Immunol., 1997, 27, 2484), Kawasaki disease (see for example Wong, M.; et al., J. Rheumatol., 1997, 24, 1179) and sepsis (see for example Salkowski, C. A.; et al., Infect. Immun., 1998, 66, 3569). Furthermore, anti-MCP-1 antibody has been reported to show an inhibitory effect or a therapeutic effect in animal models of rheumatoid arthritis (see for example Schimmer, R. C., et al., J. Immunol., 1998, 160, 1466; Schrier, D. J., J. Leukoc. Biol., 1998, 63, 359; Ogata, H., et al., J. Pathol., 1997, 182, 106), multiple sclerosis (see for example Karpus, W. J., et al., J. Leukoc. Biol., 1997, 62, 681), nephritis (see for example Lloyd, C. M., et al., J. Exp. Med., 1997, 185, 1371; Wada, T., et al., FASEB J., 1996, 10, 1418), asthma (see for example Gonzalo, J.-A., et al., J. Exp. Med., 1998, 188, 157; Lukacs, N. W., J. Immunol., 1997, 158, 4398), atherosclerosis (see for example Guzman, L. A., et al., Circulation, 1993, 88 (suppl.), I-371), delayed type hypersensitivity (see for example Rand, M. L., et al., Am. J. Pathol., 1996, 148, 855), pulmonary hypertension (see for example Kimura, H., et al., Lab. Invest., 1998, 78, 571), and intraperitoneal adhesion (see for example Zeyneloglu, H. B., et al., Am. J. Obstet. Gynecol., 1998, 179, 438). A peptide antagonist of MCP-1, MCP-1 (9-76), has been also reported to inhibit arthritis in the mouse model (see Gong, J.-H., J. Exp., 4ed., 1997, 186, 131), as well as studies in MCP-1-deficient mice have shown that MCP-1 is essential for monocyte recruitment in vivo (see Lu, B., et al., J. Exp. Med., 1998, 187, 601; Gu, L., et al., Moll. Cell, 1998, 2, 275).

Chronic obstructive pulmonary disease (COPD) ranks among the most common causes of death in Western societies. It is defined by a progressive decline in lung function, only partly reversible by bronchodilator drugs. COPD is characterized by chronic inflammation in the airways or alveoli that differs from that seen in asthma, involving increased numbers of neutrophils, macrophages, CD8+ T cells, and/or mast cells in the airway walls, alveolar compartments, and vascular smooth muscle. Cytokines associated with COPD are believed to include tumor necrosis factor (TNF)-alpha, interferon (IFN)-gamma, interleukin (IL)-1 beta, IL-6, IL-8 and MCP-1. CCR2 is known to be a receptor for MCP-1, and recent data support a role for MCP-1 and CCR2 in airway remodeling and inflammation directly or via macrophages. Thus, antagonists of CCR2 are an attractive approach to therapeutic treatment of COPD (De Boer, W. I., Chest, 2002, 121, 209S-218S).

The literature indicates that chemokines such as MCP-1 and MIP-1α attract monocytes and lymphocytes to disease sites and mediate their activation and thus are thought to be intimately involved in the initiation, progression and maintenance of diseases deeply involving monocytes and lymphocytes, such as atherosclerosis, restenosis, rheumatoid arthritis, psoriasis, asthma, ulcerative colitis, nephritis (nephropathy), multiple sclerosis, pulmonary fibrosis, myocarditis, hepatitis, pancreatitis, sarcoidosis, Crohn's disease, endometriosis, congestive heart failure, viral meningitis, cerebral infarction, neuropathy, Kawasaki disease, and sepsis (see for example Rovin, B. H., et al., Am. J. Kidney. Dis., 1998, 31, 1065; Lloyd, C., et al., Curr. Opin. Nephrol. Hypertens., 1998, 7, 281; Conti, P., et al., Allergy and Asthma Proc., 1998, 19, 121; Ransohoff, R. M., et al., Trends Neurosci., 1998, 21, 154; MacDermott, R. P., et al., Inflammatory Bowel Diseases, 1998, 4, 54).

The chemokines bind to specific cell-surface receptors belonging to the family of G-protein-coupled seven-transmembrane-domain proteins (reviewed in Horuk, Trends Pharm. Sci., 15, 159-165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration.

Genes encoding receptors of specific chemokines have been cloned, and it is known that these receptors are G protein-coupled seven-transmembrane receptors present on various leukocyte populations. So far, at least five CXC chemokine receptors (CXCR1-CXCR5) and eight CC chemokine receptors (CCR1-CCR10) have been identified. For example IL-8 is a ligand for CXCR1 and CXCR2, MIP-1α is a ligand for CCR1 and CCR5, and MCP-1 is a ligand for CCR2A and CCR2B (for reference, see for example, Holmes, W. E., et al., Science 1991, 253, 1278-1280; Murphy P. M., et al., Science, 253, 1280-1283; Neote, K. et al, Cell, 1993, 72, 415-425; Charo, I. F., et al., Proc. Natl. Acad. Sci. USA, 1994, 91, 2752-2756; Yamagami, S., et al., Biochem. Biophys. Res. Commun., 1994, 202, 1156-1162; Combadier, C., et al., The Journal of Biological Chemistry, 1995, 270, 16491-16494, Power, C. A., et al., J. Biol. Chem., 1995, 270, 19495-19500; Samson, M., et al., Biochemistry, 1996, 35, 3362-3367; Murphy, P. M., Annual Review of Immunology, 1994, 12, 592-633). It has been reported that lung inflammation and granuroma formation are suppressed in CCR1-deficient mice (see Gao, J.-L., et al., J. Exp. Med., 1997, 185, 1959; Gerard, C., et al., J. Clin. Invest., 1997, 100, 2022), and that recruitment of macrophages and formation of atherosclerotic lesion decreased in CCR2-deficient mice (see Boring, L., et al., Nature, 1998, 394, 894; Kuziel, W. A., et al., Proc. Natl. Acad. Sci., USA, 1997, 94, 12053; Kurihara, T., et al., J. Exp. Med., 1997, 186, 1757; Boring, L., et al., J. Clin. Invest., 1997, 100, 2552).

Chemokine receptors are also known as coreceptors for viral entry leading to viral infection such as, for example, HIV infection. Reverse transcription and protein processing are the classic steps of the viral life cycle which antiretroviral therapeutic agents are designed to block. Although many new drugs that are believed to block viral entry hold promise, there is currently no agent to which HIV-1 has not been able to acquire resistance. Multiple rounds of viral replication are required to generate the genetic diversity that forms the basis of resistance. Combination therapy in which replication is maximally suppressed remains a cornerstone of treatment with entry inhibitors, as with other agents. The targeting of multiple steps within the viral entry process is believed to have the potential for synergy (Starr-Spires et al., *Clin. Lab. Med.*, 2002, 22(3), 681).

HIV-1 entry into CD4(+) cells requires the sequential interactions of the viral envelope glycoproteins with CD4 and a coreceptor such as the chemokine receptors CCR5 and CXCR4. A plausible approach to blocking this process is to use small molecule antagonists of coreceptor function. The TAK-779 molecule is one such antagonist of CCR5 that acts to prevent HIV-1 infection. TAK-779 inhibits HIV-1 replication at the membrane fusion stage by blocking the interaction of the viral surface glycoprotein gp120 with CCR5. The binding site for TAK-779 on CCR5 is located near the extracellular surface of the receptor, within a cavity formed between transmembrane helices 1, 2, 3, and 7 (Dragic et al., *Proc. Natl. Acad. Sci. USA*, 2000, 97(10), 5639).

The chemokine receptors CXCR4 and CCR5 are believed to be used as co-receptors by the T cell-tropic (X4) and macrophage-tropic (R5) HIV-1 strains, respectively, for entering their host cells. Propagation of R5 strains of HIV-1 on CD4 lymphocytes and macrophages requires expression of the CCR5 coreceptor on the cell surface. Individuals lacking CCR5 (CCR5 Delta 32 homozygous genotype) are phenotypically normal and resistant to infection with HIV-1. Viral entry can be inhibited by the natural ligands for CXCR4 (the CXC chemokine SDF-1) and CCR5 (the CC chemokines RANTES, MIP-1alpha and MIP-1beta). The first non-peptidic compound that interacts with CCR5, and not with CXCR4, is a quaternary ammonium derivative, called TAK-779, which also has potent but variable anti-HIV activity (De Clercq et al., *Antivir. Chem. Chemother*. 2001, 12 Suppl. 1, 19.

SCH-C (SCH 351125) is another small molecule inhibitor of HIV-1 entry via the CCR5 coreceptor. SCH-C, an oxime-piperidine compound, is a specific CCR5 antagonist as determined in multiple receptor binding and signal transduction assays. This compound specifically inhibits HIV-1 infection mediated by CCR5 in U-87 astroglioma cells but has no effect on infection of CXCR4-expressing cells. (Strizki et al, *Proc. Natl. Acad. Sci. USA*, 2001, 98(22), 12718 or Tremblay et al., *Antimicrobial Agents and Chemotherapy*, 2002, 46(5), 1336).

AD101, chemically related to SCH-C, also inhibits the entry of human immunodeficiency virus type 1 (HIV-1) via human CCR5. It has been found that AD101 inhibits HIV-1 entry via rhesus macaque CCR5 while SCH-C does not. Among the eight residues that differ between the human and macaque versions of the coreceptor, only one, methionine-198, accounts for the insensitivity of macaque CCR5 to inhibition by SCH-C. Position 198 is in CCR5 transmembrane (TM) helix 5 and is not located within the previously defined binding site for AD101 and SCH-C, which involves residues in TM helices 1, 2, 3, and 7. Based on studies of amino acid substitutions in CCR5, it has been suggested that the region of CCR5 near residue 198 can influence the conformational state of this receptor. (Billick et al., 2004, *J. Virol.*, 78(8), 4134).

The identification of compounds that modulate the activity of chemokine receptors represents a desirable drug design approach for the needed development of pharmacological agents for the treatment of diseases associated with chemokine receptor activity. The compounds of the present invention help fulfill these and other needs.

SUMMARY OF THE INVENTION

The present invention provides compounds of Formula I:

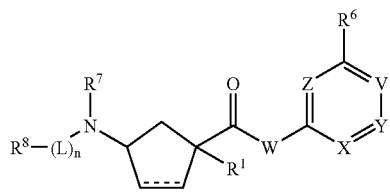

or pharmaceutically acceptable salts or prodrugs thereof, wherein constituent members are provided herein.

The present invention further provides compositions comprising a compound of Formula I and a pharmaceutically acceptable carrier.

The present invention further provides methods of modulating activity of a chemokine receptor comprising contacting the chemokine receptor with a compound of Formula I.

The present invention further provides methods of treating a disease associated with expression or activity of a chemokine receptor in a patient comprising administering to the patient a therapeutically effective amount of a compound of Formula I.

The present invention further provides methods of treating HIV infection in a patient comprising administering to said patient a therapeutically effective amount of a compound of Formula I.

The present invention further provides a compound of the invention for use in therapy.

The present invention further provides a compound of the invention for the preparation of a medicament for use in therapy.

DETAILED DESCRIPTION

Compounds

The present invention provides, inter alia, compounds of Formula I:

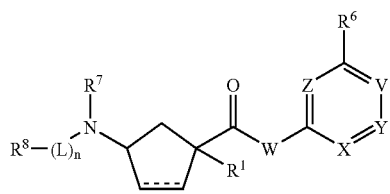

or pharmaceutically acceptable salts or prodrugs thereof, wherein:
  a dashed line indicates an optional bond;
  W is:

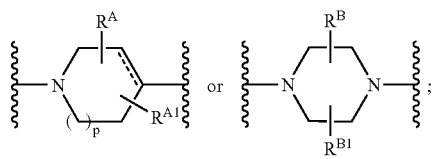

V is N, NO or CR$^5$;

X is N, NO or CR$^2$;

Y is N, NO or CR$^3$;

Z is N, NO or CR$^4$; wherein no more than one of V, X, Y and Z is NO;

L is C$_{1-4}$ alkylenyl, C$_{2-4}$ alkenylenyl, C$_{2-4}$ alkynylenyl, C(O), C(O)NR$^9$, S(O), S(O)NR$^9$, S(O)$_2$, or S(O)$_2$NR$^9$;

R$^A$, R$^{A1}$, R$^B$ and R$^{B1}$ are each, independently, H, OH, halo, C$_{1-6}$ alkyl, C$_{1-6}$ alkenyl, C$_{1-6}$ alkynyl, C$_{1-6}$ haloalkyl, C$_{1-6}$ alkoxy, C$_{1-6}$ haloalkoxy, heterocyclyl, carbocyclyl, NR$^{10}$R$^{12}$, NR$^{10}$CO$_2$R$^{11}$; NR$^{10}$CONR$^{10}$R$^{12}$, NR$^{10}$SO$_2$NR$^{10}$R$^{12}$, NR$^{10}$—SO$_2$—R$^{11}$, CN, CONR$^{10}$R$^{12}$, CO$_2$R$^{10}$, NO$_2$, SR$^{10}$, SOR$^{10}$, SO$_2$R$^{10}$, or SO$_2$—NR$^{10}$R$^{12}$;

R$^1$ is C$_{1-6}$ alkyl, C$_{1-6}$ haloalkyl, C$_{1-6}$ hydroxyalkyl, —(C$_{0-6}$ alkyl)-O—(C$_{1-6}$ alkyl), —(C$_{0-6}$ alkyl)-S—(C$_{1-6}$ alkyl), —(C$_{0-6}$ alkyl)-(C$_{3-7}$ cycloalkyl)-(C$_{0-6}$ alkyl), OH, OR$^{10}$, SR$^{10}$, COR$^{11}$, CO$_2$R$^{10}$, CONR$^{10}$R$^{12}$, carbocyclyl, heterocyclyl, CN, NR$^{10}$R$^{12}$, NR$^{10}$SO$_2$R$^{10}$, NR$^{10}$COR$^{10}$, NR$^{10}$CO$_2$R$^{10}$, NR$^{10}$CONR$^{12}$, CR$^{10}$R$^{11}$CO$_2$R$^{10}$ or CR$^{10}$R$^{11}$OCOR$^{10}$;

R$^2$, R$^3$, R$^4$, R$^5$ and R$^6$ are each, independently, H, OH, halo, C$_{1-6}$ alkyl, C$_{1-6}$ haloalkyl, C$_{1-6}$ alkoxy, C$_{1-6}$ haloalkoxy, C$_{1-6}$ thioalkoxy, NR$^{10}$R$^{12}$, NR$^{10}$CO$_2$R$^{11}$, NR$^{10}$CONR$^{10}$R$^{12}$, NR$^{10}$SO$_2$NR$^{10}$R$^{12}$, NR$^{10}$—SO$_2$—R$^{11}$, heterocyclyl, carbocyclyl, carbocyclyloxy, heterocyclyloxy, CN, NO$_2$, COR$^{11}$, CONR$^{10}$R$^{12}$, CO$_2$R$^{10}$, NO$_2$, SR$^{10}$, SOR$^{10}$, SO$_2$R$^{10}$; or SO$_2$—NR$^{10}$R$^{12}$;

R$^7$ is H or C$_{1-8}$ alkyl optionally substituted by 1, 2, 3, 4, 5 or 6 substituents independently selected from halo, C$_{1-10}$ haloalkyl, Cy, CN, NO$_2$, OR$^a$, C(O)R$^b$, C(O)NR$^c$R$^d$, C(O) OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)$_2$R$^b$, S(O)NR$^c$R$^d$, S(O)$_2$R$^b$, NR$^c$S(O)$_2$R$^b$, and S(O)$_2$NR$^c$R$^d$;

or R$^7$ is H, C$_{1-8}$alkyl which is unsubstituted or substituted with 1-6 substituents selected from: hydroxy, halo, —O—C$_{1-6}$ alkyl, CN, —NR$^{12a}$R$^{12a}$, —NR$^{12a}$COR$^{13a}$, —NR$^{12a}$SO$_2$R$^{14a}$, —COR$^{11a}$, —CONR$^{12a}$R$^{12a}$, phenyl and heterocycle, where the alkyl, phenyl, and heterocycle are unsubstituted or substituted with 1-3 substituents selected from: halo, hydroxy, C$_{1-3}$ alkyl, C$_{1-3}$alkoxy, —CO$_2$H, —CO$_2$—C$_{1-6}$alkyl, and trifluoromethyl, and —SO$_2$C$_{1-6}$alkyl which is unsubstituted or substituted with 1-6 substituents selected from: hydroxy, halo, —O—C$_{1-6}$alkyl, CN, —NR$^{12a}$R$^{12a}$, —NR$^{12a}$COR$^{13a}$, —NR$^{12a}$SO$_2$R$^{14a}$, —COR$^{11a}$, —CONR$^{12a}$R$^{12a}$, phenyl and heterocycle, where the alkyl, phenyl, and heterocycle are unsubstituted or substituted with 1-3 substituents selected from: halo, hydroxy, C$_{1-3}$ alkyl, C$_{1-3}$ alkoxy, —CO$_2$H, —CO$_2$—C$_{1-6}$alkyl, and trifluoromethyl;

or R$^7$ is H, C$_{1-6}$alkyl unsubstituted or substituted with 1-3 substituents selected from: halo, hydroxy, —CO$_2$H, —CO$_2$C$_{1-6}$alkyl, and —O—C$_{1-3}$alkyl;

R$^8$ is C$_{1-10}$ alkyl, C$_{2-10}$ alkenyl, C$_{2-10}$ alkynyl, C$_{1-10}$ haloalkyl, aryl, cycloalkyl, heteroaryl, or heterocycloalkyl, wherein said C$_{1-10}$ alkyl, C$_{2-10}$ alkenyl, C$_{2-10}$ alkynyl, C$_{1-10}$ haloalkyl, aryl, cycloalkyl, heteroaryl, or heterocycloalkyl is optionally substituted with 1, 2, 3, 4, 5, or 6 substituents independently selected from oxo, hydroxy, halo, C$_{1-4}$ alkyl, C$_{1-4}$alkoxy, C$_{2-4}$ alkenyl, C$_{2-4}$ alkynyl, C$_{1-4}$ haloalkyl, C$_{1-4}$ hydroxyalkyl, C$_{1-4}$ cyanoalkyl, Cy', —(C$_{1-4}$ alkyl)-Cy', —C(O)—R$^{a'}$, CN, NO$_2$, —(CH$_2$)$_q$—OR$^{a'}$, —(CH$_2$)$_q$—SR$^{a'}$, —(CH$_2$)$_q$—C(O)R$^{b'}$, —(CH$_2$)$_q$—C(O)NR$^{c'}$R$^{d'}$, —(CH$_2$)$_q$—C(O)OR$^{a'}$, —(CH$_2$)$_q$—OC(O)R$^{b'}$, —(CH$_2$)$_q$—OC(O) NR$^{c'}$R$^{d'}$, —(CH$_2$)$_q$—NR$^{c'}$R$^{d'}$, —(CH$_2$)$_q$—NR$^{c'}$C(O)R$^{b'}$, —(CH$_2$)$_q$—NR$^{c'}$C(O)NR$^{c'}$R$^{d'}$, —(CH$_2$)$_q$—NR$^{c'}$C(O)OR$^{a'}$, —(CH$_2$)$_q$—S(O)R$^{b'}$, —(CH$_2$)$_q$—S(O)NR$^{c'}$R$^{d'}$, —(CH$_2$)$_q$—S(O)$_2$R$^{b'}$, —(CH$_2$)$_q$—NR$^{c'}$S(O)$_2$R$^{b'}$, and —(CH$_2$)$_q$—S(O)$_2$NR$^{c'}$R$^{d'}$;

or R$^8$ is selected from C$_{1-10}$alkyl, —SO$_2$C$_{1-10}$alkyl, pyridyl or phenyl, unsubstituted or substituted with 1-5 substituents selected from: hydroxy, halo, —O—C$_{1-6}$alkyl, —S—C$_{1-6}$ alkyl, CN, —NR$^{12a}$R$^{12a}$, —NR$^{12a}$COR$^{13a}$, —NR$^{12a}$SO$_2$R$^{14a}$, —COR$^{11a}$, —CONR$^{12a}$R$^{12a}$, —SO$_2$R$^{14a}$, heterocycle, =O (where the oxygen is connected via a double bond), phenoxy and phenyl, where the alkyl, phenyl, phenoxy and heterocycle are unsubstituted or substituted with 1-3 substituents selected from: halo, hydroxy, C$_{1-3}$alkyl, C$_{1-3}$alkoxy, —COR$^{11a}$, —CN, —NR$^{12a}$R$^{12a}$, —SO$_2$R$^{14a}$, —NR$^{12a}$COR$^{13a}$, —NR$^{12a}$SO$_2$R$^{14a}$, and —CONR$^{12a}$R$^{12a}$, where the alkyl and alkoxy are optionally substituted with 1-5 fluoro; or R$^8$ is a group of formula

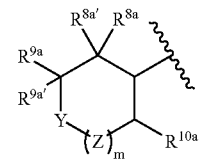

Y and Z are independently selected from —O—, —NR$^{12b}$, —S—, —SO—, SO$_2$—, —CR$^{12b}$R$^{12b}$, —NSO$_2$R$^{14b}$—, —NCOR$^{13b}$—, —CR$^{12b}$COR$^{11b}$—, —CR$^{12b}$OCOR$^{13b}$—, —C— and —CO—;

R$^{8a}$ and R$^{8a'}$ are independently selected from: hydrogen, C$_{1-6}$alkyl unsubstituted or substituted with 1-6 substituents selected from fluoro, C$_{1-3}$alkoxy, hydroxy and —COR$^{11b}$, fluoro, —O—C$_{1-3}$alkyl unsubstituted or substituted with 1-3 fluoro, C$_{3-6}$cycloalkyl, —O—C$_{3-6}$cycloalkyl, hydroxy, —COR$^{11b}$, —OCOR$^{13b}$;

or R$^7$ and R$^{8a}$ together are C$_{2-4}$alkyl or C$_{0-2}$alkyl-O—C$_{1-3}$ alkyl, forming a 5-7 membered ring;

R$^{9a}$ and R$^{9a'}$ are independently selected from: hydrogen, C$_{1-6}$alkyl unsubstituted or substituted with 1-6 substituents selected from fluoro, C$_{1-6}$alkoxy, hydroxy and —COR$^{11b}$, COR$^{11b}$, hydroxy and —O—C$_{1-6}$alkyl unsubstituted or substituted with 1-6 substituents selected from fluoro, C$_{1-3}$alkoxy, hydroxy and —COR$^{11b}$;

or R$^{8a}$ and R$^{9a}$ together are C$_{1-4}$alkyl or C$_{0-3}$alkyl-O—C$_{0-3}$ alkyl, forming a 3-6 membered ring;

R$^{10a}$ is selected from: hydrogen, C$_{1-6}$alkyl unsubstituted or substituted with 1-6 fluoro, fluoro, —O—C$_{3-6}$cycloalkyl and —O—C$_{1-3}$alkyl unsubstituted or substituted with 1-6 fluoro;

or R$^{8a}$ and R$^{10a}$ together are C$_{2-3}$alkyl, forming a 5-6 membered ring, where said alkyl is unsubstituted or substituted with 1-3 substituents independently selected from halo, hydroxy, —COR$^{11b}$, C$_{1-3}$alkyl and C$_{1-3}$alkoxy;

or R$^{8a}$ and R$^{10a}$ together are O—C$_{1-2}$alkyl-O—C$_{1-2}$alkyl, forming a 6-8 membered ring, where said alkyl is unsubstituted or substituted with 1-3 substituents independently selected from halo, hydroxy, —COR$^{11b}$, C$_{1-3}$alkyl and C$_{1-3}$alkoxy;

or R$^{8a}$ and R$^{10a}$ together are —O—C$_{1-2}$alkyl-O—C$_{1-2}$ alkyl, forming a 6-7 membered ring, where said alkyl is unsubstituted or substituted with 1-3 substituents independently selected from halo, hydroxy, —COR$^{11b}$, C$_{1-3}$alkyl and C$_{1-3}$alkoxy;

R$^{11a}$ and R$^{11b}$ are independently selected from: hydroxy, hydrogen, C$_{1-6}$alkyl, —O—C$_{1-6}$alkyl, benzyl, phenyl and C$_{3-6}$cycloalkyl, where said alkyl, phenyl, benzyl and cycloalkyl groups are unsubstituted or substituted with 1-3 substituents independently selected from halo, hydroxy, $C_{1-3}$alkyl, $C_{1-3}$alkoxy, —$CO_2H$, —$CO_2$—$C_{1-6}$alkyl, and trifluoromethyl;

$R^{12a}$ and $R^{12b}$ are independently selected from: hydrogen, $C_{1-6}$alkyl, benzyl, phenyl, $C_{3-6}$ cycloalkyl, where the alkyl, phenyl, benzyl, and cycloalkyl groups are unsubstituted or substituted with 1-3 substituents independently selected from: halo, hydroxy, $C_{1-3}$alkyl, $C_{1-3}$alkoxy, —$CO_2H$, —$CO_2$—$C_{1-6}$alkyl, and trifluoromethyl; also $R^{12a}$ and $R^{12b}$ can be selected from: $C_{1-6}$alkyl unsubstituted or substituted with 1-6 substituents selected from fluoro, $C_{1-3}$alkoxy, hydroxy and —$COR^{11b}$, fluoro, —O—$C_{1-3}$alkyl unsubstituted or substituted with 1-6 fluoro, $C_{3-6}$cycloalkyl, —O—$C_{3-6}$cycloalkyl, hydroxy, —O—$C_{1-6}$alkyl unsubstituted or substituted with 1-6 substituents selected from fluoro, $C_{1-3}$alkoxy, hydroxy and —$COR^{11b}$;

$R^{13a}$ and $R^{13b}$ are independently selected from: hydrogen, $C_{1-6}$alkyl, —O—$C_{1-6}$alkyl, benzyl, phenyl, $C_{3-6}$ cycloalkyl, where the alkyl, phenyl, benzyl, and cycloalkyl groups are unsubstituted or substituted with 1-3 substituents independently selected from: halo, hydroxy, $C_{1-3}$alkyl, $C_{1-3}$alkoxy, —$CO_2H$, —$CO_2$—$C_{1-6}$alkyl, and trifluoromethyl;

$R^{14a}$ and $R^{14b}$ are independently selected from: hydroxy, $C_{1-6}$alkyl, —O—$C_{1-6}$alkyl, benzyl, phenyl, $C_{3-6}$ cycloalkyl, where the alkyl, phenyl, benzyl, and cycloalkyl groups are unsubstituted or substituted with 1-3 substituents independently selected from: halo, hydroxy, $C_{1-3}$alkyl, $C_{1-3}$alkoxy, —$CO_2H$, —$CO_2$—$C_{1-6}$alkyl, and trifluoromethyl;

Cy and Cy' are, independently, aryl, heteroaryl, cycloalkyl, or heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $C(O)NR^{c''}R^{d''}$, $NR^{c''}R^{d''}$, $NR^{c''}C(O)R^{b''}$, $NR^{c''}C(O)OR^{a''}$, $S(O)R^{b''}$, $S(O)NR^{c''}R^{d''}$, $S(O)_2R^{b''}$, and $S(O)_2NR^{c''}R^{d''}$;

$R^9$ is H, $C_{1-10}$ alkyl, $C_{1-6}$ haloalkyl, $C_{2-6}$ alkenyl, or $C_{2-6}$ alkynyl, wherein said $C_{1-10}$ alkyl, $C_{1-6}$ haloalkyl, $C_{2-6}$ alkenyl, or $C_{2-6}$ alkynyl is optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

$R^{10}$ is H, $C_{1-6}$ alkyl, benzyl, phenyl, or $C_{3-6}$ cycloalkyl, wherein said $C_{1-6}$ alkyl, benzyl, phenyl, or $C_{3-6}$ cycloalkyl is optionally substituted with 1, 2, or 3 substituents independently selected from halo, OH, $C_{1-3}$alkyl, $C_{1-3}$ haloalkyl, $C_{1-3}$ alkoxy, $C_{1-3}$ haloalkoxy, $CO_2H$, and $CO_2$-($C_{1-6}$ alkyl);

$R^{11}$ is H, OH, $C_{1-6}$ alkyl, $C_{1-6}$ alkoxy, benzyl, phenyl, benzyloxy, phenyloxy, $C_{3-6}$ cycloalkyl or $C_{3-6}$ cycloalkyloxy, wherein said $C_{1-6}$ alkyl, $C_{1-6}$ alkoxy, benzyl, phenyl, benzyloxy, phenyloxy, $C_{3-6}$ cycloalkyl or $C_{3-6}$ cycloalkyloxy, is optionally substituted with 1, 2 or 3 substituents independently selected from halo, OH, $C_{1-3}$ alkyl, $C_{1-3}$ alkoxy, $CO_2H$, $CO_2$—($C_{1-6}$ alkyl) and $CF_3$;

$R^{12}$ is H, $C_{1-6}$ alkyl, benzyl, phenyl, or $C_{3-6}$ cycloalkyl, wherein said $C_{1-6}$ alkyl, benzyl, phenyl, or $C_{3-6}$ cycloalkyl is optionally substituted with 1, 2, or 3 substituents independently selected from halo, OH, $C_{1-3}$ alkyl, $C_{1-3}$ haloalkyl, $C_{1-3}$ alkoxy, $C_{1-3}$ haloalkoxy, $CO_2H$, and $CO_2$—($C_{1-6}$ alkyl);

$R^a$, $R^{a'}$ and $R^{a''}$ are, independently, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, amino, halo, $C_{1-6}$ alkyl, aryl, arylalkyl, heteroaryl, heteroarylalkyl, cycloalkyl and heterocycloalkyl;

$R^b$, $R^{b'}$ and $R^{b''}$ are, independently, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

$R^c$ and $R^d$ are, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

or $R^c$ and $R^d$ together with the N atom to which they are attached form a 4-, 5-, 6- or 7-membered heterocycloalkyl group optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

$R^{c'}$ and $R^{d'}$ are, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

or $R^{c'}$ and $R^{d'}$ together with the N atom to which they are attached form a 4-, 5-, 6- or 7-membered heterocycloalkyl group optionally substituted with 1, 2, or 3 substituents independently selected from OH, amino, halo, $C_{1-6}$alkyl, $C_{1-6}$ haloalkyl, aryl, arylalkyl, heteroaryl, heteroarylalkyl, cycloalkyl and heterocycloalkyl;

$R^{c''}$ and $R^{d''}$ are, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

or $R^{c''}$ and $R^{d''}$ together with the N atom to which they are attached form a 4-, 5-, 6- or 7-membered heterocycloalkyl group optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

m is 0, 1, or 2;

n is 0 or 1;

p is 0 or 1; and q is 0, 1, 2, or 3.

In some embodiments, when n is 0, $R^8$ is other than a compound of the formula:

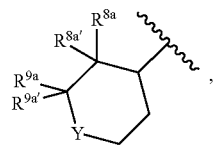

wherein Y is —O—, —S—, —NR$^{12b}$—, —CR$^{12b}$R$^{12b}$—; R$^{8a}$, R$^{8a'}$, R$^{9a'}$ and R$^{9a'}$ are independently selected from hydrogen, C$_{1-3}$ alkoxy, C$_{1-3}$ haloalkoxy, C$_{3-6}$ cycloalkyloxy, hydroxy, C$_{1-6}$ alkyl, halo, C$_{3-6}$ cycloalkyl, CO$_2$R$^{10}$, OCOR$^{10}$, wherein said C$_{1-6}$alkyl is optionally substituted with one or more substituents selected from F, C$_{1-3}$ alkoxy, OH or CO$_2$R$^{10}$; wherein neither R$^{8a}$ and R$^{8a'}$ nor R$^{9a}$ and R$^{9a'}$ form with the carbon atom they are attached to a 3-7 membered spirocyclyl group.

In some embodiments, when n is 0, $R^8$ is

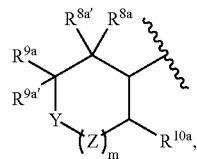

m is 1, Y is —O—, —S—, —NR$^{12b}$—, —CR$^{12b}$R$^{12b}$—, Z is —CR$^{12b}$R$^{12b}$—, R$^{12b}$ is hydrogen, R$^{8a}$, R$^{8a'}$, R$^{9a'}$ and R$^{9a}$ are other than hydrogen, C$_{1-3}$ alkoxy, C$_{1-3}$ haloalkoxy, C$_{3-6}$ cycloalkyloxy, hydroxy, C$_{1-6}$ alkyl, halo, C$_{3-6}$ cycloalkyl, CO$_2$R$^{10}$, OCOR$^{10}$, wherein said C$_{1-6}$ alkyl is optionally substituted with one or more substituents selected from F, C$_{1-3}$ alkoxy, OH or CO$_2$R$^{10}$; wherein neither R$^{8a}$ and R$^{8a'}$ nor R$^{9a}$ and R$^{9a}$ form with the carbon atom they are attached to become a 3-7 membered spirocyclyl group.

In some embodiments, when n is 0, $R^8$ is

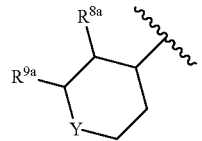

Y is —O—, —S—, —NR$^{12b}$—, —CR$^{12b}$R$^{12b-}$, wherein R$^{8a}$, R$^{8a'}$, R$^{9a'}$ and R$^{9a}$ are other than hydrogen, C$_{1-3}$ alkoxy, C$_{1-3}$ haloalkoxy, C$_{3-6}$ cycloalkyloxy, hydroxy, C$_{1-6}$ alkyl, halo, C$_{3-6}$ cycloalkyl, CO$_2$R$^{10}$, OCOR$^{10}$, wherein said C$_{1-6}$ alkyl is optionally substituted with one or more substituents selected from F, C$_{1-3}$ alkoxy, OH or CO$_2$R$^{10}$ wherein neither R$^{8a}$ and R$^{8a'}$ nor R$^{9a'}$ and R$^{9a}$ form with the carbon atom they are attached to become a 3-7 membered spirocyclyl group.

In some embodiments, $R^8$ is

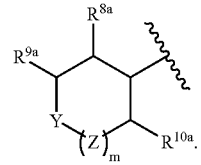

Y is —O—, —S—, —NR$^{12b}$—, —CR$^{12b}$R$^{12b-}$, wherein R$^{8a}$, and R$^{9a}$ are other than hydrogen, C$_{1-3}$ alkoxy, C$_{1-3}$ haloalkoxy, C$_{3-6}$ cycloalkyloxy, hydroxy, C$_{1-6}$ alkyl, halo, C$_{3-6}$ cycloalkyl, CO$_2$R$^{10}$, OCOR$^{10}$, wherein said C$_{1-6}$ alkyl is optionally substituted with one or more substituents selected from F, C$_{1-3}$ alkoxy, OH or CO$_2$R$^{10}$. In addition, R$^{8a}$ and R$^{9a}$ do not form with the carbon atom they are attached to become a 3-7 membered spirocyclyl group with the carbon atom.

In some embodiments, when n is 0, $R^8$ is other than a tetrahydropyran-4-yl of the formula:

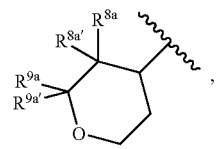

wherein R$^{8a}$, R$^{8a'}$, R$^{9a}$ and R$^{9a'}$ are independently selected from hydrogen, C$_{1-3}$ alkoxy, C$_{1-3}$ haloalkoxy, C$_{3-6}$ cycloalkyloxy, hydroxy, C$_{1-6}$ alkyl, halo, C$_{3-6}$ cycloalkyl, CO$_2$R$^{10}$, OCOR$^{10}$, wherein said C$_{1-6}$ alkyl is optionally substituted with one or more substituents selected from F, C$_{1-3}$ alkoxy, OH or CO$_2$R$^{10}$; wherein neither R$^{8a}$ and R$^{8a''}$ nor R$^{9a}$ and R$^{9a'}$ form with the carbon atom they are attached to a 3-7 membered spirocyclyl group.

In some embodiments, when n is 0, $R^8$ is other than a tetrahydropyran-4-yl of the formula:

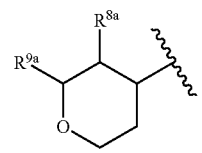

wherein R$^{8a}$ and R$^{9a}$ are independently selected from hydrogen, C$_{1-3}$ alkoxy, C$_{1-3}$ haloalkoxy, C$_{3-6}$ cycloalkyloxy, hydroxy, C$_{1-6}$ alkyl, halo, C$_{3-6}$ cycloalkyl, CO$_2$R$^{10}$, OCOR$^{10}$, wherein said C$_{1-6}$ alkyl is optionally substituted with one or more substituents selected from F, C$_{1-3}$ alkoxy, OH or CO$_2$R$^{10}$. In addition, R$^{8a}$ and R$^{9a}$ do not form with the carbon atom they are attached to become a 3-7 membered spirocyclyl group with the carbon atom.

In some embodiments, when n is 0, $R^8$ is other than substituted or unsubstituted tetrahydropyran-4-yl.

In some embodiments, $R^8$ is other than substituted or unsubstituted tetrahydrothiopyran-4-yl.

In some embodiments, $R^8$ is other than substituted or unsubstituted 4-piperidinyl.

In some embodiments, $R^8$ is other than substituted or unsubstituted 4-cyclohexanyl.

In some embodiments, $R^8$ is

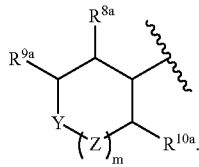

In some embodiments, $R^8$ is

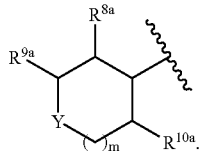

In some embodiments, m is 0.
In some embodiments, m is 1.
In some embodiments, m is 2.
In some embodiments, $R^{12}$ is H, $C_{1-6}$ alkyl, benzyl, phenyl, or $C_{3-6}$ cycloalkyl, wherein said $C_{1-6}$ alkyl, benzyl, phenyl, or $C_{3-6}$ cycloalkyl is optionally substituted with 1, 2, or 3 substituents independently selected from halo, OH, $C_{1-3}$ alkyl, $C_{1-3}$ haloalkyl, $C_{1-3}$ alkoxy, $C_{1-3}$ haloalkoxy, $CO_2H$, and $CO_2$—($C_{1-6}$ alkyl).
In some embodiments, W is

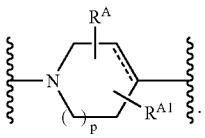

In some embodiments, W is

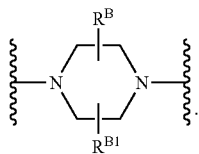

In some embodiments, V is $CR^5$.
In some embodiments, X is $CR^2$.
In some embodiments, Y is $CR^3$.
In some embodiments, Z is $CR^4$.
In some embodiments, X is $CR^2$; Y is $CR^3$; and Z is $CR^4$.
In some embodiments, V is $CR^5$, X is $CR^2$; Y is $CR^3$; and Z is $CR^4$.
In some embodiments, $R^A$, $R^{A1}$, $R^B$ and $R^{B1}$ are each, independently, H, OH, halo, $C_{1-6}$ alkyl, $C_{1-6}$ alkenyl, $C_{1-6}$ alkynyl, $C_{1-6}$ haloalkyl, $C_{1-6}$ alkoxy or $C_{1-6}$ haloalkoxy.
In some embodiments, $R^A$, $R^{A1}$, $R^B$ and $R^{B1}$ are each, independently, H, OH or $C_{1-6}$ alkoxy.
In some embodiments, $R^A$, $R^{A1}$, $R^B$ and $R^{B1}$ are each, independently, H or OH.
In some embodiments, $R^1$ is $C_{1-6}$ alkyl, $C_{1-6}$ hydroxyalkyl, —($C_{0-6}$ alkyl)-O—($C_{1-6}$ alkyl), or heterocyclyl.
In some embodiments, $R^1$ is $C_{1-6}$ alkyl.

In some embodiments, $R^1$ is prop-2-yl.
In some embodiments, one of $R^5$ and $R^6$ is other than H.
In some embodiments, one of $R^5$ and $R^6$ is $C_{1-4}$ haloalkyl.
In some embodiments, $R^6$ is $C_{1-4}$ haloalkyl.
In some embodiments, $R^6$ is $CF_3$.
In some embodiments, $R^7$ is H.
In some embodiments, $R^7$ is $C_{1-8}$ alkyl.
In some embodiments, $R^8$ is $C_{1-10}$ alkyl, aryl, cycloalkyl, heteroaryl, or heterocycloalkyl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, Cy', —($C_{1-4}$ alkyl)-Cy', CN, $NO_2$, —$(CH_2)_q$—$OR^{a'}$, —$(CH_2)_q$—$SR^{a'}$, —$(CH_2)_q$—$C(O)R^{b'}$, —$(CH_2)_q$—$C(O)NR^{c'}R^{d'}$, —$(CH_2)_q$—$C(O)OR^{a'}$, —$(CH_2)_q$—$OC(O)R^{b'}$, —$(CH_2)_q$—$OC(O)NR^{c'}R^{d'}$, —$(CH_2)_q$—$NR^{c'}R^{d'}$, —$(CH_2)_q$—$NR^{c'}C(O)R^{b'}$, —$(CH_2)_q$—$NR^{c'}C(O)NR^{c'}R^{d'}$, —$(CH_2)_q$—$NR^{c'}C(O)OR^{a'}$, —$(CH_2)_q$—$S(O)R^{b'}$, —$(CH_2)_qS(O)NR^{c'}R^{d'}$, —$(CH_2)_q$—$S(O)_2R^{b'}$, —$(CH_2)_q$—$NR^{c'}S(O)_2R^{b'}$, and —$(CH_2)_q$—$S(O)_2NR^{c'}R^{d'}$.

In some embodiments, $R^8$ is $C_{1-10}$ alkyl optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, Cy', —($C_{1-4}$ alkyl)-Cy', CN, $NO_2$, —$(CH_2)_q$—$OR^{a'}$, —$(CH_2)_q$—$SR^{a'}$, —$(CH_2)_q$—$C(O)R^{b'}$, —$(CH_2)_q$—$C(O)NR^{c'}R^{d'}$, —$(CH_2)_q$—$C(O)OR^{a'}$, —$(CH_2)_q$—$OC(O)R^{b'}$, —$(CH_2)_q$—$OC(O)NR^{c'}R^{d'}$, —$(CH_2)_q$—$NR^{c'}R^{d'}$, —$(CH_2)_q$—$NR^{c'}C(O)R^{b'}$, —$(CH_2)_q$—$NR^{c'}C(O)NR^{c'}R^{d'}$, —$(CH_2)_q$—$NR^{c'}C(O)OR^{a'}$, —$(CH_2)_q$—$S(O)R^{b'}$, —$(CH_2)_q$—$S(O)NR^{c'}R^{d'}$, —$(CH_2)_q$—$S(O)_2R^{b'}$, —$(CH_2)_q$—$NR^{c'}S(O)_2R^{b'}$, and —$(CH_2)_q$—$S(O)_2NR^{c'}R^{d'}$.

In some embodiments, $R^8$ is aryl or heteroaryl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, Cy', —($C_{1-4}$ alkyl)-Cy', CN, $NO_2$, —$(CH_2)_q$—$OR^{a'}$, —$(CH_2)_q$—$SR^{a'}$, —$(CH_2)_q$—$C(O)R^{b'}$, —$(CH_2)_q$—$C(O)NR^{c'}R^{d'}$, —$(CH_2)_q$—$C(O)OR^{a'}$, —$(CH_2)_q$—$OC(O)R^{b'}$, —$(CH_2)_q$—$OC(O)NR^{c'}R^{d'}$, —$(CH_2)_q$—$NR^{c'}R^{d'}$, —$(CH_2)_q$—$NR^{c'}C(O)R^{b'}$, —$(CH_2)_q$—$NR^{c'}C(O)NR^{c'}R^{d'}$, —$(CH_2)_q$—$NR^{c'}C(O)OR^{a'}$, —$(CH_2)_q$—$S(O)R^{b'}$, —$(CH_2)_q$—$S(O)NR^{c'}R^{d'}$, —$(CH_2)_q$—$S(O)_2R^{b'}$, —$(CH_2)_q$—$NR^{c'}S(O)_2R^{b'}$, and —$(CH_2)_q$—$S(O)_2NR^{c'}R^{d'}$.

In some embodiments, $R^8$ is cycloalkyl or heterocycloalkyl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, Cy', —($C_{1-4}$ alkyl)-Cy', CN, $NO_2$, —$(CH_2)_q$—$OR^{a'}$, —$(CH_2)_q$—$SR^{a'}$, —$(CH_2)_q$—$C(O)R^{b'}$, —$(CH_2)_q$—$C(O)NR^{c'}R^{d'}$, —$(CH_2)_q$—$C(O)OR^{a'}$, —$(CH_2)_q$—$OC(O)R^{b'}$—$(CH_2)_q$—$OC(O)NR^{c'}R^{d'}$, —$(CH_2)_q$—$NR^{c'}R^{d'}$, —$(CH_2)_q$—$NR^{c'}C(O)R^{b'}$, —$(CH_2)_q$—$NR^{c'}C(O)NR^{c'}R^{d'}$, —$(CH_2)_q$—$NR^{c'}C(O)OR^{a'}$, —$(CH_2)_q$—$S(O)R^{b'}$, —$(CH_2)_q$—$S(O)NR^{c'}R^{d'}$—$(CH_2)_q$—$S(O)_2R^{b'}$, —$(CH_2)_q$—$NR^{c'}S(O)_2R^{b'}$, and —$(CH_2)_q$—$S(O)_2NR^{c'}R^{d'}$.

In some embodiments, $R^8$ is phenyl optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, Cy', —($C_{1-4}$ alkyl)-Cy', CN, $NO_2$, —$(CH_2)_q$—$OR^{a'}$, —$(CH_2)_q$—$SR^{a'}$, —$(CH_2)_q$—$C(O)R^{b'}$, —$(CH_2)_q$—$C(O)NR^{c'}R^{d'}$, —$(CH_2)_q$—$C(O)OR^{a'}$, —$(CH_2)_q$—$OC(O)R^{b'}$, —$(CH_2)_q$—$OC(O)NR^{c'}R^{d'}$, —$(CH_2)_q$—$NR^{c'}R^{d'}$, —$(CH_2)_q$—$NR^{c'}C(O)R^{b'}$, —$(CH_2)_q$—$NR^{c'}C(O)NR^{c'}R^{d'}$, —$(CH_2)_q$—$NR^{c'}C(O)OR^{a'}$, —(CH$_2$)$_q$—S(O)R$^{b'}$, —(CH$_2$)$_q$—S(O)NR$^{c'}$R$^{d'}$, —(CH$_2$)$_q$—S(O)$_2$R$^{b'}$, —(CH$_2$)$_q$—NR$^{c'}$S(O)$_2$R$^{b'}$ and —(CH$_2$)$_q$—S(O)$_2$NR$^{c'}$R$^{d'}$.

In some embodiments, R$^8$ is selected from: C$_{1-8}$alkyl optionally substituted with hydroxyl, C$_{1-6}$alkyl substituted with 1-6 fluoro, C$_{1-6}$alkyl substituted with —COR$^{11}$, benzyl, unsubstituted or substituted with 1-3 substituents selected from: hydroxy, methoxy, chloro, fluoro, —COR$^{11}$, methyl and trifluoromethyl, —CH$_2$-pyridyl, unsubstituted or substituted with 1-3 substituents selected from: hydroxy, methoxy, chloro, fluoro, methyl and trifluoromethyl.

In some embodiments, R$^{8a}$ is selected from: hydrogen, C$_{1-3}$alkyl unsubstituted or substituted with 1-6 fluoro, —O—C$_{1-3}$alkyl, fluoro and hydroxyl.

In some embodiments, R$^{8a}$ is halo.

In some embodiments, R$^{8a}$ is F.

In some embodiments, R$^{8a}$ is H.

In some embodiments, R$^{9a}$ is H.

In some embodiments, R$^{10a}$ is H.

In some embodiments, Y is O.

In some embodiments, n is 0 and R$^8$ is C$_{1-8}$ alkyl, substituted with 1, 2, or 3 substituents independently selected from OH, halo, and —(CH$_2$)$_q$—C(O)R$^{b'}$.

In some embodiments, n is 1, L is C$_{1-4}$ alkylenyl, and R$^8$ is aryl or heteroaryl each optionally substituted with 1, 2, or 3 substituents selected from halo, C$_{1-4}$ alkyl, C$_{1-4}$ haloalkyl, OR$^{a'}$, and —(CH$_2$)$_q$—C(O)R$^{b'}$.

In some embodiments, L is C$_{1-4}$ alkylenyl.

In some embodiments, L is methylene.

In some embodiments, L is C(O) or S(O)$_2$.

In some embodiments, n is 0.

In some embodiments, n is 1.

In some embodiments, compounds of the invention have Formula Ia:

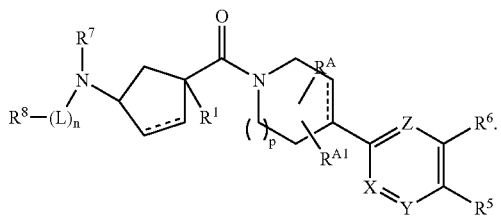

Ia

In some embodiments, compounds of the invention have Formula Ib, Ic or Id:

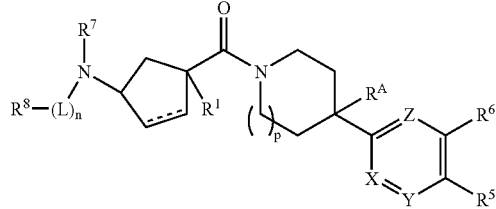

Ib

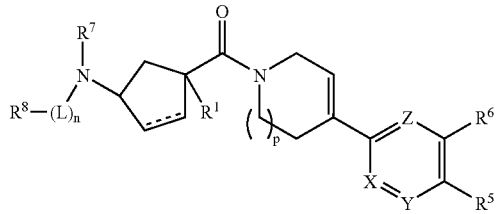

Ic

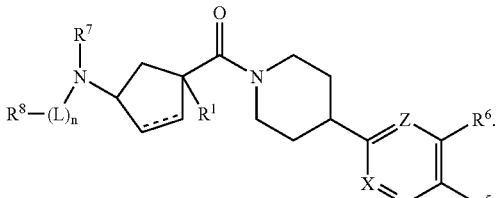

Id

In some embodiments, compounds of the invention have Formula Ie or If:

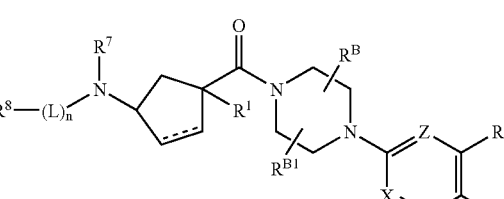

Ie

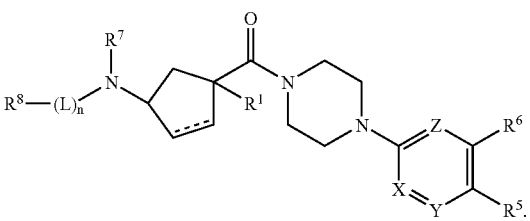

If

In some embodiments, compounds of the invention have Formula Ig:

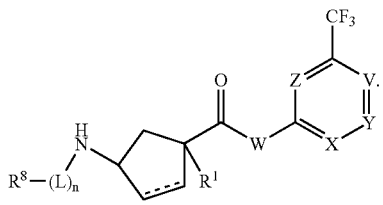

Ig

At various places in the present specification, substituents of compounds of the invention are disclosed in groups or in ranges. It is specifically intended that the invention include each and every individual subcombination of the members of such groups and ranges. For example, the term "C$_{1-6}$ alkyl" is specifically intended to individually disclose methyl, ethyl, C$_3$ alkyl, C$_4$ alkyl, C$_5$ alkyl, and C$_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylenyl" refers to a divalent alkyl linking group.

As used herein, "alkenyl" refers to an alkyl group having one or more double carbon-carbon bonds. Example alkenyl groups include ethenyl, propenyl, cyclohexenyl, and the like. The term "alkenylenyl" refers to a divalent linking alkenyl group.

As used herein, "alkynyl" refers to an alkyl group having one or more triple carbon-carbon bonds. Example alkynyl groups include ethynyl, propynyl, and the like. The term "alkynylenyl" refers to a divalent linking alkynyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "carbocyclyl" groups are saturated (i.e., containing no double or triple bonds) or unsaturated (i.e., containing one or more double or triple bonds) cyclic hydrocarbon moieties. Carbocyclyl groups can be mono-, poly- (e.g., 2, 3 or 4 fused rings). Example carbocyclyl groups include cyclopropyl, cyclobutyl, cyclopentyl, cyclohexyl, cycloheptyl, cyclopentenyl, 1,3-cyclopentadienyl, cyclohexenyl, norbornyl, norpinyl, norcarnyl, adamantyl, phenyl, and the like. Carbocyclyl groups can be aromatic (e.g., "aryl") or non-aromatic (e.g., "cycloalkyl"). In some embodiments, carbocyclyl groups can have from about 3 to about 30 carbon atoms, about 3 to about 20, about 3 to about 10, or about 3 to about 7 ring-forming carbon atoms.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems as well as spiro ring systems. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of pentane, pentene, hexane, and the like. In some embodiments, cycloalkyl groups can have from about 3 to about 10, about 3 to about 10, or about 3 to about 7 ring-forming carbon atoms. In some embodiments, the cycloalkyl group can have 0, 1, 2, 3, 4 or 5 double or triple bonds. In yet further embodiments, one or more ring-forming carbon atoms of a cycloalkyl group can be substituted by an oxo or sulfido group.

As used herein, "heterocyclyl" or "heterocycle" refers to a saturated or unsaturated cyclic hydrocarbon wherein one or more of the ring-forming atoms is a heteroatom such as O, S, or N. Heterocyclyl groups can be aromatic (e.g., "heteroaryl") or non-aromatic (e.g., "heterocycloalkyl"). Heterocyclyl groups can also correspond to hydrogenated and partially hydrogenated heteroaryl groups. Heterocyclyl groups can include mono- or polycyclic (e.g., having 2, 3 or 4 fused rings) ring systems. Heterocyclyl groups can be characterized as having 3-14 or 3-7 ring-forming atoms. In some embodiments, heterocyclyl groups can contain, in addition to at least one heteroatom, from about 1 to about 13, about 2 to about 10, or about 2 to about 7 carbon atoms and can be attached through a carbon atom or heteroatom. In further embodiments, any ring-forming carbon or heteroatom can be oxidized (e.g., have an oxo or sulfido substituent), or a nitrogen atom can be quaternized. Examples of heterocyclyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like, as well as any of the groups listed below for "heteroaryl" and "heterocycloalkyl." Further example heterocycles include pyrimidinyl, phenanthridinyl, phenanthrolinyl, phenazinyl, phenothiazinyl, phenoxathiinyl, phenoxazinyl, phthalazinyl, piperazinyl, piperidinyl, 3,6-dihydropyridyl, 1,2,3,6-tetrahydropyridyl, 1,2,5,6-tetrahydropyridyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrazolyl, 6H-1,2,5-thia-diazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, quinazolinyl, quinolinyl, 4H-quinolizinyl, quinoxalinyl, quinuclidinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, methylenedioxyphenyl, morpholinyl, naphthyridinyl, deca-hydroquinolinyl, 2H,6H-1,5,2dithiazinyl, dihydrofuro[2,3-b]tetrahydrofuran, furanyl, furazanyl, carbazolyl, 4aH-carbazolyl, carbolinyl, chromanyl, chromenyl, cinnolinyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl and isoxazolyl. Further examples of heterocycles include azetidin-1-yl, 2,5-dihydro-1H-pyrrol-1-yl, piperindin-1yl, piperazin-1-yl, pyrrolidin-1-yl, isoquinol-2-yl, pyridin-1-yl, 3,6-dihydropyridin-1-yl, 2,3-dihydroindol-1-yl, 1,3,4,9-tetrahydrocarbolin-2-yl, thieno[2,3-c]pyridin-6-yl, 3,4,10,10a-tetrahydro-1H-pyrazino[1,2-a]indol-2-yl, 1,2,4,4a,5,6-hexahydro-pyrazino[1,2-a]quinolin-3-yl, pyrazino[1,2-a]quinolin-3-yl, diazepan-1-yl, 1,4,5,6-tetrahydro-2H-benzo[f]isoquinolin-3-yl, 1,4,4a,5,6,10b- hexahydro-2H-benzo[f]isoquinolin-3-yl, 3,3a,8,8 a-tetrahydro-1H-2-aza-cyclopenta[a]inden-2-yl, and 2,3,4,7-tetrahydro-1H-azepin-1-yl, azepan-1-yl.

As used herein, "heteroaryl" groups refer to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl (furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the non-aromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 double or triple bonds.

As used herein, "spirocyclyl" refers to a 3-14 membered cycloalkyl or 3-14 membered heterocycloalkyl group sharing one atom with a further cycloalkyl or heterocycloalkyl group to which it is attached.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "thioalkoxy" refers to an —S-alkyl group.

As used herein, "haloalkoxy" refers to an —O-haloalkyl group. An example haloalkoxy group is $OCF_3$.

As used herein, "carbocyclyloxy" refers to —O-carbocyclyl.

As used herein, "heterocyclyloxy" refers to —O-heterocyclyl.

As used herein, "cycloalkyloxy" refers to —O-cycloalkyl.

As used herein, "carbocyclylalkyl" refers to alkyl substituted by carbocyclyl.

As used herein, "aralkyl" or "arylalkyl" refers to an alkyl group substituted by an aryl group.

As used herein, "cycloalkylalkyl" refers to an alkyl group substituted by an cycloalkyl group.

As used herein, "heterocyclylalkyl" refers to an alkyl moiety substituted by a heterocarbocyclyl group. Example heterocyclylalkyl groups include "heteroarylalkyl" (alkyl substituted by heteroaryl) and "heterocycloalkylalkyl" (alkyl substituted by heterocycloalkyl). In some embodiments, heterocyclylalkyl groups have from 3 to 24 carbon atoms in addition to at least one ring-forming heteroatom.

As used herein, "hydroxyalkyl" refers to an alkyl group substituted by a hydroxyl group.

As used herein, "cyanoalkyl" refers to an alkyl group substituted by a cyano group.

As used herein, "amino" refers to $NH_2$.

As used herein "oxo" refers to $=O$.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as P-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms, such as keto-enol tautomers.

Compounds of the invention can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418 and Journal of *Pharmaceutical Science*, 66, 2 (1977), each of which is incorporated herein by reference in its entirety.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

Compounds of the invention, including salts, hydrates, and solvates thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Preparation of compounds of the invention can involve the protection and deprotection of various chemical groups. The need for protection and deprotection, and the selection of appropriate protecting groups can be readily determined by one skilled in the art. The chemistry of protecting groups can be found, for example, in T. W. Greene and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Examplary synthetic routes to compounds of the invention are provided in Schemes 1-13 below, where constituent members of the depicted formulae are defined herein.

3-Aminopentanecarboxylic acids of formula 1-5 can be prepared using the protocol described in Scheme 1. The commercially available carboxylic acid 1-1 can be converted to an ester such as a methyl ester by treatment with iodomethane/potassium carbonate in DMF. The resulting ester 1-2 can be subjected to an alkylation with a halide such as an iodide ($R^1$I) using a base such as lithium hexamethyldisilazide (LHMDS) to provide the alkylated product 1-3 as a mixture of cis and trans diastereomers (4:1 ratio). The minor trans diastereomer can be removed by crystallization following hydrolysis of the ester to an acid. The resulting enantiopure acid 1-4 can be subjected to a hydrogenation using a catalyst such as Pd—C to afford the saturated carboxylic acid 1-5.

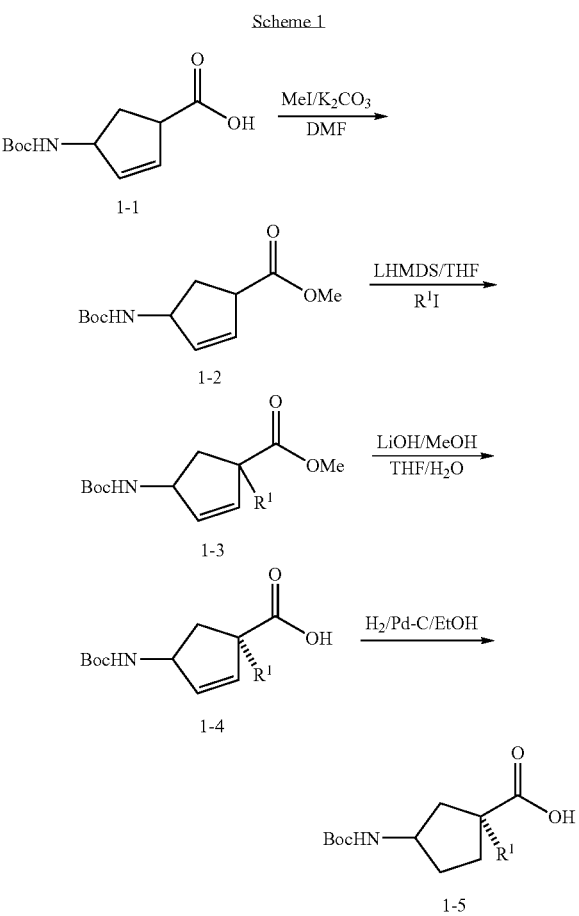

Cyclopentanecarboxylic acids of formula 2-5 can be prepared using the procedures outlined in Scheme 2. The commercially available 3-oxocyclopentanecarboxylic acid 2-1 can be converted to an ester such as methyl ester. The ketone of the resulting ester 2-2 can be protected by treatment with trimethyl orthoformate in the presence of an acidic catalyst such as paratoluenesulfonic acid. Alkylation of the resulting ketal 2-3 with an alkyl iodide (R¹I) can be accomplished using a base such as LHMDS. Hydrolysis of the alkylated ester 2-4 using a base such as LiOH, NaOH or KOH provides the carboxylic acids of formula 2-5.

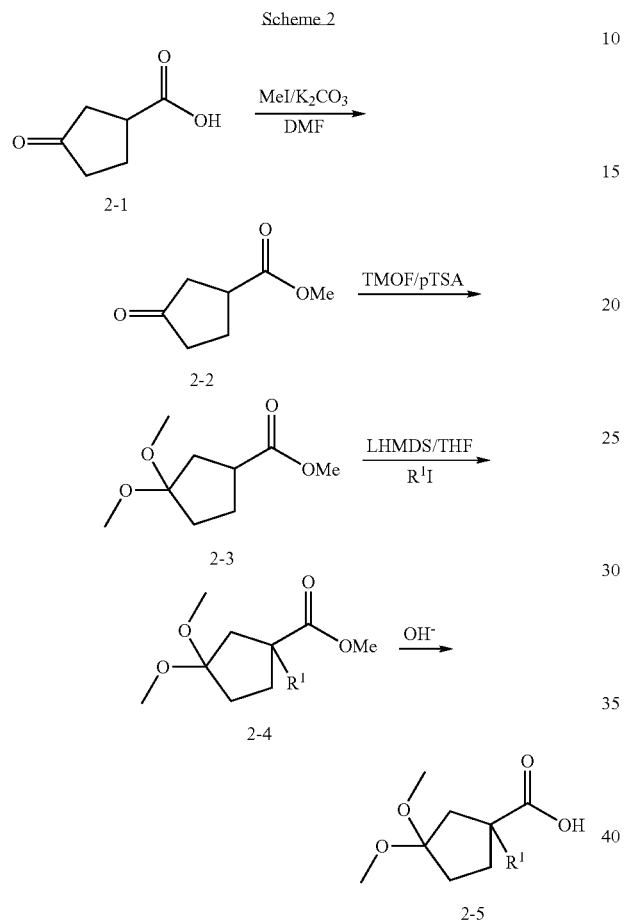

Piperazine derivatives can be prepared using the procedures depicted in Scheme 3. Coupling of a piperazine derivative of formula 3-2 with an iodobenzene derivative of formula 3-1 using copper(I) iodide and potassium phosphate gives rise to the intermediate 3-3. Removal of the Boc group using an acid such as HCl in dioxane or TFA provides the piperazine derivatives of formula 3-4.

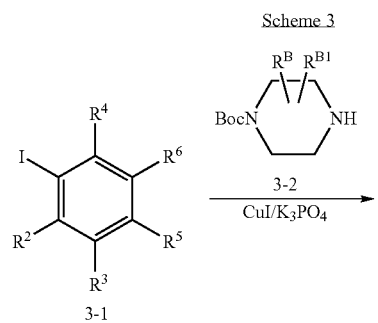

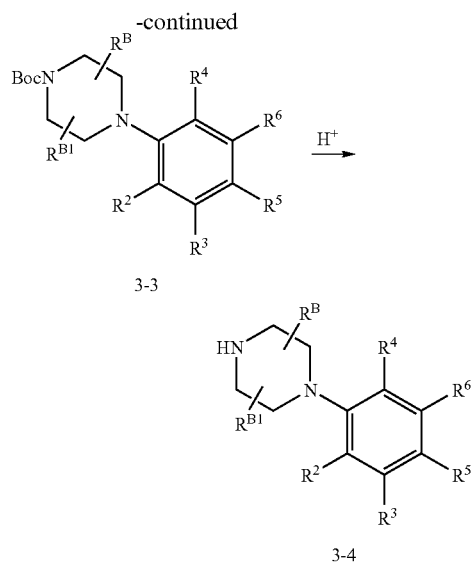

Alternatively, piperazine derivatives (formula 4-3) can be prepared by displacement of a 2-chloropyridine or 2-chloropyrimidine derivative of formula 4-1 with a piperazine derivative of formula 4-2.

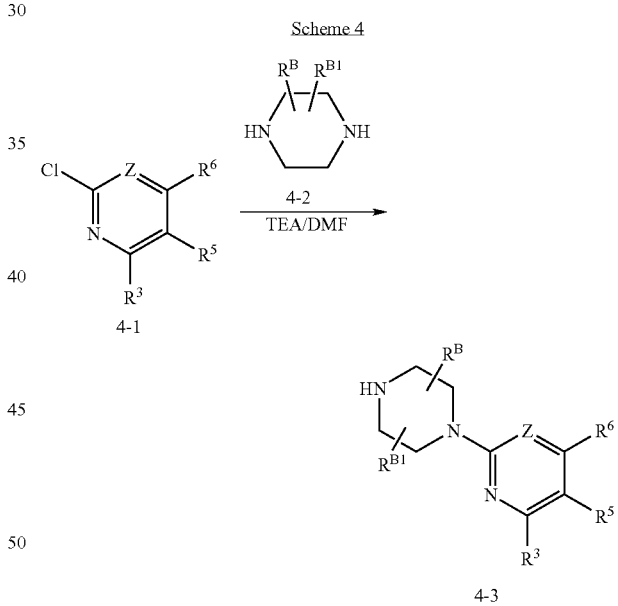

Alternatively, piperazine derivatives can be prepared using a sequence as illustrated in Scheme 5. The commercially available 3,5-dibromopyridine 5-1 can be converted to 3-bromo-5-iodopyridine 5-2 by treatment with isopropylmagnesium bromide and iodine. Coupling of the resulting iodo with a piperazine derivative of formula 3-2 can be accomplished using copper(I) 10 iodide and potassium phosphate. Following conversion of the bromo of the resulting intermediate 5-3 to iodo using isopropylmagnesium bromide and iodine, the iodo can be displaced with trifluoromethyl by treatment with $Me_3SiCF_3$/CuI/KF/DMF to afford the trifluoromethylpyridine derivative of formula 5-5. Removal of the Boc using an acid such as HCl in dioxane or TFA yields the piperazine derivatives of formula 5-6.

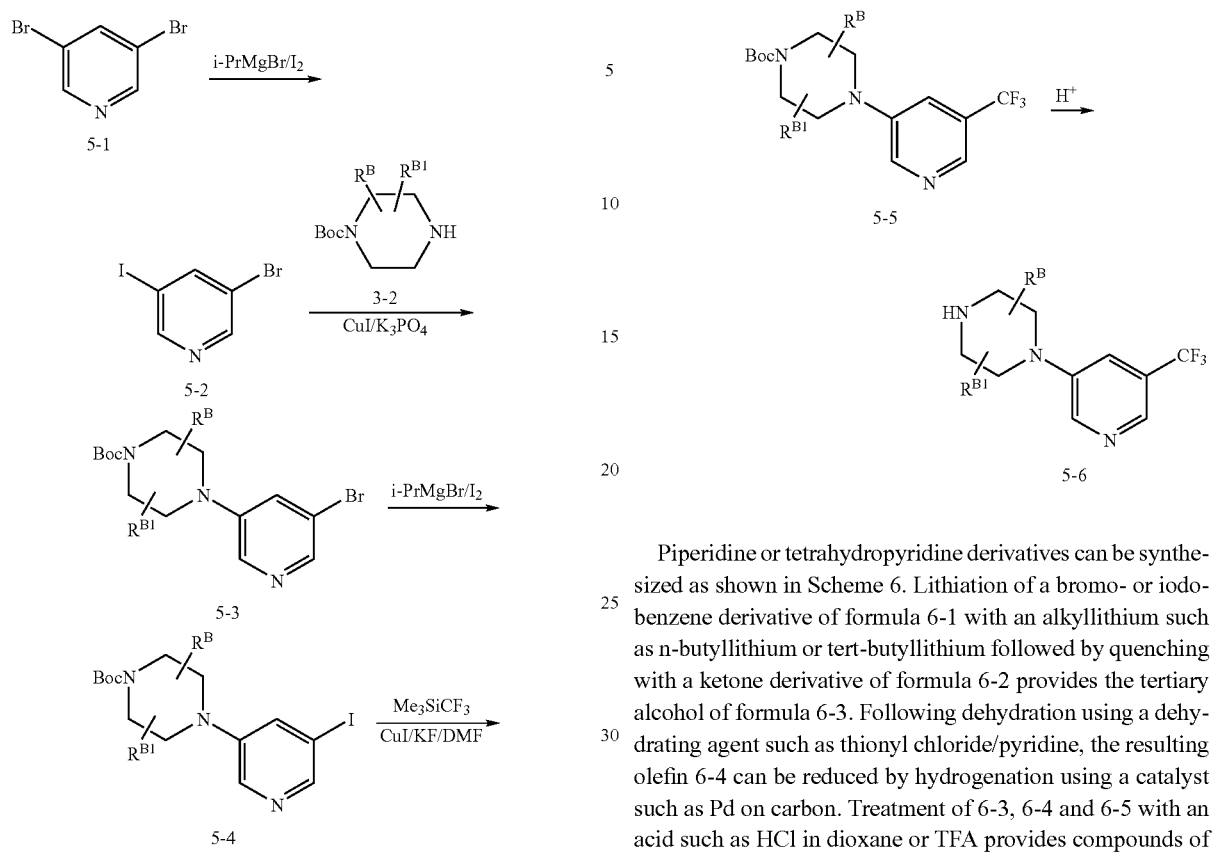

Piperidine or tetrahydropyridine derivatives can be synthesized as shown in Scheme 6. Lithiation of a bromo- or iodo-benzene derivative of formula 6-1 with an alkyllithium such as n-butyllithium or tert-butyllithium followed by quenching with a ketone derivative of formula 6-2 provides the tertiary alcohol of formula 6-3. Following dehydration using a dehydrating agent such as thionyl chloride/pyridine, the resulting olefin 6-4 can be reduced by hydrogenation using a catalyst such as Pd on carbon. Treatment of 6-3, 6-4 and 6-5 with an acid such as HCl in dioxane or TFA provides compounds of formulae 6-6, 6-7 and 6-8.

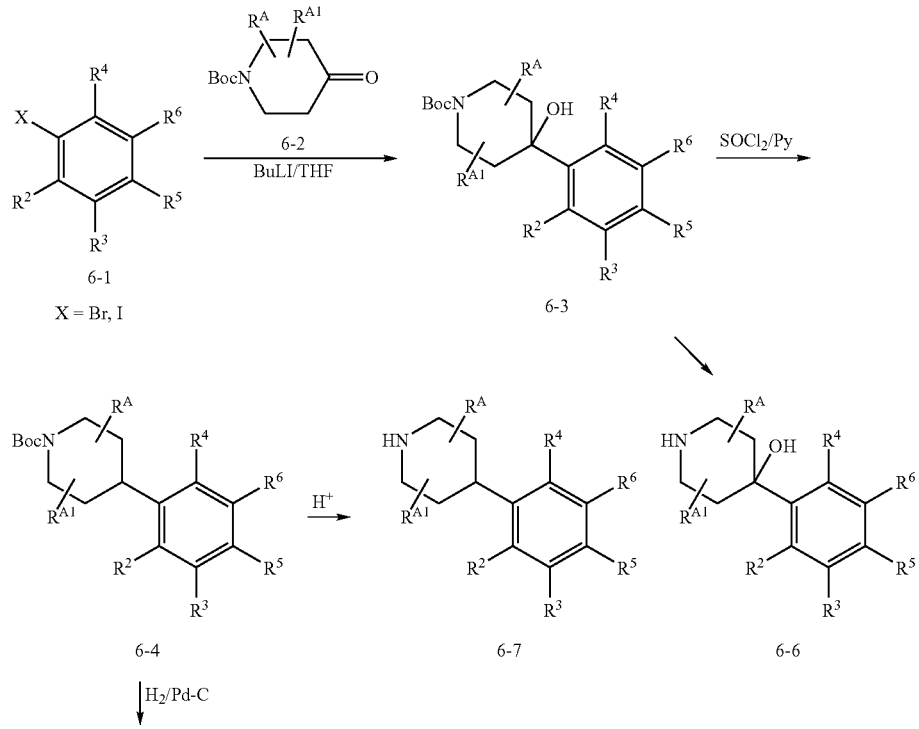

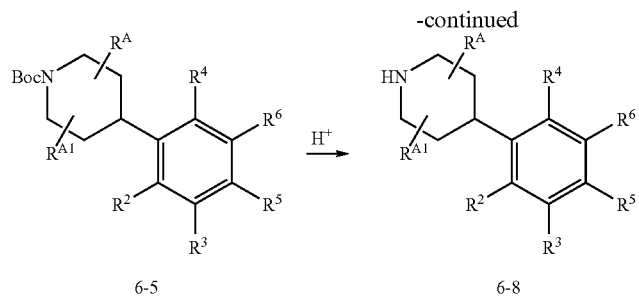

Alternatively, piperidine or tetrahydropyridine derivatives can be synthesized as illustrated in Scheme 7. A commercially available 2-chloropyridine or 2-chloropyrilidine derivative of formula 4-1 can be converted to 2-bromopyridine derivative of formula 7-1 by treatment with BrSiMe₃. Using similar procedures described in Scheme 6, piperidine and tetrahydropyridine derivatives of formula 7-5 and 7-6 can be obtained from 7-1.

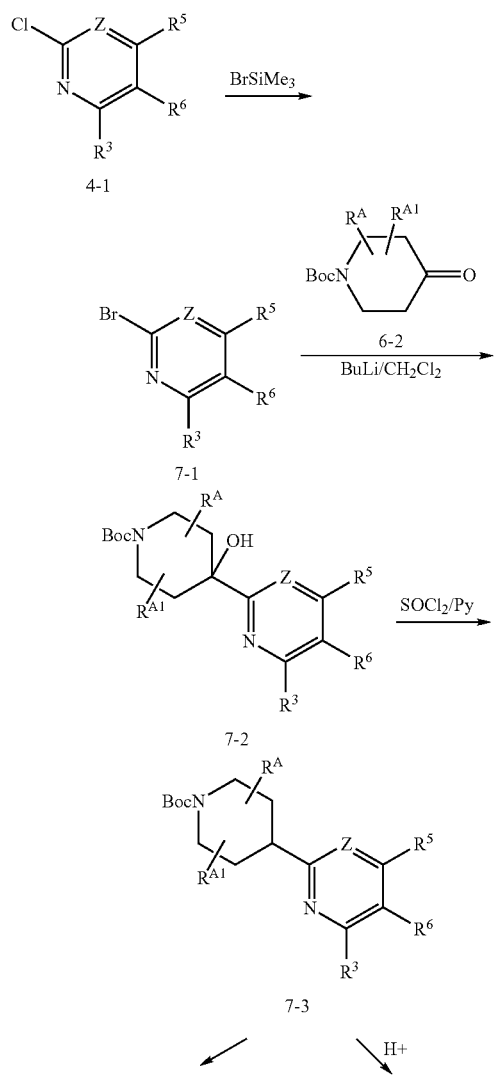

Alternatively, piperidine or tetrahydropyridine derivatives can be synthesized as outlined in Scheme 8. 3-Nitro-5-trifluoromethylpyridin-2-ol can be obtained by nitration of the commercially available 5-trifluoromethylpyridin-2-ol (8-1). Following conversion of the hydroxy group in 8-2 to chloro, the resulting chloro compound 8-3 is subjected to a hydrogenation using a catalyst such as Pd on carbon to give 3-amino-5-trifluoromethylpyridine 8-4. Diazotization of 8-4 using NaNO₂/HBr in the presence of Cu(I)Br provides 3-bromo-5-trifluoromethylpyridine 8-5. Following the procedures described in Scheme 6, 8-5 can be converted to piperidine or tetrahydropyridine derivatives of formulae 8-9 and 8-10.

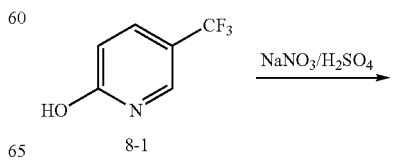

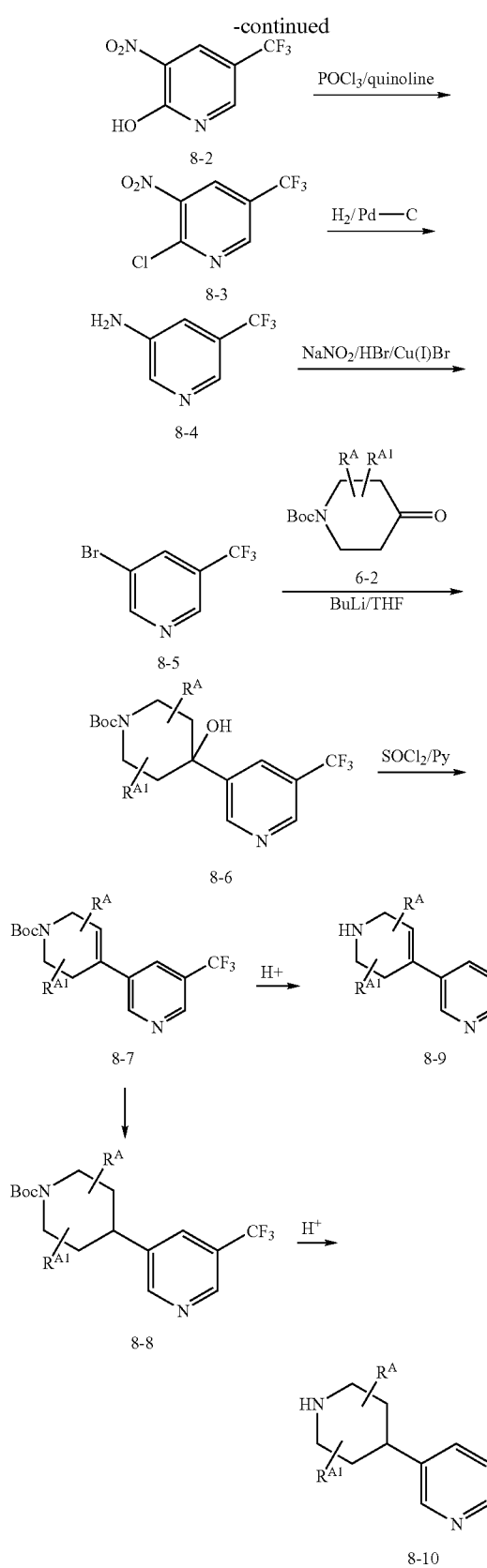

X=Br, I) using n-butyllithium followed by addition of cyclo-hexanedione mono-etheylene ketal (9-1) gives rise to the alcohol intermediate 9-2. Treatment of the ketal 9-2 with aqueous acid yields the ketone product 9-3.

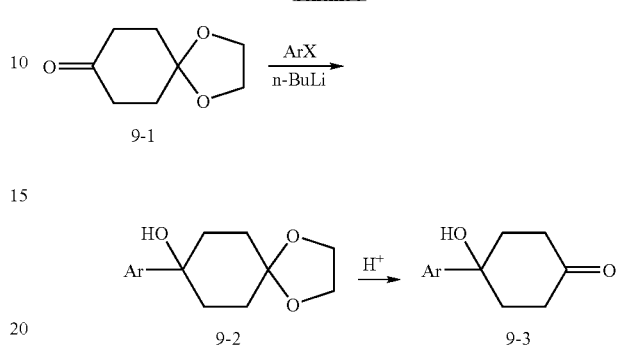

Final compounds of formula I can be assembled using the methods described in Scheme 10. A carboxylic acid of formula 1-5 can be condensed with an amine of formula 10-1 using a standard amide formation agent such as BOP or PyBrop (coupling agent). Following removal of the Boc using an acid such as HCl or TFA, the resulting amine 10-3 can be subjected to alkylation, reductive amination or acylation, etc. to provide final compounds of formula 10-4.

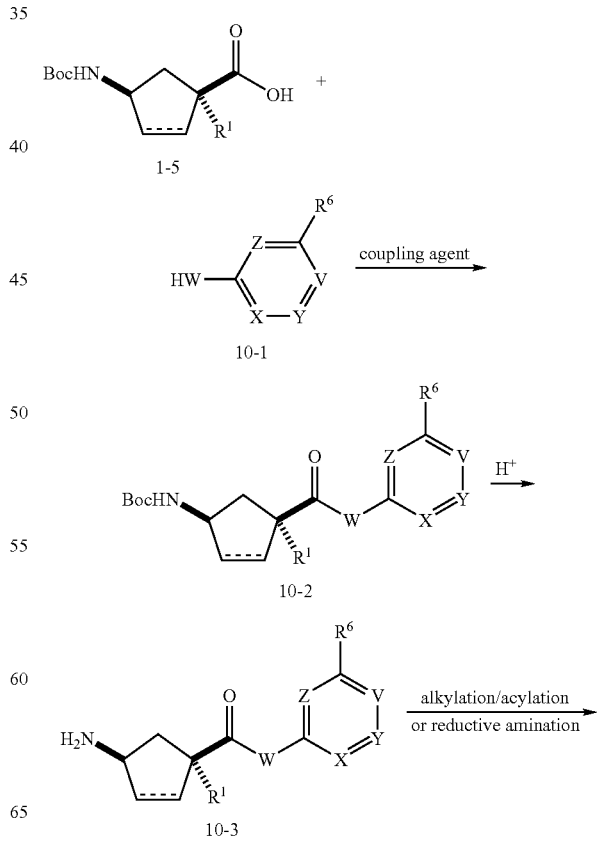

Compounds of formula 9-3 can be prepared according to Scheme 9. Lithiation of arylhalide or heteroarylhalide (ArX,

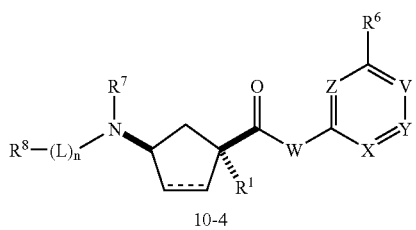
10-4

Alternatively, compounds of the invention can be assembled according to Scheme 11. Coupling of a carboxylic acid of formula 2-5 with an amine of formula 10-1 using a standard amide formation method can produce amides of formula 11-1. Following conversion of the ketal to a ketone using an aqueous acid, reductive amination of the resulting ketone 11-2 with an amine using a reducing agent such as sodium triacertoxyborohydride provides compounds of formula 11-3.

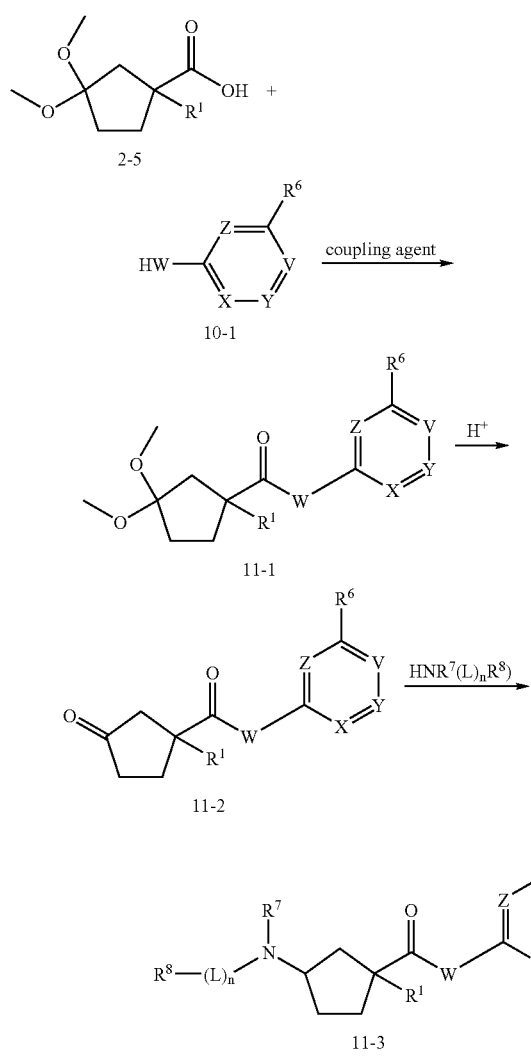

Methods

In some embodiments, compounds of the invention can modulate activity of one or more chemokine receptors. The term "modulate" is meant to refer to an ability to increase or decrease activity of a receptor. Accordingly, compounds of the invention can be used in methods of modulating a chemokine receptor by contacting the receptor with any one or more of the compounds or compositions described herein. In some embodiments, compounds of the present invention can act as inhibitors of chemokine receptors. In further embodiments, the compounds of the invention can be used to modulate activity of a chemokine receptor in an individual in need of modulation of the receptor by administering a modulating amount of a compound of Formula I.

Chemokine receptors to which the present compounds bind and/or modulate include any chemokine receptor. In some embodiments, the chemokine receptor belongs to the CC family of chemokine receptors including, for example, CCR1, CCR2, CCR3, CCR4, CCR5, CCR6, CCR7, CCR8, and CCR10. In some embodiments, the chemokine receptor is CCR2. In some embodiments, the chemokine receptor is CCR5. In some embodiments, the chemokine receptor binds and/or modulates both CCR2 and CCR5.

The compounds of the invention can be selective. By "selective" is meant that a compound binds to or inhibits a chemokine receptor with greater affinity or potency, respectively, compared to at least one other chemokine receptor.

Compounds of the invention can be dual inhibitors or binders of CCR2 and CCR5, meaning that the compounds of the invention can bind to or inhibit both CCR2 and CCR5 with greater affinity or potency, respectively, than for other chemokine receptors such as CCR1, CCR3, CCR4, CCR6, CCR7, CCR8, and CCR10. In some embodiments, the compounds of the invention have binding or inhibition selectivity for CCR2 and CCR5 over any other chemokine receptor. Selectivity can be at least about 10-fold, at least about 20-fold, at least about 50-fold, at least about 100-fold, at least about 200-fold, at least about 500-fold or at least about 1000-fold. Binding affinity and inhibitor potency can be measured according to routine methods in the art, such as according to the assays provided herein.

The present invention further provides methods of treating a chemokine receptor-associated disease or disorder in an individual (e.g., patient) by administering to the individual in need of such treatment a therapeutically effective amount or dose of a compound of the present invention or a pharmaceutical composition thereof. A chemokine receptor-associated disease can include any disease, disorder or condition that is directly or indirectly linked to expression or activity of the chemokine receptor. A chemokine receptor-associated disease can also include any disease, disorder or condition that can be prevented, ameliorated, or cured by modulating chemokine receptor activity. A chemokine receptor-associated disease can further include any disease, disorder or condition that is characterized by binding of an infectious agent such as a virus or viral protein with a chemokine receptor. In some embodiments, the chemokine receptor-associated disease is a CCR5-associated disease such as HIV infection.

Example chemokine receptor-associated diseases, disorders and conditions include inflammation and inflammatory diseases, pain, pain associated with osteoarthritis, pain associated with rheumatoid arthritis, neuropathic pain, cardiovascular diseases, obesity, immune disorders, cancer, liver fibrosis, and viral infections. Example inflammatory diseases include diseases having an inflammatory component such as asthma, seasonal and perennial allergic rhinitis, sinusitis, conjunctivitis, age-related macular degeneration, food allergy, scombroid poisoning, psoriasis, urticaria, pruritus, eczema, inflammatory bowel disease, thrombotic disease, otitis media, liver cirrhosis, cardiac disease, Alzheimer's disease, sepsis, restenosis, atherosclerosis, multiple sclerosis, Crohn's disease, ulcerative colitis, hypersensitivity lung diseases, drug-induced pulmonary fibrosis, chronic obstructive pulmonary disease (COPD), rheumatoid arthritis, and nephritis, ulcerative colitis, atopic dermatitis, stroke, acute nerve injury, sarcoidosis, hepatitis, endometriosis, neuropathic pain, hypersensitivity pneumonitis, eosinophilic pneumonias, delayed-type hypersensitivity, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis), eye disorders (e.g., retinal neurodegeneration, choroidal neovascularization, etc.) and the like. Example immune disorders include rheumatoid arthritis, psoriatic arthritis, systemic lupus erythematosus, myastenia gravis, juvenile onset diabetes; glomerulonephritis, autoimmune throiditis, organ transplant rejection including allograft rejection and graft-versus-host disease. Example cancers include cancers such as breast cancer, ovarian cancer, multiple myeloma and the like that are characterized by infiltration of macrophages (e.g., tumor associated macrophages, TAMs) into tumors or diseased tissues. Example viral infections include Herpes infection, influenza, HIV infection or AIDS.

Further diseases treatable by administration of a compound of the present invention include, for example, autoimmune nephritis, lupus nephritis, Goodpasture's syndrome nephritis and Wegeners granulomatosis nephritis, lupus erythematosus, Goodpasture's syndrome and Wegeners granulomatosis.

As used herein, the term "contacting" refers to the bringing together of indicated moieties in an in vitro system or an in vivo system. For example, "contacting" the chemokine receptor with a compound of the invention includes the administration of a compound of the present invention to an individual or patient, such as a human, having a chemokine receptor, as well as, for example, introducing a compound of the invention into a sample containing a cellular or purified preparation containing the chemokine receptor.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease (non-limiting examples are preventing hypersensitivity lung diseases, drug-induced pulmonary fibrosis, chronic obstructive pulmonary disease (COPD), graft-versus-host disease and/or allograft rejection after transplantation, or preventing allergic reactions such as atopic dermatitis, or seasonal or perennial allergic rhinitis);

(2) inhibiting the disease; for example, inhibiting a disease, condition or disorder in an individual who is experiencing or displaying the pathology or symptomatology of the disease, condition or disorder (i.e., arresting further development of the pathology and/or symptomatology) such as inhibiting the autoimmune response in hypersensitivity lung diseases, drug-induced pulmonary fibrosis, chronic obstructive pulmonary disease (COPD), rheumatoid arthritis, lupus or psoriasis, or inhibiting tumor growth or stabilizing viral load in the case of a viral infection; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the autoimmune response in hypersensitivity lung diseases, drug-induced pulmonary fibrosis, chronic obstructive pulmonary disease (COPD), rheumatoid arthritis, lupus or psoriasis, or shrinking a tumor associated with cancer or lowering viral load in the case of a viral infection.

One or more additional pharmaceutical agents such as, for example, antibodies, anti-inflammatory agents, immunosuppressants, and chemotherapeutics can be used in combination with the compounds of the present invention for treatment of chemokine receptor-associated diseases, disorders or conditions. The agents can be combined with the present compounds in a single dosage form, or the agents can be administered simultaneously or sequentially as separate dosage forms.

One or more additional pharmaceutical agents such as, for example, anti-viral agents, antibodies, anti-inflammatory agents, insulin secretagogues and sensitizers, serum lipid and lipid-carrier modulating agents, and/or immunosuppressants can be used in combination with the compounds of the present invention for treatment of chemokine receptor-associated diseases, disorders or conditions. The agents can be combined with the present compounds in a single or continuous dosage form, or the agents can be administered simultaneously or sequentially as separate dosage forms.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors, entry inhibitors, fusion inhibitors, maturation inhibitors, and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis (POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA).

Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4(1H,3H)-pyrimidinedione); and (+)-calanolide A (NSC-675451) and B.

Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549.

Other antiviral agents include hydroxyurea, ribavirin, IL-2, IL-12, pentafuside, enfuvirtide, C-34, the cyclotriazadisulfonamide CADA, PA-457 and Yissum Project No. 11607.

In some embodiments, anti-inflammatory or analgesic agents contemplated for use in combination with the compounds of the present invention can comprise, for example, an opiate agonist, a lipoxygenase inhibitor such as an inhibitor of 5-lipoxygenase, a cyclooxygenase inhibitor such as a cyclooxygenase-2 inhibitor, an interleukin inhibitor such as an interleukin-1 inhibitor, a TNF inhibitor such as infliximab, etanercept, or adalimumab an NNMA antagonist, an inhibitor of nitric oxide or an inhibitor of the synthesis of nitric oxide, a non-steroidal antiinflammatory agent, or a cytokine-suppressing antiinflammatory agent, for example, such as acetaminophen, aspirin, codeine, fentanyl, ibuprofen, indomethacin, ketodolac, morphine, naproxen, phenacetin, piroxicam, a steroidal analgesic, sufentanyl, sunlindac, tenidap, and the like. Similarly, the instant compounds can be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedfine, or levo-desoxyephedrine; an antfitussive such as codeine, hydrocodone, caramiphen, carbetapentane, or dextramethorphan; a diuretic; and a sedating or non-sedating antihistamine.

In some embodiments, pharmaceutical agents contemplated for use in combination with the compounds of the present invention can comprise but are not limited to (a) VLA-4 antagonists such as those described in U.S. Pat. No. 5,510,332, WO95/15973, WO96/01644, WO96/06108, WO96/20216, WO96/229661, WO96/31206, WO96/4078, WO97/030941, WO97/022897 WO 98/426567 WO98/53814, WO98/53817, WO98/538185, WO98/54207, and WO98/58902; (b) steroids such as beclornethasone, methylpi-ednisolone, betarnethasone, prednisone, dexamethasone, and hydrocortisone; (c) immunosuppressants such as cyclosporin, tacrolimus, raparnycin and other FK506 type immunosuppressants; (d) antihistamines (HI-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilarnine, asternizole, terfenadine, loratadine, cetirizine, fexofenadine, desearboethoxyloratadine, and the like; (e) non-steroidal anti-asthmatics such as terbutaline, metaproterenol, fenoterol, isoethaiine, albuterol, bitolterol, pirbuterol, theophylline, cromolyn sodium, atropine, ipratropium bromide, leukotriene antagonists (e.g., zafirlukast, montelukast, pranlukast, iralukast, pobilukast, SKB-106,203), leukotriene biosynthesis inhibitors (e.g., zileuton, BAY-1005); (f) nonsteroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (e.g., indomethacin, acernetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenarnic acid derivatives (flufenarnic acid, meclofenamic acid, rnefenamic acid, niflumic acid and tolfenarnic acid), biphenylearboxylic acid derivatives (diflunisal and flufenisal), oxicarns (isoxicarn, piroxicam, sudoxicam and tenoxican), salkylates (acetyl salkylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCR-4, CCR1, CCR2, CCR3 and CCR5; (j) cholesterol lowering agents such as HMG-CoA reductase inhibitors (lovastatin, sirrivastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-inflammatory biologic agents such as anti-TNF therapies, anti-IL-1 receptor, CTLA-4Ig, anti-CD20, and anti-VLA4 antibodies; (l) anti-diabetic agents such as insulin, sulfonylureas, biguanides (metformin), U.-glucosidase inhibitors (acarbose) and orlitazones (troglitazone and pioglitazone); (m) preparations of interferon beta (interferon beta-lo., interferon beta-1 P); (n) other compounds such as aminosalkylic acids, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient.

For example, a CCR2 and/or CCR5 antagonist can be used in combination with an anti-inflammatory pharmaceutical agent in the treatment of inflammation, metabolic disease, autoimmune disease, cancer or viral infection to improve the treatment response as compared to the response to the therapeutic agent alone, without exacerbation of its toxic effects. Additive or synergistic effects are desirable outcomes of combining a CCR2 and/or CCR5 antagonist of the present invention with an additional agent. Furthermore, resistance of cancer cells to agents such as dexamethasone can be reversible upon treatment with a CCR2 and/or CCR5 antagonist of the present invention.

Pharmaceutical Formulations and Dosage Forms

When employed as pharmaceuticals, the compounds of Formula I can be administered in the form of pharmaceutical compositions. These compositions can be prepared in a manner well known in the pharmaceutical art, and can be administered by a variety of routes depending upon whether local or systemic treatment is desired and upon the area to be treated. Administration can be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds of Formula I above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compounds or compositions of the invention contain from about 5 to about 50 mg of the active ingredient. One having ordinary skill in the art will appreciate that this embodies compounds or compositions containing from about 5 to about 10, from about 10 to about 15, from about 15 to about 20, from about 20 to about 25, from about 25 to about 30, from about 30 to about 35, from about 35 to about 40, from about 40 to about 45, or from about 45 to about 50 mg of the active ingredient.

In some embodiments, the compounds or compositions of the invention contain from about 50 to about 500 mg of the active ingredient. One having ordinary skill in the art will appreciate that this embodies compounds or compositions containing from about 50 to about 75, from about 75 to about 100, from about 100 to about 125, from about 125 to about 150, from about 150 to about 175, from about 175 to about 200, from about 200 to about 225, from about 225 to about 250, from about 250 to about 275, from about 275 to about 300, from about 300 to about 325, from about 325 to about 350, from about 350 to about 375, from about 375 to about 400, from about 400 to about 425, from about 425 to about 450, from about 450 to about 475, or from about 475 to about 500 mg of the active ingredient.

In some embodiments, the compounds or compositions of the invention contain from about 500 to about 1000 mg of the active ingredient. One having ordinary skill in the art will appreciate that this embodies compounds or compositions containing from about 500 to about 550, from about 550 to about 600, from about 600 to about 650, from about 650 to about 700, from about 700 to about 750, from about 750 to about 800, from about 800 to about 850, from about 850 to about 900, from about 900 to about 950, or from about 950 to about 1000 mg of the active ingredient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 □g/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antibodies, immune suppressants, anti-inflammatory agents, chemotherapeutics, lipid lowering agents, HDL elevating agents, insulin secretagogues or sensitizers, drugs used for the treatment of rheumatoid arthritis and the like.

Rheumatoid Arthritis (RA) Treatment Regimen

Rheumatoid arthritis (RA) patients, treated aggressively with disease modifying agents (methotrexate, antimalarials, gold, penicillamine, sulfasalazine, dapsone, leflunamide, or biologicals), can achieve varying degrees of disease control, including complete remissions. These clinical responses are associated with improvement in standardized scores of disease activity, specifically the ACR criteria which includes: pain, function, number of tender joints, number of swollen joints, patient global assessment, physician global assessment, laboratory measures of inflammation (CRP and ESR), and radiologic assessment of joint structural damage. Current disease-modifying drugs (DMARDs) require continued administration to maintain optimal benefit. Chronic dosing of these agents is associated with significant toxicity and host defense compromise. Additionally, patients often become refractory to a particular therapy and require an alternative regimen. For these reasons, a novel, effective therapy which allows withdrawal of standard DMARDs would be a clinically important advance.

Patients with significant response to anti-TNF therapies (infliximab, etanercept, adalimumab), anti-IL-1 therapy (kinaret) or other disease modifying anti-rheumatic drugs (DMARDs) including but not limited to methotrexate, cyclosporine, gold salts, antimalarials, penicillamine or leflunamide, who have achieved clinical remission of disease can be treated with a substance that inhibits expression and/or activity of CCR2 including, for example, nucleic acids (e.g., antisense or siRNA molecules), proteins (e.g., anti-CCR2 antibodies), small molecule inhibitors (e.g., the compounds disclosed herein and other chemokine receptor inhibitors known in the art).

In some embodiments, the substance that inhibits expression and/or activity of CCR2 is a small molecule CCR2 inhibitor (or antagonist). The CCR2 antagonist can be dosed orally q.d. or b.i.d at a dose not to exceed about 500 mgs a day. The patients can be withdrawn from or have a decrease in the dosage of their current therapy and would be maintained on treatment with the CCR2 antagonist. Treating patients with a combination of CCR2 antagonist and their current therapy can be carried out for, for example, about one to about two days, before discontinuing or dose reducing the DMARD and continuing on CCR2 antagonist.

Advantages of substituting traditional DMARDS with CCR2 antagonists are numerous. Traditional DMARDs have serious cumulative dose-limiting side effects, the most common being damage to the liver, as well as immunosuppressive actions. CCR2 antagonism is expected to have an improved long-term safety profile and will not have similar immunosuppressive liabilities associated with traditional DMARDs. Additionally, the half-life of the biologicals is typically days or weeks, which is an issue when dealing with adverse reactions. The half-life of an orally bioavailable CCR2 antagonist is expected to be on the order of hours so the risk of continued exposure to the drug after an adverse event is very minimal as compared to biological agents. Also, the current biologic agents (infliximab, etanercept, adalimumab, kinaret) are typically given either i.v. or s.c., requiring doctor's administration or patient self-injection. This leads to the possibility of infusion reaction or injection site reactions. These are avoidable using an orally administered CCR2 antagonist.

Diabetes and Insulin Resistance Treatment Regimen

Type 2 diabetes is one of the leading causes of morbidity and mortality in western societies. In the vast majority of patients, the disease is characterized by pancreatic beta-cell dysfunction accompanied by insulin resistance in the liver and in peripheral tissues. Based on the primary mechanisms that are associated with disease, two general classes of oral therapies are available to treat type 2 diabetes: insulin secretagogues (sulfonylureas such as glyburide) and insulin sensitizers (metformin and thiazolidinediones such as rosiglitazone). Combination therapy that addresses both mechanisms has been shown to manage the metabolic defects of this disease and in many instances can be shown to ameliorate the need for exogenous insulin administration. However, with time, insulin resistance often progresses, leading to the need for further insulin supplementation. In addition, a prediabetic state, referred to as the metabolic syndrome, has been demonstrated to be characterized by impaired glucose tolerance, particularly in association with obesity. The majority of patients who develop type 2 diabetes begin by developing insulin resistance, with the hyperglycemia occurring when these patients can no longer sustain the degree of hyperinsulinemia necessary to prevent loss of glucose homeostasis. The onset of the insulin resistance component is highly predictive of disease onset and is associated with an increase in the risk of developing type 2 diabetes, hypertension and coronary heart disease.

One of the strongest correlates of impaired glucose tolerance and of the progression from an insulin resistant state to type 2 diabetes is the presence of central obesity. Most patients with type 2 diabetes are obese and obesity itself is associated with insulin resistance. It is clear that central adiposity is a major risk factor for the development of insulin resistance leading to type 2 diabetes, suggesting that signals from visceral fat contribute to the development of insulin resistant and progression to disease. In addition to the secreted protein factors, obesity induces a cellular inflammatory response in which bone-marrow derived macrophages accumulate in adipose depots, becoming adipose tissue macrophages. Adipose tissue macrophages accumulate in adipose tissue in proportion to measures of adiposity. Tissue infiltrating macrophages are a source of many of the inflammatory cytokines that have been demonstrated to induce insulin resistance in adipocytes.

Adipose tissue produces MCP-1 in proportion to adiposity, suggesting that its activity by signaling through CCR2 also might play an important role in the accumulation of macrophages in adipose tissue. It is unknown whether the MCP-1/CCR2 interaction is directly responsible for monocyte recruitment to adipose tissue, whether reduced recruitment of macrophages to adipose tissue in humans will directly lead to the reduced production of proinflammatory molecules and whether the proinflammatory molecule production is directly linked to insulin resistance.

Patients who demonstrate insulin resistance, either prediabetic (normoglycemic) or diabetic (hyperglycemic), could be treated with a substance that inhibits the expression and/or activity of CCR2 including, for example, nucleic acids (e.g., antisense or siRNA molecules), proteins (e.g., anti-CCR2 antibodies), small molecule inhibitors (e.g., the compounds disclosed herein and other chemokine receptor inhibitors known in the art). In some embodiments, the substance that inhibits expression and/or activity of CCR2 is a small molecule CCR2 inhibitor (or antagonist). The CCR2 antagonist can be dosed orally q.d. or b.i.d at a dose not to exceed about 500 mgs a day. The patients can be withdrawn from or have a decrease in the dosage of their current therapy and would be maintained on treatment with the CCR2 antagonist. Alternately CCR2 antagonist treatment may be used to supplement their current therapy to enhance its effectiveness or to prevent progression to further insulin dependence.

Advantages of substituting or supplementing traditional agents with CCR2 antagonists are numerous. Such agents may be useful, for example, to preclude progression from a prediabetic, insulin resistant state to a diabetic state. Such agents may reduce or replace the need for the use of insulin sensitizers, with their attendant toxicities. Such agents may also reduce the need for, or prolong the period until, exogenous insulin supplementation is required.

Atherosclerosis Treatment Regimen

Atherosclerosis is a condition characterized by the deposition of fatty substances in arterial walls. Plaque encompasses such deposits of fatty substances, cholesterol, cellular waste products, calcium and other substances that build up in the inner lining of an artery. Plaques can grow large enough to significantly reduce the blood's flow through an artery. However, more significant damage occurs when the plaque becomes unstable and ruptures. Plaques that rupture cause blood clots to form that can block blood flow or break off and travel to other parts of the body. If the clot blocks a blood vessel that feeds the heart, it causes a heart attack. If it blocks a blood vessel that feeds the brain, it causes a stroke. Atherosclerosis is a slow, complex disease that typically starts in childhood and often progresses as people grow older.

A high level of cholesterol in the blood is a major risk factor for coronary heart disease. Based on cholesterol as a primary composition of plaque, the advance of plaque formation has been managed by the reduction of circulating cholesterol or by elevation of cholesterol-carrying high density lipoproteins (HDL). Circulating cholesterol can be reduced, for example, by inhibiting its synthesis in the liver using or by reducing update from food. Such medicaments that act through these mechanism may include medicines that are used to lower high cholesterol levels: bile acid absorbers, lipoprotein synthesis inhibitors, cholesterol synthesis inhibitors and fibric acid derivatives. Circulating HDL can additionally be elevated by administration of, for example, probuchol or high doses of niacin. Therapy that addresses multiple mechanisms has been shown to slow disease progression and progression to plaque rupture.

Atherosclerosis is typically accompanied by a cellular inflammatory response in which bone-marrow derived macrophages accumulate in fatty streaks along the vessel wall, becoming foam cells. Foam cells are a source of many of the inflammatory cytokines that have been demonstrated to induce plaque progression and of the enzymes that can promote plaque destabilization. Atherosclerotic tissue also produces MCP-1, suggesting that its activity by signaling through CCR2 also might play an important role in the accumulation of macrophages as foam cells in plaques. CCR2−/− mice have been demonstrated to have significantly reduced macrophages in fatty streaks generated as a result of high fat diet or genetic alteration in lipid metabolism.

Patients who demonstrate high circulating cholesterol, low HDL, or elevated circulating CRP or present with vessel wall plaque by imaging, or any other evidence of the presence of atherosclerosis could be treated with a substance that inhibits the expression and/or activity of CCR2 including, for example, nucleic acids (e.g., antisense or siRNA molecules), proteins (e.g., anti-CCR2 antibodies), small molecule inhibitors (e.g., the compounds disclosed herein and other chemokine receptor inhibitors known in the art). In some embodiments, the substance that inhibits expression and/or activity of CCR2 is a small molecule CCR2 inhibitor (or antagonist) such as a compound of the invention. The CCR2 antagonist can be dosed orally q.d. or b.i.d at a dose not to exceed about 500 mgs a day. The patients can be withdrawn from or have a decrease in the dosage of their current therapy and would be maintained on treatment with the CCR2 antagonist. Alternately CCR2 antagonist treatment may be used to supplement their current therapy to enhance its effectiveness in, for example, preventing plaque progression, stabilizing plaque that has already formed or inducing plaque regression.

Advantages of substituting or supplementing traditional agents with CCR2 antagonists are numerous. Such agents may be useful, for example, to preclude progression of the plaque to a stage of instability with its associated risk of plaque rupture. Such agents may reduce or replace the need for the use of cholesterol modifying drugs or HDL elevating drugs, with their attendant toxicities including, but not limited to, flushing, liver damage and muscle damage such as myopathy. Such agents may also reduce the need for, or prolong the period until, surgery is required to open the vessel wall or until use of anticoagulants is required to limit damage due to potential plaque rupture.

Labeled Compounds and Assay Methods

Another aspect of the present invention relates to fluorescent dye, spin lable, heavy metal or radio-labeled compounds of Formula I that would be useful not only in imaging but also in assays, both in vitro and in vivo, for localizing and quantitating the chemokine receptor in tissue samples, including human, and for identifying chemokine receptor ligands by inhibition binding of a labeled compound. Accordingly, the present invention includes chemokine receptor assays that contain such labeled compounds.

The present invention further includes isotopically-labeled compounds of Formula I. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{80}$O, $^{18}$F, $^{35}$S, $^{36}$Cl, $^{82}$Br, $^{75}$Br, $^{76}$Br, $^{77}$Br, $^{123}$I, $^{224}$I, $^{125}$I and $^{131}$I. The radionuclide that is incorporated in the instant radiolabeled compounds will depend on the specific application of that radio-labeled compound. For example, for in vitro chemokine receptor labeling and competition assays, compounds that incorporate $^3$H, $^{14}$C, $^{82}$Br, $^{125}$I, $^{132}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

Synthetic methods for incorporating radio-isotopes into organic compounds are applicable to compounds of the invention and are well known in the art. A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the chemokine receptor. Accordingly, the ability of a test compound to compete with the radio-labeled compound for binding to the chemokine receptor directly correlates to its binding affinity.

Kits

The present invention also includes pharmaceutical kits useful, for example, in the treatment or prevention of chemokine-associated diseases which include one or more containers containing a pharmaceutical composition comprising a therapeutically effective amount of a compound of Formula I. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

PREPARATIONS AND EXAMPLES

The compounds of the Preparations and Examples can be prepared according to the methods described herein and/or according to routine synthetic methods. Example methods can be found in, for example, U.S. Ser. Nos. 11/167,329 and 11/167,816, both filed Jun. 27, 2005, as well as WO 2005/067502, each of which is incorporated herein by reference in its entirety. Further, the compounds of the Examples can be tested for inhibitory activity of CCR2 or other chemokines according any one or more of the assays described herein or are known in the art.

Preparation 1

(3S)-3-isopropyl-3-({4-[4-(trifluoromethyl)pyridin-2-yl]piperazin-1-yl}carbonyl)cyclopentanone

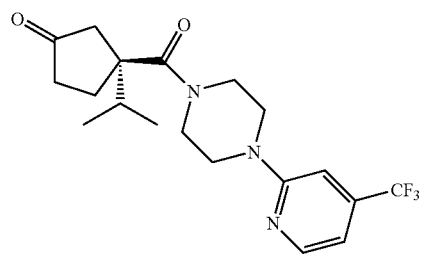

step A:

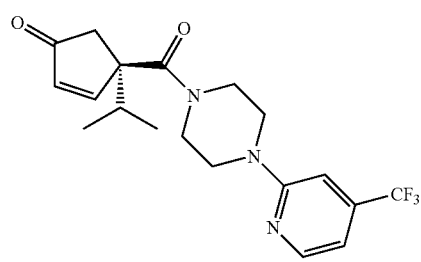

A solution of (1S,4S)-4-isopropyl-4-(4-[4-(trifluoromethyl)pyridin-2-yl]piperazin-1-ylcarbonyl)cyclopent-2-en-1-amine (3.5 g, 9.2 mmol) and 3,5-Cyclohexadiene-1,2-dione, 3,5-bis(1,1-dimethylethyl)-(2.20 g, 9.99 mmol) in Methanol (85 mL) was stirred at room temperature for 30 minutes. Tetrahydrofuran (85 mL) and 1N HCl (10 mL) were added and the resulting mixture was stirred overnight at room temperature. The mixture was diluted with water and the organics evaporated. The remaining aqueous was made basic with 1N NaOH and extracted with EtOAc three times. The combined extracts were dried (Magnesium sulfate), filtered, and concentrated in vacuo. The crude residue was purified by flash column chromatography (1:1 EtOAc/Hexanes) to yield (3.16 g, 90%) of the title compound. MS calculated for $C_{19}H_{22}F_3N_3O_2$: (M+H) 382; found 382.1.

Step B:

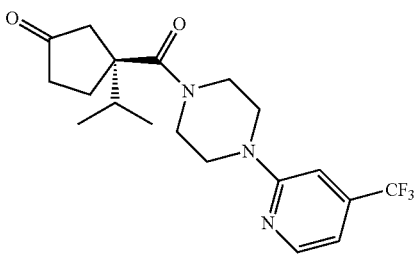

A mixture of the product from Step A (3.15 g, 8.26 mmol), palladium on carbon (10%, 632 mg), triethylamine (1.2 ml, 8.26 mmol), and methanol (32 ml) was hydrogenated at 40 psi for 90 minutes. The mixture was filtered through Celite, washing with DCM. The filtrates were concentrated in vacuo to afford 3.0 g (96%) of the title compound as a tan solid. MS calculated for $C_{19}H_{24}F_3N_3O_2$: (M+H) 384; found 384.1.

Preparation 1A (3S)-3-isopropyl-3-({4-[4-(trifluoromethyl)pyridin-2-yl]piperazin-1-yl}carbonyl)cyclopentanone

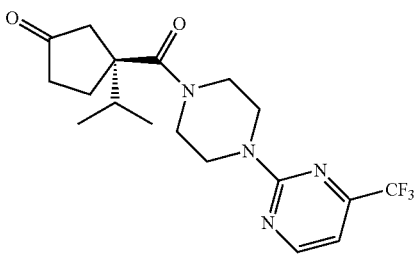

The title compound was prepared in a fashion similar to that for Preparation 1 starting from (1S,4S)-4-isopropyl-4-(4-[4-(trifluoromethyl)pyrimidin-2-yl]piperazin-1-ylcarbonyl)cyclopent-2-en-1-amine. MS calculated for $C_{18}H_{23}F_3N_4O_2$: (M+H) 385; found 385.1.

Example 1

4-{[(1R3S)-3-isopropyl-3-({4-[4-(trifluoromethyl)pyridin-2-yl]piperazin-1-yl}carbonyl)cyclopentyl]amino}-1-(5-pyrimidin-2-ylpyridin-2-yl)cyclohexanol

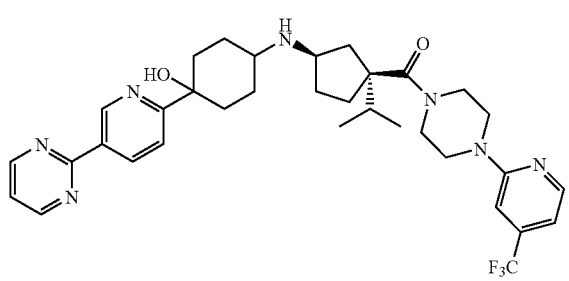

To a solution of ((1S,3R)-3-amino-1-isopropylcyclopentyl)(4-(4-(trifluoromethyl)pyridin-2-yl)piperazin-1-yl) methanone (50 mg, 0.13 mmol) in DCM (2 mL) was added 4-hydroxy-4-(5-(pyrimidin-2-yl)pyridin-2-yl)cyclohexanone (1.5 equiv) and sodium triacetoxyborohydride (1.5 equiv). The mixture was stirred until complete, portioned and the aqueous phase extracted with ethyl acetate. The combined organic layers were dried over sodium sulfate. Chromatography gave the title compound as a white powder after lypholization. MS calculated for $C_{32}H_{42}F_3N_7O_2$: (M+H) 638; found 638.3.

Example 2 ethyl 4-{[(1R3S)-3-isopropyl-3-({4-[4-(trifluoromethyl)pyridin-2-yl]piperazin-1-yl}carbonyl)cyclopentyl]amino}-3-methoxypiperidine-1-carboxylate

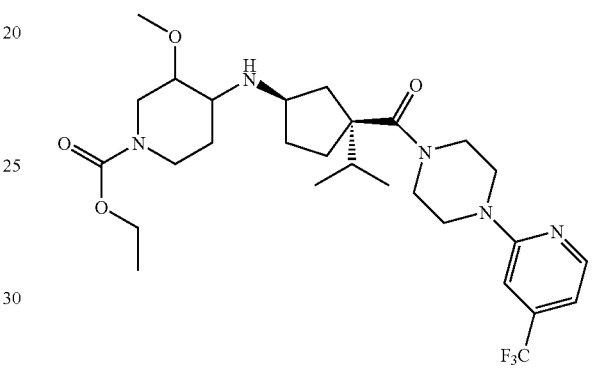

A. Preparation of tert-butyl 3-hydroxy-4,4-dimethoxypiperidine-1-carboxylate

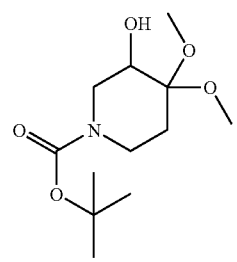

The title compound was prepared by taking tert-Butyl 4-Oxo-1-piperidinecarboxylate (2 g, 0.01 mol) in Methanol (19 mL, 0.47 mol) and adding Potassium hydroxide (1.3 g, 0.024 mol;) at 0° C. To this mixture was added Iodine (2.8 g, 0.011 mol) in Methanol (21 mL, 0.52 mol) dropwise over 30 min to keep the internal temperature close to 0° C. The reaction was then allowed to warm to ambient temperature for 2 h. The reaction was then concentrated in vacuo and the residue was dissolved in toluene (20 mL) and filtered. The filtrate was purified via flash chromatography to afford an oil (1.8 g, 70%) which has the same NMR as described in Zacuto, Michael J.; Cai, Dongwei., Tetrahedron Letters, 2005, 46(3), 447-450.
$^1$H NMR (CD3OD, 400 MHz) d 4.06-4.00 (m, 1H), 3.99-3.91 (m, 1H), 3.80-3.73 (m, 1H), 3.29 (s, 3H), 3.28 (s, 3H), 3.22-3.10 (br m, 1H), 2.95-2.80 (br m, 1H), 1.91-1.77 (m, 2H), 1.50 (s, 9H).

B. Preparation of tert-butyl 3,4,4-trimethoxypiperidine-1-carboxylate

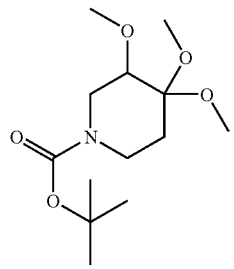

The title compound was prepared by taking tert-butyl 3-hydroxy-4,4-dimethoxypiperidine-1-carboxylate (702 mg, 0.00269 mol) in Tetrahydrofuran (10 mL, 0.1 mol) at 0° C. and adding in Potassium tert-butoxide (15 mL, 0.015 mol). The reaction was stirred for 20 min and then Dimethyl sulfate (0.56 mL, 0.006 mol) was added and the temperature raised to ambient temperature. After stirring overnight the reaction mixture was poured into water and ethyl acetate. The organic layers were separated, dried and concentrated in vacuo to afford an oil which was used as-is (424 mg, 99%) MS calculated for $C_{13}H_{25}NO_5$: (M+H) 276; found 276.1.

C. Preparation of 3,4,4-trimethoxypiperidine

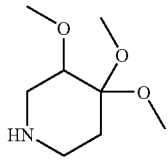

The title compound was prepared by taking tert-butyl 3,4,4-trimethoxypiperidine-1-carboxylate (424 mg, 0.00154 mol) in Methylene chloride (10 mL, 0.2 mol) and adding Trifluoroacetic Acid (1 mL, 0.02 mol). The reaction was stirred for 3 h. The solvent was removed in vacuo and the crude taken to the next step (270 mg, 99%). MS calculated for $C_8H_{17}NO_3$: (M+H) 176; found 176.1.

D. Preparation of ethyl 3,4,4-trimethoxypiperidine-1-carboxylate

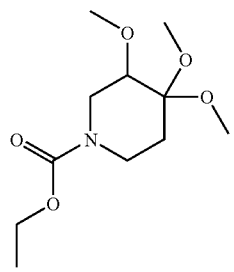

The title compound was prepared by taking 3,4,4-trimethoxypiperidine (150 mg, 0.00086 mol) in Methylene chloride (10 mL, 0.2 mol) and adding Ethyl chloroformate (0.098 mL, 0.0010 mol) and Triethylamine (0.24 mL, 0.0017 mol). The reaction was stirred overnight and then quenched with $NaHCO_3$. The crude was obtained by evaporating the organic layer and was taken to the next step as-is (210 mg, 99%). MS calculated for $C_{11}H_{21}NO_5$: (M+H) 248; found 248.1.

E. Preparation of ethyl 3-methoxy-4-oxopiperidine-1-carboxylate

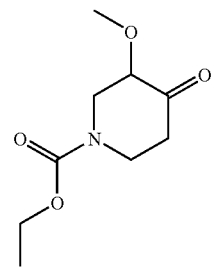

The title compound was prepared by taking 3,4,4-trimethoxypiperidine-1-carboxylate (210 mg, 0.00085 mol) in Methanol (5 mL, 0.1 mol) and adding 4 M of Hydrogen chloride in 1,4-dioxane (5 mL). The reaction was allowed to stir for 4 h at ambient temperature. The residue obtained by removing the solvent in vacuo was used in the next step as-is (170 mg, 99%). MS calculated for $C_9H_{15}NO_4$: (M+H) 202; found 202.1.

F. Preparation of ethyl 4-{[(1S,4S)-4-isopropyl-4-({4-[4-(trifluoromethyl)pyridin-2-yl]piperazin-1-yl}carbonyl)cyclopent-2-en-1-yl]amino}-3-methoxypiperidine-1-carboxylate

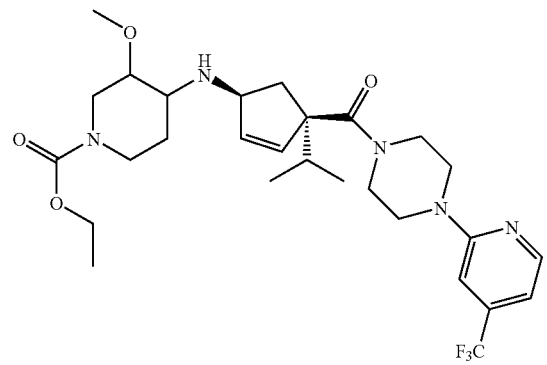

The title compound was prepared by taking ethyl 3-methoxy-4-oxopiperidine-1-carboxylate (148 mg, 0.000737 mol) in Methylene chloride (3 mL, 0.04 mol) and adding (1S,4S)-4-isopropyl-4-({4-[4-(trifluoromethyl)pyridin-2-yl]piperazin-1-yl}carbonyl)cyclopent-2-en-1-amine (0.31 g, 0.00081 mol;), Triethylamine (0.8 mL, 0.006 mol;) and Sodium triacetoxyborohydride (0.312 g, 0.00147 mol). The reaction was stirred overnight. The reaction was quenched with (20 mL) NaOH and extracted with (3×10 mL) $CH_2Cl_2$. The organic layers were collected, dried over $MgSO_4$ and concentrated in vacuo. The crude was taken on to the next step as-is (410 mg, 98%). MS calculated for $C_{28}H_{40}F_3N_5O_4$: (M+H) 568; found 568.1.

G. Preparation of 4-{[(1R3S)-3-isopropyl-3-({4-[4-(trifluoromethyl)pyridin-2-yl]piperazin-1-yl}carbonyl)cyclopentyl]amino}-1-(5-pyrimidin-2-ylpyridin-2-yl)cyclohexanol

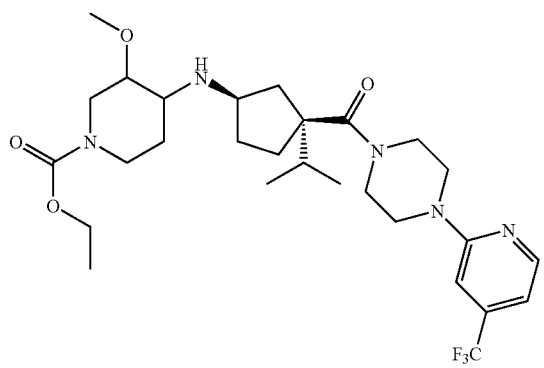

The title compound was prepared taking ethyl 4-{[(1S,4S)-4-isopropyl-4-({4-[4-(trifluoromethyl)pyridin-2-yl]piperazin-1-yl}carbonyl)cyclopent-2-en-1-yl]amino}-3-methoxypiperidine-1-carboxylate (410 mg, 0.00072 mol) in Methanol (10 mL, 0.3 mol) and Palladium Hydroxide (1:4, Palladium hydroxide:Tetracarbon, 150 mg). The reaction mixture was pressurized to 52 PSI and shaken for 4 hrs. The solvent was removed and the material purified via prep LCMS to afford the set of diastereomers as a white powder after lypholization (120 mg, 29%). MS calculated for $C_{28}H_{42}F_3N_5O_4$: (M+H) 570; found 570.1.

Example 3

Methyl 4-{[(1R3S)-3-isopropyl-3-({4-[4-(trifluoromethyl)pyridin-2-yl]piperazin-1-yl}carbonyl)cyclopentyl]amino}-3-methoxypiperidine-1-carboxylate

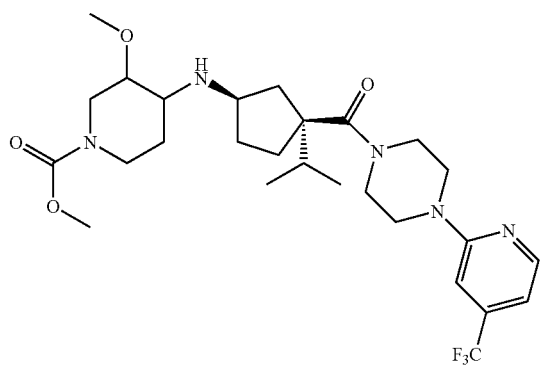

The title compound was prepared in a fashion similar to that for Example 2 starting from methyl 3,4,4-trimethoxypiperidine-1-carboxylate (150 mg, 0.00086 mol) to afford the desired compounds as white powder after lypholization (100 mg, 20%). MS calculated for $C_{27}H_{40}F_3N_5O_4$: (M+H) 556; found 556.1.

Example 4

((1S,3R)-3-(3-oxa-bicyclo[3.3.1]nonan-9-ylamino)-1-isopropylcyclopentyl)(4-(4-(trifluoromethyl)pyridin-2-yl)piperazin-1-yl)methanone

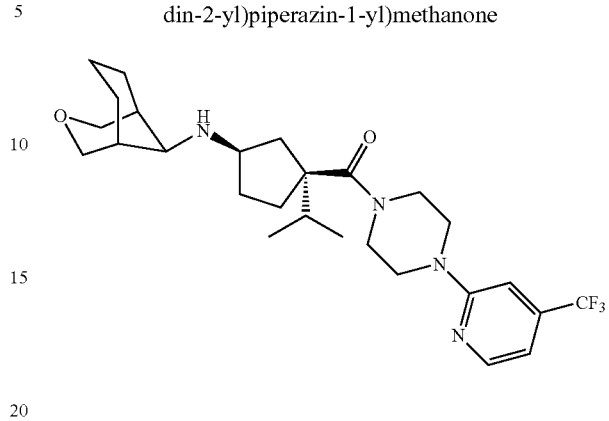

The title compound was prepared in a fashion similar to that for Example 1 employing, in the reductive alkylation, 3-oxabicyclo[3.3.1]non-5-en-9-one, followed by hydrogenation of with Pd/C (5%) in Ethyl Acetate. MS calculated for $C_{28}H_{34}F_3N_5O_3$: (M+H) 509.3025; found 509.2.

Example 5

(1R,3S)-N-[(5-chloro-2-thienyl)methyl]-3-isopropyl-3-({4-[4-(trifluoromethyl)pyridin-2-yl]piperazin-1-yl}carbonyl)cyclopentanamine

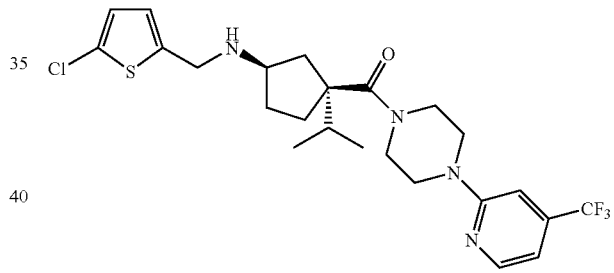

The title compound was prepared in a fashion similar to that for Example 1 employing, in the reductive alkylation, 5-chlorothiophene-2-carbaldehyde. MS calculated for $C_{24}H_{30}ClF_3N_4OS$: (M+H) 515.1781; found 515.185.

Example 6

(1R,3S)-3-isopropyl-N-[(1-pyridin-3-yl-1H-pyrrol-2-yl)methyl]-3-({4-[4-(trifluoromethyl)pyridin-2-yl]piperazin-1-yl}carbonyl)cyclopentanamine

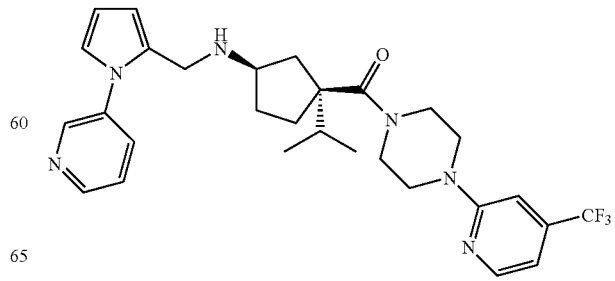

The title compound was prepared in a fashion similar to that for Example 2 employing, in the reductive alkylation, 1-(pyridin-3-yl)-1H-pyrrole-2-carbaldehyde. MS calculated for $C_{29}H_{35}F_3N_6O$: (M+H) 541.2824.

Example 7

(1R,3S)-N-[(1-ethyl-1H-pyrazol-4-yl)methyl]-3-isopropyl-3-({4-[4-(trifluoromethyl)pyridin-2-yl]piperazin-1-yl}carbonyl)cyclopentanamine

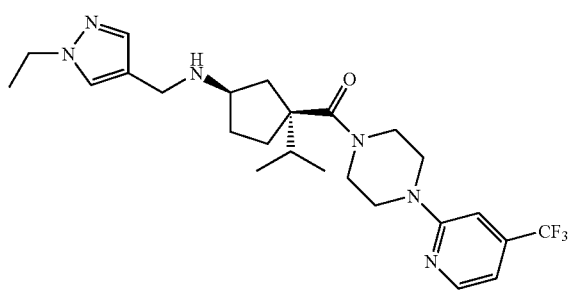

The title compound was prepared in a fashion similar to that for Example 2 employing, in the reductive alkylation, 1-ethyl-1H-pyrazole-4-carbaldehyde. MS calculated for $C_{25}H_{35}F_3N_6O$: (M+H) 493.2824; found 493.2997.

Example 8

(1R,3S)-3-isopropyl-N-(quinolin-6-ylmethyl)-3-({4-[4-(trifluoromethyl)pyridin-2-yl]piperazin-1-yl}carbonyl)cyclopentanamine

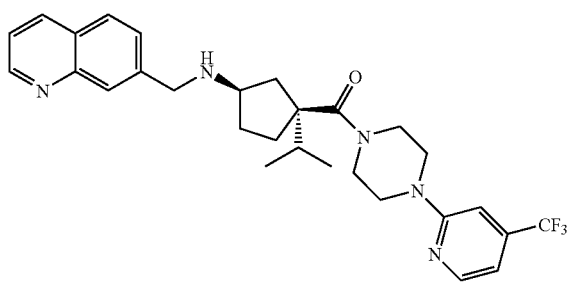

The title compound was prepared in a fashion similar to that for Example 2 employing, in the reductive alkylation, quinoline-7-carbaldehyde. MS calculated for $C_{29}H_{34}F_3N_5O$: (M+H) 526.2715; found 526.2792.

Example 9

7-({[(1R,3S)-3-isopropyl-3-({4-[4-(trifluoromethyl)pyridin-2-yl]piperazin-1-yl}carbonyl)cyclopentyl]amino}methyl)-1H-pyrido[23-b][14]oxazin-2(3H)-one

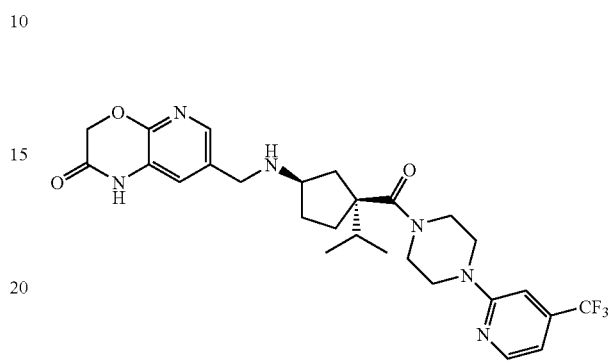

The title compound was prepared in a fashion similar to that for Example 2 employing, in the reductive alkylation, 2-oxo-2,3-dihydro-1H-pyrido[2,3-b][1,4]oxazine-7-carbaldehyde. MS calculated for $C_{27}H_{33}F_3N_6O_3$: (M+H) 547.2566; found 547.2681.

Example 10

(1R,3S)-N-(24-dimethoxybenzyl)-3-isopropyl-3-({4-[4-(trifluoromethyl)pyridin-2-yl]piperazin-1-yl}carbonyl)cyclopentanamine

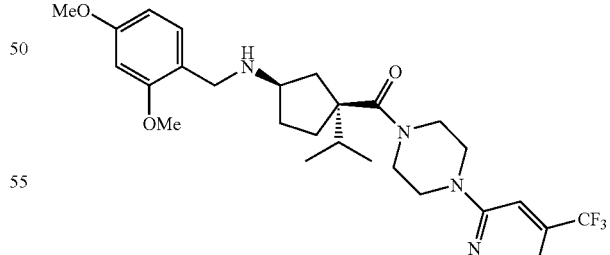

The title compound was prepared in a fashion similar to that for Example 2 employing, in the reductive alkylation, 2,4-dimethoxybenzaldehyde. MS calculated for $C_{28}H_{37}F_3N_4O_3$: (M+H) 535.2818; found 535.2701.

Example 11

N-[(1R,3S)-3-isopropyl-3-({4-[4-(trifluoromethyl)pyridin-2-yl]piperazin-1-yl}carbonyl)cyclopentyl]-1-pyrimidin-2-ylpiperidin-3-amine

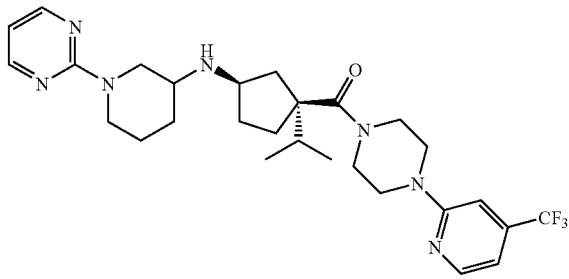

The title compound, as a mixture of diastereomers, was prepared in a fashion similar to that for Example 2 employing, in the reductive alkylation, 1-(pyrimidin-2-yl)piperidin-3-one. MS calculated for $C_{28}H_{38}F_3N_7O$: (M+H) 546.309; found 546.3195.

Example 12

1-but-2-yn-1-yl-5-{[(1R,3S)-3-isopropyl-3-({4-[4-(trifluoromethyl)pyridin-2-yl]piperazin-1-yl}carbonyl)cyclopentyl]amino}azepan-2-one

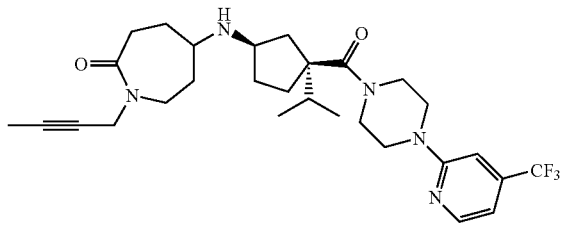

The title compound, as a mixture of diastereomers, was prepared in a fashion similar to that for Example 2 employing, in the reductive alkylation, 1-(but-2-ynyl)azepane-2,5-dione. MS calculated for $C_{29}H_{40}F_3N_5O_2$: (M+H) 548.3134; found 548.3223.

Example 13

N-isopropyl-3-(2-{[(1R,3S)-3-isopropyl-3-({4-[4-(trifluoromethyl)pyridin-2-yl]piperazin-1-yl}carbonyl)cyclopentyl]amino}cyclopentyl)propanamide

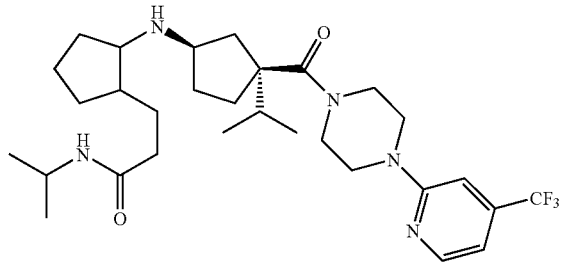

The title compound, as a mixture of diastereomers, was prepared in a fashion similar to that for Example 2 employing, in the reductive alkylation, N-isopropyl-3-(2-oxocyclopentyl)propanamide. MS calculated for $C_{30}H_{46}F_3N_5O_2$: (M+H) 566.3604; found 566.3769.

Example 14

N-[(1R,3S)-3-isopropyl-3-({4-[4-(trifluoromethyl)pyridin-2-yl]piperazin-1-yl}carbonyl)cyclopentyl]indan-2-amine

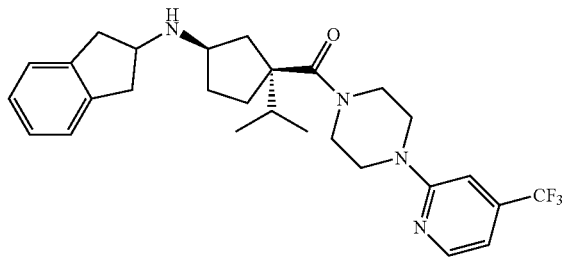

The title compound was prepared in a fashion similar to that for Example 2 employing, in the reductive alkylation, 1H-inden-2(3H)-one. MS calculated for $C_{28}H_{35}F_3N_4O$: (M+H) 501.2763; found 501.2851.

Example 15

N-[(1R-3S)-3-isopropyl-3-({4-[4-(trifluoromethyl)pyridin-2-yl]piperazin-1-yl}carbonyl)cyclopentyl]tetrahydro-2H-thiopyran-4-amine 11-dioxide

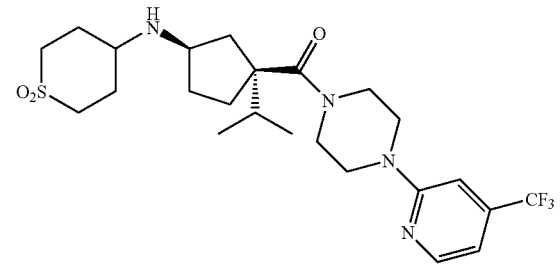

The title compound was prepared in a fashion similar to that for Example 2 employing, in the reductive alkylation, tetrahydro-4H-thiopyran-4-one 1,1-dioxide. MS calculated for $C_{24}H_{35}F_3N_4O_3S$: (M+H) 517.2382; found 517.2496.

Example 16

(1R,3S)-N-cyclopentyl-3-isopropyl-3-({4-[4-(trifluoromethyl)pyridin-2-yl]piperazin-1-yl}carbonyl)cyclopentanamine

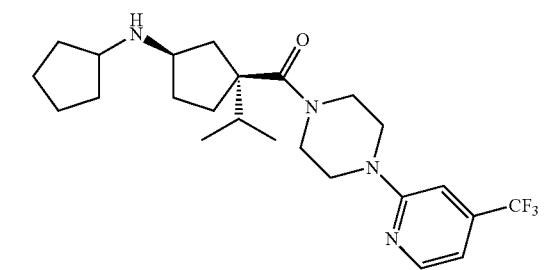

The title compound was prepared in a fashion similar to that for Example 2 employing, in the reductive alkylation, cyclopentanone. MS calculated for $C_{24}H_{35}F_3N_4O$: (M+H) 453.2763; found 453.2859.

Example 17

3-(2-{[(1R,3S)-3-isopropyl-3-({4-[4-(trifluoromethyl)pyridin-2-yl]piperazin-1-yl}carbonyl)cyclopentyl]amino}cyclopentyl)-N-propylpropanamide

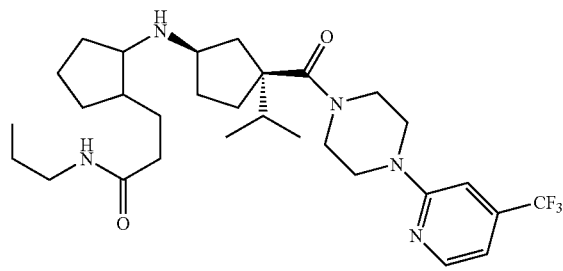

The title compound, as a mixture of diastereomers, was prepared in a fashion similar to that for Example 2 employing, in the reductive alkylation, 3-(2-oxocyclopentyl)-N-propylpropanamide. MS calculated for $C_{30}H_{46}F_3N_5O_2$: (M+H) 566.3604; found 566.3762.

Example 18

6,8-difluoro-N-[(1R,3S)-3-isopropyl-3-({4-[4-(trifluoromethyl)pyridin-2-yl]piperazin-1-yl}carbonyl)cyclopentyl]-1234-tetrahydronaphthalen-2-amine

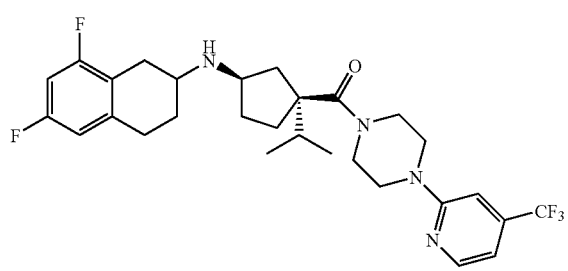

The title compound, as a mixture of diastereomers, was prepared in a fashion similar to that for Example 2 employing, in the reductive alkylation, 6,8-difluoro-3,4-dihydronaphthalen-2(1H)-one. MS calculated for $C_{29}H_{35}F_5N_4O$: (M+H) 551.2731; found 551.2922.

Example 19

N-[(1R,3S)-3-isopropyl-3-({4-[4-(trifluoromethyl)pyridin-2-yl]piperazin-1-yl}carbonyl)cyclopentyl]-1234-tetrahydronaphthalen-2-amine

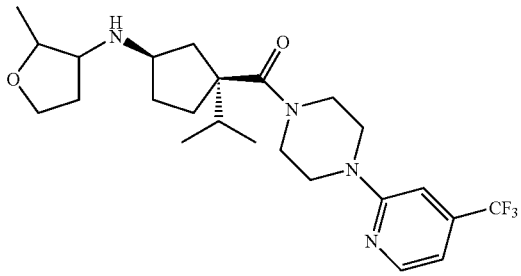

The title compound, as a mixture of diastereomers, was prepared in a fashion similar to that for Example 2 employing, in the reductive alkylation, 3,4-dihydronaphthalen-2(1H)-one. MS calculated for $C_{29}H_{37}F_3N_4O$: (M+H) 515.2919; found 515.2982.

Example 20

2,5-anhydro-1,3,4-trideoxy-3-{[(1R,3S)-3-isopropyl-3-({4-[4-(trifluoromethyl)pyridin-2-yl]piperazin-1-yl}carbonyl)cyclopentyl]amino}pentitol The title compound, as a mixture of diastereomers, was prepared in a fashion similar to that for Example 2 employing, in the reductive alkylation, 2-methyl-dihydrofuran-3(2H)-one. MS calculated for $C_{24}H_{35}F_3N_4O_2$: (M+H) 469.2712; found 469.2931.

Example 21

N-[(1R,3S)-3-isopropyl-3-({4-[4-(trifluoromethyl)pyridin-2-yl]piperazin-1-yl}carbonyl)cyclopentyl]-35-dimethyltetrahydro-2H-pyran-4-amine

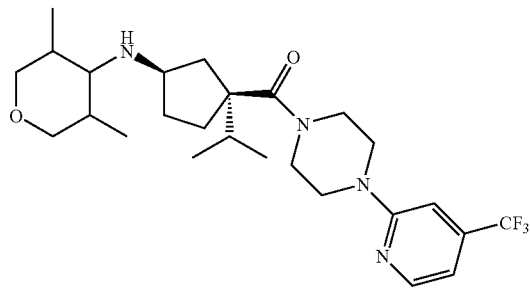

The title compound, as a mixture of diastereomers, was prepared in a fashion similar to that for Example 2 employing, in the reductive alkylation, 3,5-dimethyl-tetrahydropyran-4-one. MS calculated for $C_{26}H_{39}F_3N_4O_2$: (M+H) 497.3025; found 497.3311.

Example 22

(1R,3S)-3-isopropyl-N-[1-methyl-3-(1H-pyrazol-1-yl)propyl]-3-({4-[4-(trifluoromethyl)pyridin-2-yl]piperazin-1-yl}carbonyl)cyclopentanamine

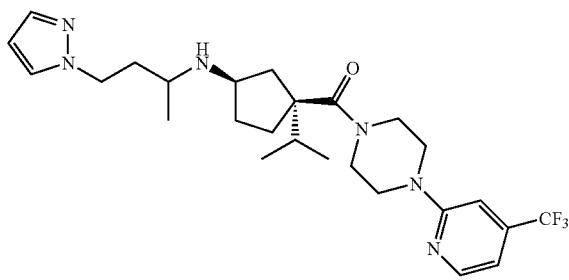

The title compound, as a mixture of diastereomers, was prepared in a fashion similar to that for Example 2 employing, in the reductive alkylation, 4-(1H-pyrazol-1-yl)butan-2-one. MS calculated for $C_{26}H_{37}F_3N_6O$: (M+H) 507.2981; found 507.2992.

Example 23

N-[(1R-3S)-3-isopropyl-3-({4-[4-(trifluoromethyl)pyridin-2-yl]piperazin-1-yl}carbonyl)cyclopentyl]tetrahydrofuran-3-amine

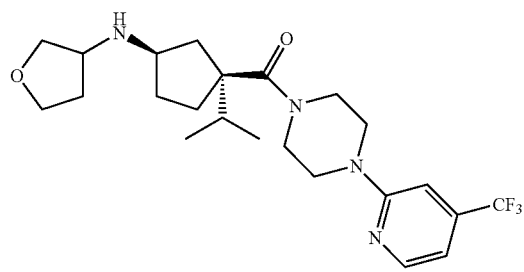

The title compound, as a mixture of diastereomers, was prepared in a fashion similar to that for Example 2 employing, in the reductive alkylation, dihydrofuran-3(2H)-one. MS calculated for $C_{23}H_{33}F_3N_4O_2$: (M+H) 455.2556; found 455.2064.

Example 24

N-[(1R,3S)-3-isopropyl-3-({4-[4-(trifluoromethyl)pyridin-2-yl]piperazin-1-yl}carbonyl)cyclopentyl]—N-methyltetrahydrofuran-3-amine

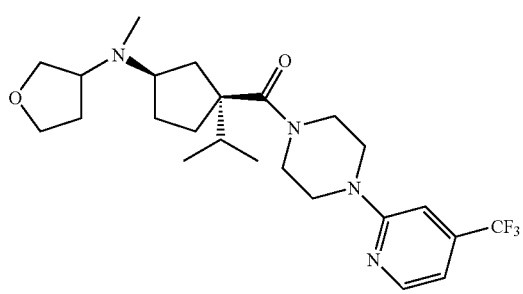

To a solution of N-[(1R,3S)-3-isopropyl-3-({4-[4-(trifluoromethyl)pyridin-2-yl]piperazin-1-yl}carbonyl)cyclopentyl]tetrahydrofuran-3-amine (160 mg) in 5mL of methanol was added a solution of formaldehyde (10 equiv) followed by NaCNBH3 (3 equiv). Once the reaction was complete, the volatiles were removed and the residue taken in ethyl acetate. The ethyl acetate layer was washed with aqueous NaOH (2.5N). The organic layer was dried over sodium sulfate, filtered and evaporated. The residue was purified by chromatography to give the title compound (126 mg). MS calculated for $C_{24}H_{35}F_3N_4O_2$: (M+H) 469.2712; found 469.2817.

Example 25

(1R,3S)-N-(34-dimethoxybenzyl)-3-isopropyl-3-({4-[4-(trifluoromethyl)pyridin-2-yl]piperazin-1-yl}carbonyl)cyclopentanamine

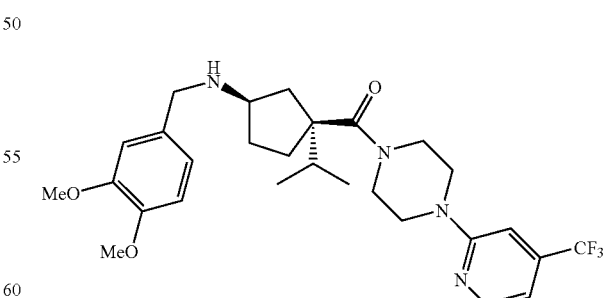

The title compound was prepared in a fashion similar to that for Example 2 employing, in the reductive alkylation, 3,4-dimethoxybenzaldehyde. MS calculated for $C_{28}H_{37}F_3N_4O_3$: (M+H) 535.2818; found 535.2940.

Example 26

(1R,3S)-N-(1H-indol-5-ylmethyl)-3-isopropyl-3-({4-[4-(trifluoromethyl)pyridin-2-yl]piperazin-1-yl}carbonyl)cyclopentanamine

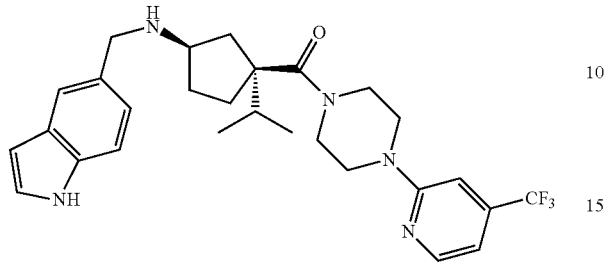

The title compound was prepared in a fashion similar to that for Example 2 employing, in the reductive alkylation, 1H-indole-5-carbaldehyde. MS calculated for $C_{28}H_{34}F_3N_5O$: (M+H) 514.2715; found 514.2752.

Example 27

4-({[(1R,3S)-3-isopropyl-3-({4-[4-(trifluoromethyl)pyridin-2-yl]piperazin-1-yl}carbonyl)cyclopentyl]amino}methyl)phenol

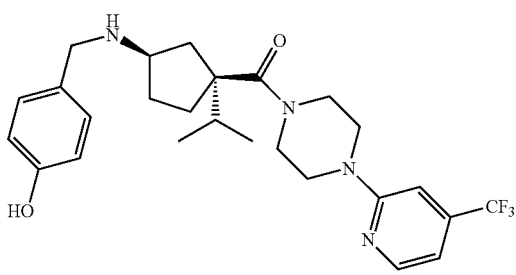

The title compound was prepared in a fashion similar to that for Example 2 employing, in the reductive alkylation, 4-hydroxybenzaldehyde. MS calculated for $C_{26}H_{33}F_3N_4O_2$: (M+H) 491.2556; found 491.2601.

Example 28

(1R,3S)-N-(4-fluorobenzyl)-3-isopropyl-3-({4-[4-(trifluoromethyl)pyridin-2-yl]piperazin-1-yl}carbonyl)cyclopentanamine

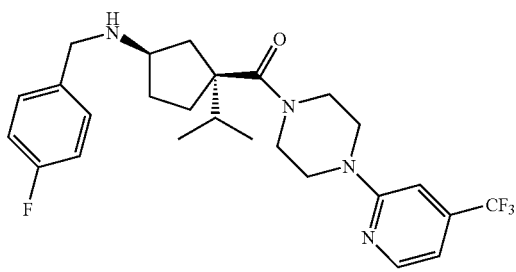

The title compound was prepared in a fashion similar to that for Example 2 employing, in the reductive alkylation, 4-fluorobenzaldehyde. MS calculated for $C_{26}H_{32}F_4N_4O$: (M+H) 493.2512; found 493.2605.

Example 29

5-({[(1R,3S)-3-isopropyl-3-({4-[4-(trifluoromethyl)pyridin-2-yl]piperazin-1-yl}carbonyl)cyclopentyl]amino}methyl)-2-methoxyphenol

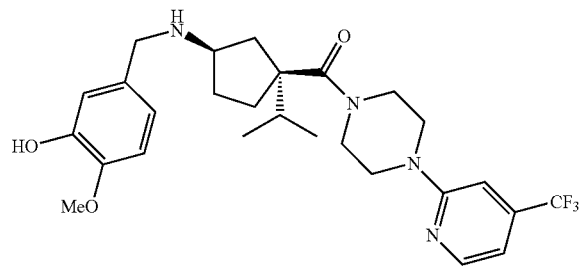

The title compound was prepared in a fashion similar to that for Example 2 employing, in the reductive alkylation, 3-hydroxy-4-methoxybenzaldehyde. MS calculated for $C_{27}H_{35}F_3N_4O_3$: (M+H) 521.2661; found 521.2747.

Example 30

6-({[(1R,3S)-3-isopropyl-3-({4-[4-(trifluoromethyl)pyridin-2-yl]piperazin-1-yl}carbonyl)cyclopentyl]amino}methyl)-2H-14-benzoxazin-3(4H)-one

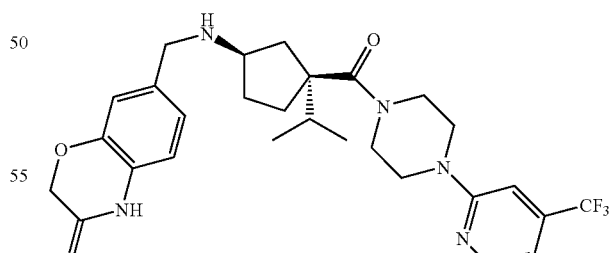

The title compound was prepared in a fashion similar to that for Example 2 employing, in the reductive alkylation, 3-oxo-3,4-dihydro-2H-benzo[b][1,4]oxazine-7-carbaldehyde. MS calculated for $C_{28}H_{34}F_3N_5O_3$: (M+H) 546.2614; found 546.2679.

Example 31

(1R,3S)-3-isopropyl-N-(3-methoxy-4-methylbenzyl)-3-({4-[4-(trifluoromethyl)pyridin-2-yl]piperazin-1-yl}carbonyl)cyclopentanamine

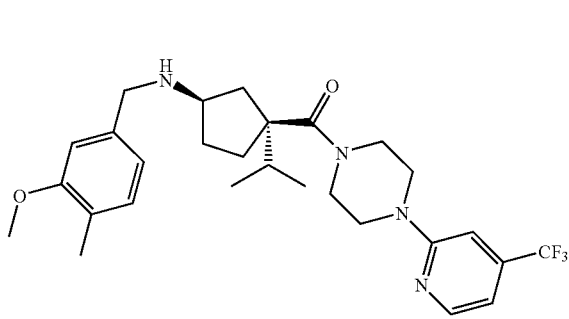

The title compound was prepared in a fashion similar to that for Example 2 employing, in the reductive alkylation, 3-methoxy-4-methylbenzaldehyde. MS calculated for $C_{28}H_{34}F_3N_5O_3$: (M+H) 519.2869; found 519.2986.

Example 32

((1S,3R)-3-(benzylamino)-1-isopropylcyclopentyl)(4-(4-(trifluoromethyl)pyridin-2-yl)piperazin-1-yl)methanone

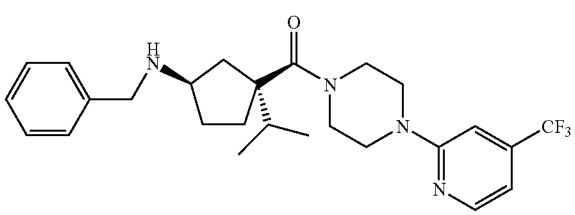

Example 33

((1S,3R)-3-(4-chlorobenzylamino)-1-isopropylcyclopentyl)(4-(4-(trifluoromethyl)pyridin-2-yl)piperazin-1-yl)methanone

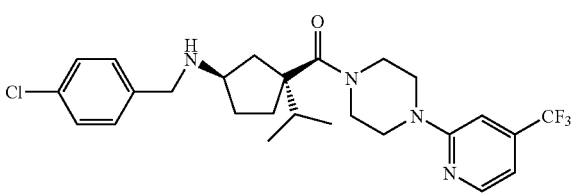

Example 34

((1S,3R)-3-(4-methoxybenzylamino)-1-isopropylcyclopentyl)(4-(4-(trifluoromethyl)pyridin-2-yl)piperazin-1-yl)methanone

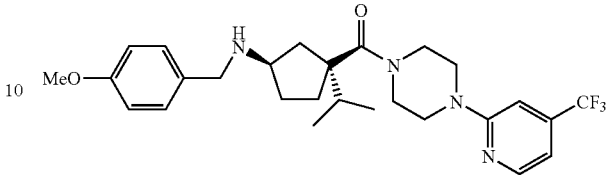

Example 35

((1S,3R)-3-(4-hydroxy-3-methylbutan-2-ylamino)-1-isopropylcyclopentyl)(4-(4-(trifluoromethyl)pyridin-2-yl)piperazin-1-yl)methanone

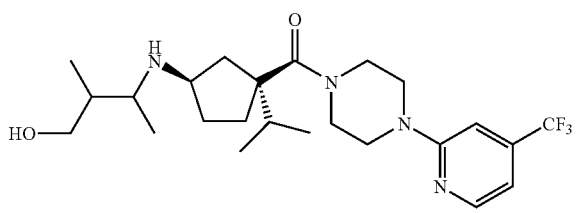

Example 36

((1S,3R)-3-(4-hydroxy-4-methylpentan-2-ylamino)-1-isopropylcyclopentyl)(4-(4-(trifluoromethyl)pyridin-2-yl)-5,6-dihydropyridin-1(2H)-yl)methanone

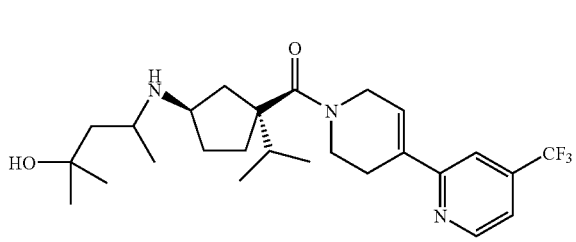

Example 37

((1S,3R)-3-(2-(chloromethyl)-3-hydroxy-2-methylpropylamino)-1-isopropylcyclopentyl)(4-(4-(trifluoromethyl)pyridin-2-yl)-5,6-dihydropyridin-1(2H)-yl)methanone

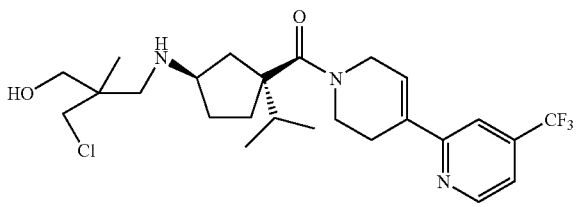

Example 38

((1S,3R)-1-isopropyl-3-((tetrahydro-2H-pyran-4-yl)methylamino)cyclopentyl)(4-(4-(trifluoromethyl)pyridin-2-yl)-5,6-dihydropyridin-1(2H)-yl)methanone

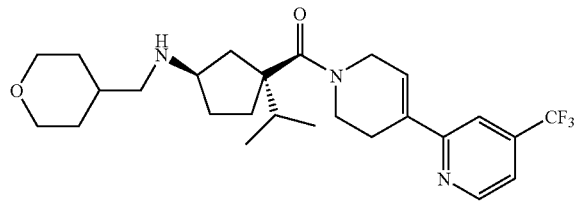

Example 39

((1S,3R)-1-isopropyl-3-(methyl(neopentyl)amino)cyclopentyl)(4-(4-(trifluoromethyl)pyridin-2-yl)piperazin-1-yl)methanone

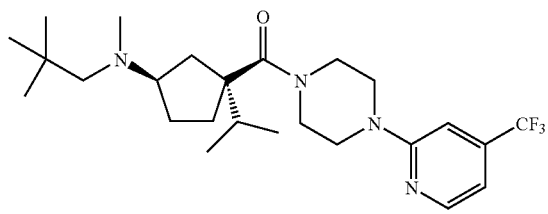

Example 40

N-((1R,3S)-3-isopropyl-3-(1-(4-(trifluoromethyl)pyridin-2-yl)piperazine-4-carbonyl)cyclopentyl)benzenesulfonamide

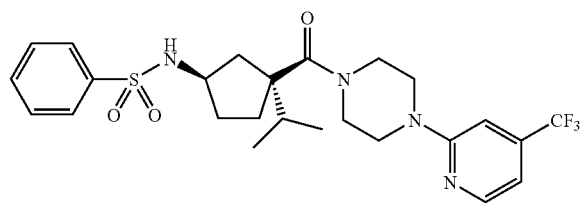

Example 41

((1S,3R)-1-isopropyl-3-(1-phenylethylamino)cyclopentyl)(4-(4-(trifluoromethyl)pyridin-2-yl)piperazin-1-yl)methanone

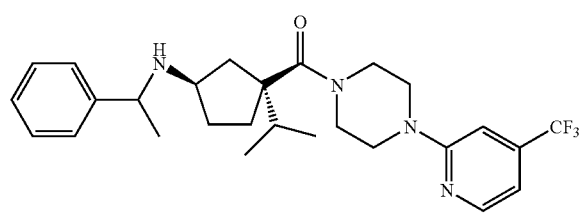

Example 42

((1S,3R)-1-isopropyl-3-(1-phenylpropylamino)cyclopentyl)(4-(4-(trifluoromethyl)pyridin-2-yl)piperazin-1-yl)methanone

Example 43

((1S,3R)-3-(diethylamino)-1-isopropylcyclopentyl)(4-(5-(trifluoromethyl)pyridin-3-yl)-5,6-dihydropyridin-1(2H)-yl)methanone

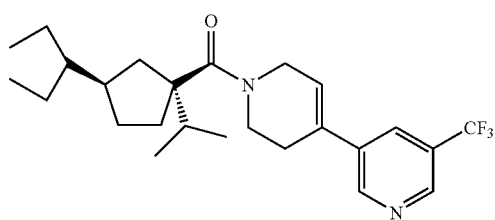

Example 44

((1S,3R)-1-isopropyl-3-(1-(tetrahydro-2H-pyran-4-yl)ethylamino)cyclopentyl)(4-(4-(trifluoromethyl)pyrimidin-2-yl)piperazin-1-yl)methanone

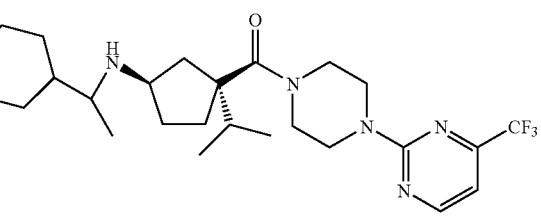

Example 45

((1S,3R)-1-isopropyl-3-((3-methoxy-tetrahydro-2H-pyran-4-yl)methylamino)cyclopentyl)(4-(6-(trifluoromethyl)pyridin-2-yl)piperazin-1-yl)methanone

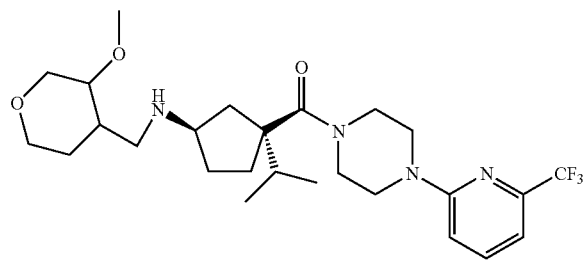

Example 46

((1S,3R)-3-(1,2-diphenylethylamino)-1-isopropylcyclopentyl)(4-(6-(trifluoromethyl)pyrimidin-4-yl)piperazin-1-yl)methanone

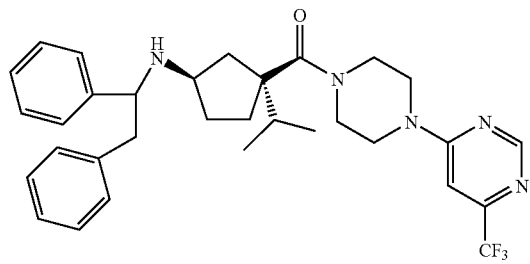

Example 47

((1S,3R)-1-isopropyl-3-(phenethylamino)cyclopentyl)(4-(2-methyl-6-(trifluoromethyl)pyrimidin-4-yl)piperazin-1-yl)methanone

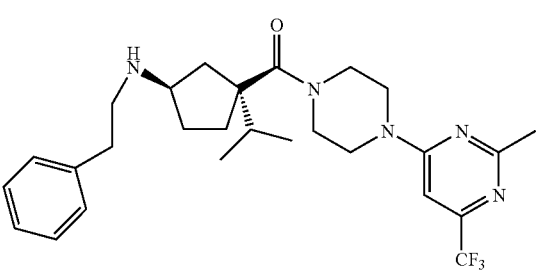

Example 48

3-fluoro-N-((1R,3S)-3-isopropyl-3-(1-(4-(trifluoromethyl)pyridin-2-yl)piperazine-4-carbonyl)cyclopentyl)benzenesulfonamide

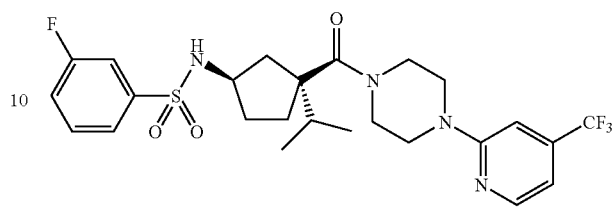

Example 49

3-((1R,3S)-3-(2-hydroxypropan-2-yl)-3-(1-(4-(trifluoromethyl)pyridin-2-yl)piperazine-4-carbonyl)cyclopentylamino)-2,2-dimethylpropanoic acid

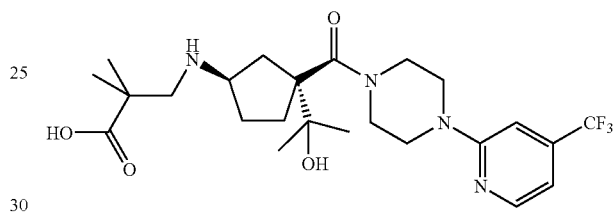

Example 50

((1S,3R)-1-isopropyl-3-(pyridin-3-ylmethylamino)cyclopentyl)(4-(4-(trifluoromethyl)pyridin-2-yl)piperazin-1-yl)methanone

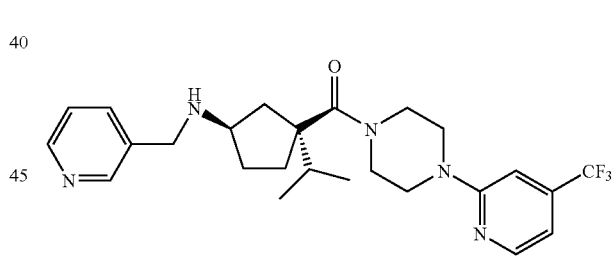

Example 51

((1S,3R)-3-(3-hydroxypropylamino)-1-isopropylcyclopentyl)(4-(4-(trifluoromethyl)pyridin-2-yl)piperazin-1-yl)methanone

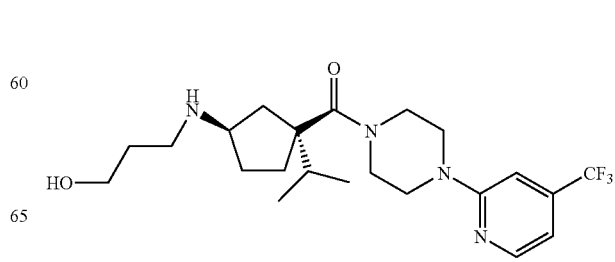

Example 52

((1S,3R)-3-(benzyl(isopropyl)amino)-1-isopropylcyclopentyl)(4-(4-(trifluoromethyl)pyridin-2-yl)piperazin-1-yl)methanone

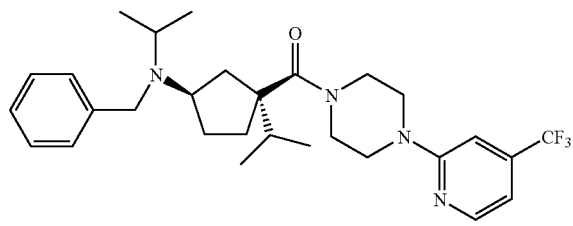

Example 53

N-((1R,3S)-3-isopropyl-3-(1-(4-(trifluoromethyl)pyridin-2-yl)piperazine-4-carbonyl)cyclopentyl)benzamide

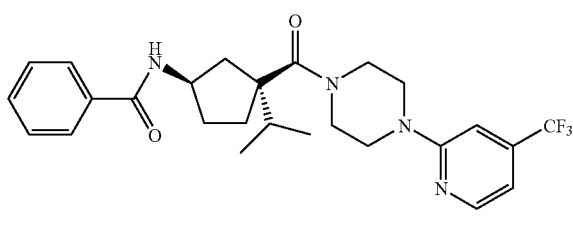

Example 54

N-((1R,3S)-3-isopropyl-3-(1-(4-(trifluoromethyl)pyridin-2-yl)piperazine-4-carbonyl)cyclopentyl)cyclohexanecarboxamide

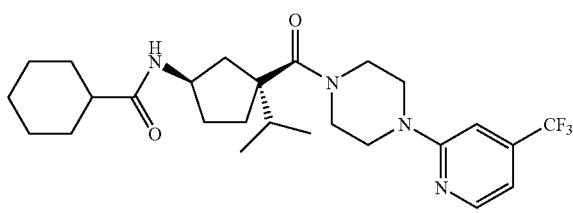

Example 55

N-((1R,3S)-3-isopropyl-3-(1-(4-(trifluoromethyl)pyridin-2-yl)piperazine-4-carbonyl)cyclopentyl)-2-(tetrahydro-2H-pyran-4-yl)acetamide

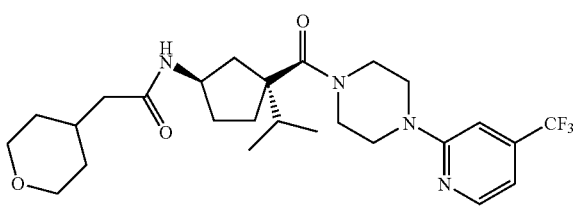

Example 56

((1S,3R)-1-isopropyl-3-(naphthalen-2-ylmethylamino)cyclopentyl)(4-(4-(trifluoromethyl)pyridin-2-yl)piperazin-1-yl)methanone

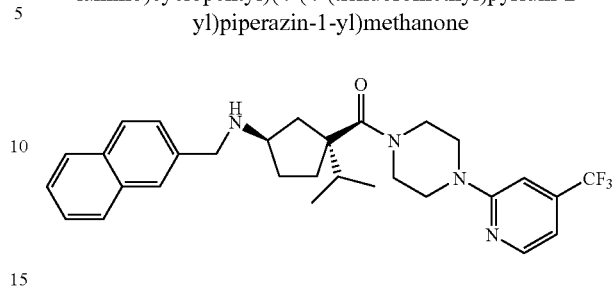

Example 57

((1S,3R)-3-(4-hydroxy-4-(thiazol-2-yl)cyclohexylamino)-1-isopropylcyclopentyl)(4-(4-(trifluoromethyl)pyridin-2-yl)piperazin-1-yl)methanone

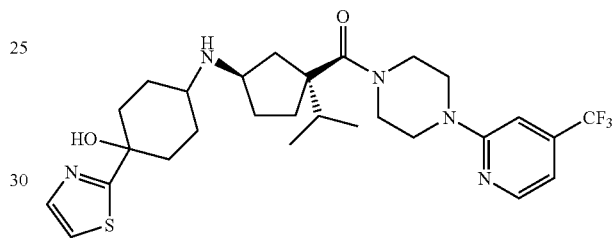

Example 58

((1S,3R)-3-(4-phenoxybenzylamino)-1-isopropylcyclopentyl)(4-(4-(trifluoromethyl)pyridin-2-yl)piperazin-1-yl)methanone

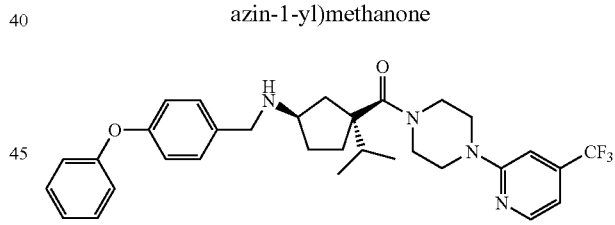

Example 59

((1S,3R)-3-(3,4-dimethoxybenzylamino)-1-isopropylcyclopentyl)(4-(4-(trifluoromethyl)pyridin-2-yl)piperazin-1-yl)methanone

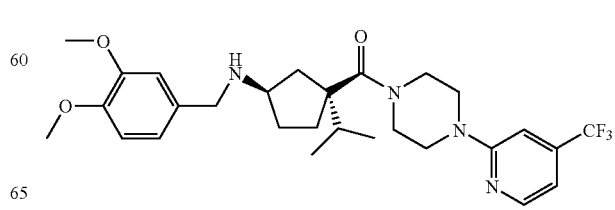

Example 60

(((1S,3R)-3-(3,5-bis(trifluoromethyl)benzylamino)-1-isopropylcyclopentyl)(4-(4-(trifluoromethyl)pyridin-2-yl)piperazin-1-yl)methanone

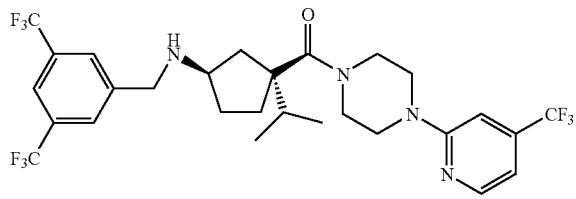

Example 61

N-((1R,3S)-3-isopropyl-3-(1-(4-(trifluoromethyl)pyridin-2-yl)piperazine-4-carbonyl)cyclopentyl)methanesulfonamide

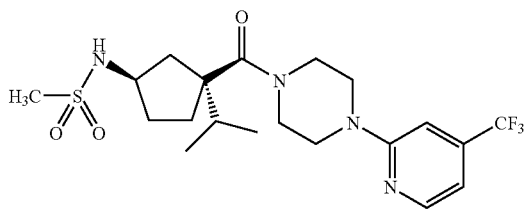

Example 62

N-((1R,3S)-3-isopropyl-3-(1-(4-(trifluoromethyl)pyridin-2-yl)piperazine-4-carbonyl)cyclopentyl)-4-(trifluoromethyl)benzenesulfonamide

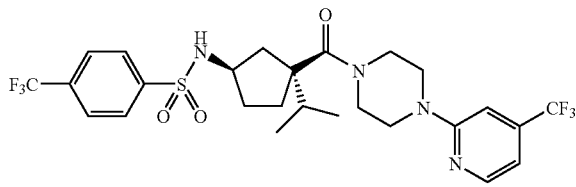

Example 63

((1S,3R)-1-isopropyl-3-(neopentylamino)cyclopentyl)(4-(4-(trifluoromethyl)pyridin-2-yl)piperazin-1-yl)methanone

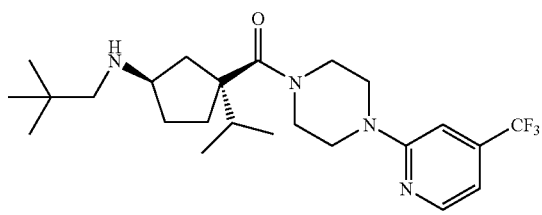

Example A

CCR2 In Vitro Assays

The capacity of the novel compounds of the invention to antagonize chemokine receptor (e.g., CCR2) function can be determined using a suitable screen (e.g., high through-put assay). For example, an agent can be tested in an extracellular acidification assay, calcium flux assay, ligand binding assay or chemotaxis assay (see, for example, Hesselgesser et al., J Biol. Chem. 273(25):15687-15692 (1998); WO 00/05265 and WO 98/02151).

In a suitable assay, a CCR2 protein which can be isolated or recombinantly derived is used which has at least one property, activity or functional characteristic of a mammalian CCR2 protein. The specific property can be a binding property (to, for example, a ligand or inhibitor), a signalling activity (e.g., activation of a mammalian G protein, induction of rapid and transient increase in the concentration of cytosolic free calcium $[Ca^{++}]i$, cellular response function (e.g., stimulation of chemotaxis or inflammatory mediator release by leukocytes), and the like.

In an example binding assay, a composition containing a CCR2 protein or variant thereof is maintained under conditions suitable for binding. The CCR2 receptor is contacted with a compound to be tested, and binding is detected or measured.

In an example cell-based assay, cells are used which are stably or transiently transfected with a vector or expression cassette having a nucleic acid sequence which encodes the CCR2 receptor. The cells are maintained under conditions appropriate for expression of the receptor and are contacted with an agent under conditions appropriate for binding to occur. Binding can be detected using standard techniques. For example, the extent of binding can be determined relative to a suitable control. Also, a cellular fraction, such as a membrane fraction, containing the receptor can be used in lieu of whole cells.

Detection of binding or complex formation in an assay can be detected directly or indirectly. For example, the agent can be labeled with a suitable label (e.g., fluorescent label, label, isotope label, enzyme label, and the like) and binding can be determined by detection of the label. Specific and/or competitive binding can be assessed by competition or displacement studies, using unlabeled agent or a ligand as a competitor.

The CCR2 antagonist activity of compounds of the invention can be reported as the inhibitor concentration required for 50% inhibition ($IC_{50}$ values) of specific binding in receptor binding assays using $^{125}$I-labeled MCP-1, as ligand, and Peripheral Blood Mononuclear Cells (PBMCs) prepared from normal human whole blood via density gradient centrifugation. Specific binding is preferably defined as the total binding (e.g., total cpm on filters) minus the non-specific binding. Non-specific binding is defined as the amount of cpm still detected in the presence of excess unlabeled competitor (e.g., MCP-1).

Example B

Binding Assay

Human PBMCs are used to test compounds of the invention in a binding assay. For example, 200,000 to 500,000 cells are incubated with 0.1 to 0.2 nM $^{125}$I-labeled MCP-1, with or without unlabeled competitor (10 nM MCP-1) or various concentrations of compounds to be tested. $^{125}$I-labeled MCP-1, are prepared by suitable methods or purchased from commercial vendors (Perkin Elmer, Boston Mass.). The binding reactions are performed in 50 to 250 µL of a binding buffer consisting of 1M HEPES pH 7.2, and 0.1% BSA (bovine serum albumin), for 30 min at room temperature. The binding reactions are terminated by harvesting the membranes by rapid filtration through glass fiber filters (Perkin Elmer) which is presoaked in 0.3% polyethyleneimine or Phosphate Buffered Saline (PBS). The filters were rinsed with approximately 600 µL of binding buffer containing 0.5 M NaCl or PBS, then dried, and the amount of bound radioactivity is determined by counting on a Gamma Counter (Perkin Elmer).

Active compounds of the present invention have $IC_{50}$ values less than about 3000 nM.

| EXAMPLE NUMBER | CCR2 $IC_{50}$ nM |
| --- | --- |
| 1 | 19.8 |
| 2 | 62.0 and 391 |
| 3 | 66.9 and 362 |
| 5 | 616 |
| 7 | 617 |
| 8 | 476 |
| 9 | 338 |
| 10 | 519 |
| 11 | 420 |
| 12 | 660 |
| 13 | 273 |
| 14 | 74.8 |
| 15 | 541 |
| 16 | 227 |
| 17 | 190 |
| 18 | 51.7 |
| 19 | 138 |
| 20 | 80.6 |
| 21 | 10.1 |
| 22 | 504 |
| 23 | 157 |
| 24 | 181 |
| 25 | 500 |
| 26 | 273 |
| 27 | 470 |
| 28 | 389 |
| 29 | 736 |
| 30 | 364 |
| 31 | 334 |

Example C

Chemotaxis Assay

The capacity of compounds of the invention to antagonize CCR2 function can be determined in a leukocyte chemotaxis assay using human peripheral blood mononuclear cells, in a modified Boyden Chamber (Neuro Probe). 500,000 cells in serum free DMEM media (In Vitrogen) are incubated with or without the inhibitors and warmed to 37° C. The chemotaxis chamber (Neuro Probe) is also prewarmed. Then 400 µL of warmed 10 nM MCP-1 is added to the bottom chamber in all wells except the negative control which has DMEM added. An 8 micron membrane filter (Neuro Probe) is placed on top and the chamber lid is closed. Cells are then added to the holes in the chamber lid which are associated with the chamber wells below the filter membrane. The whole chamber is incubated at 37° C. 5% $CO_2$ for 30 minutes. The cells are then aspirated off, the chamber lid opened, and the filter gently removed. The top of the filter is washed 3 times with PBS and the bottom is left untouched. The filter is air dried and stained with Wright Geimsa stain (Sigma). Filters are counted by microscopy. The negative control wells serve as background and are subtracted from all values. Antagonist potency is determined by comparing the number of cells that migrate to the bottom chamber in wells which contained antagonist, to the number of cells which migrate to the bottom chamber in MCP-1 control wells.

Active compounds of the invention have $IC_{50}$ values less than about 3000 nM.

Example D

CCR5 Expression

A leukophoresis (Biological Specialty, Colmar, Pa.) is obtained from normal, drug free donors and peripheral blood mononuclear cells (PBMCs) are isolated via density gradient centrifugation. Monocytes are further isolated via centrifugal elutriation. After being washed, the monocytes are re-suspended at $10^6$ cells/ml with RPMI (Invitrogen, Carlsbad, Calif.) supplemented with 10% FBS (Hyclone, Logan, Utah) and 10-20 ng/mL of recombinant human IL-10 (R&D systems, Minneapolis, Minn.) and incubated in the same medium at 37° C. with 5% $CO_2$ for 24-48 hr. CCR5 expression on the IL-10-treated monocytes is then verified by staining the cells with a PE-conjugated anti-human CCR5 antibody ((PharMingen, San Diego, Calif.), followed by FACS analysis using FACSCalibur (BD Biosciences, Bedford, Mass.).

Example E

CCR5 Binding Assay

In a 96 well MultiScreen™ filter plate (Millipore Systems, Billerica, Mass.), $3 \times 10^5$ IL-10-treated monocytes in 150 µL RPMI (Invitrogen, Carlsbad, Calif.) with 20 mM HEPES (Invitrogen, Carlsbad, Calif.) and 0.3% BSA (Sigma, St Louis, Mo.) are incubated at room temperature for 1 hr. with 0.2 nM $^{125}$I-MIP-1β (Perkin Elmer, Boston, Mass.) and a series concentrations of compound of the invention. Non-specific binding is determined by incubating the cells with 0.3 µM MIP-1β (R&D Systems, Minneapolis, Minn.). The binding reaction is terminated by harvesting the cells onto the filter in the plate on a vacuum manifold (Millipore Systems, Billerica, Mass.). The filter is then washed 5 times with RPMI (Invitrogen, Carlsbad, Calif.) supplemented with 20 mM HEPES (invitrogen, Carlsbad, Calif.), 0.3% BSA (Sigma, St Louis, Mo.) and 0.4 M NaCl on the vacuum manifold, air dried, and peeled from the plate. The filter dishes corresponding to the sample wells in a filter plate are punched out using the Millipore Punch System (Millipore Systems, Billerica, Mass.). The amount of bound radioactivity on each filter dish is determined by counting on a gamma counter. Specific binding is defined as the total binding minus the non-specific binding. The binding data are evaluated with Prism (Graph-Pad Software, San Diego, Calif.). Active compounds have a binding affinity of about 1 µM or less according to this assay.

Example F

HIV-1 Entry Assay

Replication defective HIV-1 reporter virions are generated by cotransfection of a plasmid encoding the NL4-3 strain of HIV-1 (which has been modified by mutation of the envelope gene and introduction of a luciferase reporter plasmid) along with a plasmid encoding one of several HIV-1 envelope genes as described by, for example, Connor et al, *Virology*, 206 (1995), 935-944. Following transfection of the two plasmids by calcium phosphate precipitation, the viral supernatants are harvested on day 3 and a functional viral titer determined. These stocks are then used to infect U87 cells stably expressing CD4 and the chemokine receptor CCR5 which have been preincubated with or without test compound. Infections are carried out for 2 hours at 37° C., the cells washed and media replaced with fresh media containing compound. The cells are incubated for 3 days, lysed and luciferase activity determined. Results are reported as the concentration of compound required to inhibit 50% of the luciferase activity in the control cultures.

Example G

HIV-1 Replication Assay in MT-4 Cells

Inhibition of HIV-1 NL4.3 (or III$_B$) replication assays can be carried out as previously described (Bridger, et al., *J. Med. Chem.* 42:3971-3981 (1999); De Clercq, et al., *Proc. Natl. Acad. Sci.* 89:5286-5290 (1992); De Clercq, et al., *Antimicrob. Agents Chemother.* 38:668-674 (1994); Bridger, et al. *J. Med. Chem.* 38:366-378 (1995)). To summarize, anti-HIV activity and cytotoxicity measurements are carried out in parallel and are based on the viability of MT-4 cells that are infected with HIV in the presence of various concentrations of the test compounds. After the MT-4 cells are allowed to proliferate for 5 days, the number of viable cells are quantified by a tetrazolium-based calorimetric 3-(4,5-dimethylthiazol-2-yl)-2,5-diphenyltetrazolium bromide (MTT) procedure in 96-well microtrays. Results can be quanitited to yield $EC_{50}$ values which represent the concentration required to protect 50% of the virus-infected cells against viral cytopathicity.

Various modifications of the invention, in addition to those described herein, will be apparent to those skilled in the art from the foregoing description. Such modifications are also intended to fall within the scope of the appended claims. Each reference, including patents, patent applications, and publications, cited in the present application is incorporated herein by reference in its entirety.

What is claimed is:

1. A compound of Formula I:

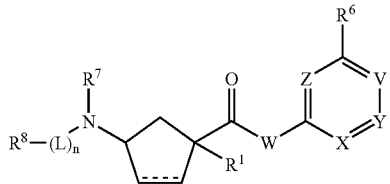

or pharmaceutically acceptable salts or prodrugs thereof, wherein:

a dashed line indicates an optional bond;

W is:

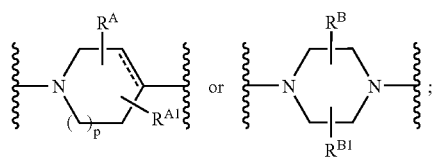

V is N, NO or $CR^5$;
X is N, NO or $CR^2$;
Y is N, NO or $CR^3$;
Z is N, NO or $CR^4$; wherein no more than one of V, X, Y and Z is NO;

L is $C_{1-4}$ alkylenyl, $C_{2-4}$ alkenylenyl, $C_{2-4}$ alkynylenyl, C(O), C(O)NR$^9$, S(O), S(O)NR$^9$, S(O)$_2$, or S(O)$_2$NR$^9$;

$R^A$, $R^{A1}$, $R^B$ and $R^{B1}$ are each, Independently, H, OH, halo, $C_{1-6}$ alkyl, $C_{1-6}$ alkenyl, $C_{1-6}$alkynyl, $C_{2-6}$alkynyl, $C_{1-6}$haloalkyl, $C_{1-6}$alkoxy, $C_{1-6}$haloalkoxy, heterocyclyl, carbocyclyl, $NR^{10}R^{12}$, $NR^{10}CO_2R^{11}$; $NR^{10}CONR^{13}R^{12}$, $NR^{10}SO_2NR^{10}R^{12}$, $NR^{10}$—SO$_2$—$R^{11}$, CN, CONR$^{10}R^{12}$, $CO_2R^{10}$, NO$_2$, SR$^{10}$, SOR$^{10}$, SO$_2R^{10}$, or SO$_2$—NR$^{10}R^{12}$;

$R^1$ is $C_{1-6}$ alkyl, $C_{1-6}$ haloalkyl, $C_{1-6}$ hydroxyalkyl, —($C_{0-6}$ alkyl)—O—($C_{1-6}$ alkyl), —($C_{0-6}$alkyl)—S($C_{1-6}$ alkyl), —($C_{0-6}$alkyl)—($C_{3-7}$ cycloalkyl)—($C_{0-6}$ alkyl), OH, OR$^{10}$, SR$^{10}$, COR$^{11}$, CO$_2R^{10}$, CONR$^{10}R^{12}$, carbocyclyl, heterocyclyl, CN, NR$^{10}R^{12}$, NR$^{10}SO_2R^{10}$, NR10COR$^{10}$, NR$^{10}CO_2R^{10}$, NR$^{10}CONR^{12}$, CR$^{10}R^{11}CO_2R^{10}$ or CR$^{10}R^{11}OCOR^{10}$;

$R^3$, $R^3$, $R^4$, $R^5$ and $R^6$ are each, independently, H, OH, halo, $C_{1-6}$alkyl, $C_{1-6}$haloalkyl, $C_{1-6}$alkoxy, $C_{1-6}$ haloalkoxy, $C_{1-6}$ thioalkoxy, $NR^{10}R^{12}$, $NR^{10}CO_2R^{11}$, $NR^{10}CONR^{10}R^{12}$, $NR^{10}SO_2NR^{10}R^{12}$, $NR^{10}$—SO$_2$—$R^{11}$, heterocyclyl, carbocyclyl, carbocylyloxy, heterocyclyloxy, CN, NO$_2$, COR$^{11}$, CONR$^{10}R^{12}$, CO$_2R^{10}$, NO$_2$, SR$^{10}$, SOR$^{10}$, SO$_2R^{10}$; or SP$_2$—NR$^{10}R^{12}$;

$R^7$ is H or $C_{1-8}$ alkyl optionally substituted by 1, 2, 3, 4, 5 or 6 substituents independently selected from halo, $C_{1-10}$haloalkyl, Cy, CN, NO$_2$, OR$^a$, C(O)R$^b$, C(O)NR$^C$R$^d$, C(O)OR$^a$, OC(O)R$^b$, OC(O)NR$^C$R$^d$, NR$^C$R$^d$, NR$^C$C(O)R$^b$, NR$^C$C(O)OR$^a$, S(O)R$^b$, S(O)NR$^C$R$^d$, S(O)$_2R^b$, NR$^C$S(O)$_2R^b$, S(O)$_2$NR$^C$R$^d$; or $R^7$ is H, $C_{1-8}$alkyl which is unsubstituted or substituted with 1-6 substituents selected from: hydroxy, —O—$C_{1-6}$alkyl, —NR$^{12a}R^{12a}$, —NR$^{12a}COR^{13a}$, —NR$^{12a}SO_2R^{14a}$, COR$^{11a}$, —CONR$^{12a}R^{12a}$, phenyl and heterocycle, where the alkyl, phenyl, and heterocycle are unsubstituted or substituted with 1-3 substituents selected from: halo, hydroxy, $C_{1-3}$alkyl, $C_{1-3}$alkoxy, —CO$_2$H, —CO$_2$—$C_{1-6}$ alkyl, trifluoromethyl, and —SO$_2C_{1-6}$alkyl which is unsubstituted or substituted with 1-6 substituents selected from: hydroxy, halo, —O—$C_{1-6}$ alkyl, CN, —NR$^{12a}R^{12a}$, NR$^{12a}COR^{13a}$, —NR$^{12a}SO_2R^{14a}$, —COR$^{11a}$, —CONR$^{12a}R^{12a}$, phenyl and heterocycle, where the alkyl, phenyl, and heterocycle are unsubstituted or substituted with 1-3 substituents selected from: halo, hydroxy, $C_{1-3}$ alkyl, $C_{1-3}$alkoxy, —CO$_2$H, —CO$_2$—$C_{1-6}$alkyl, and trifluoromethyl; or $R^7$ is H, $C_{1-6}$alkyl unsubstituted or substituted with 1-3 substituents selected from: halo, hydroxy, —CO$_2$H, —CO$_2C_{1-6}$ alkyl, and —O—$C^{1-3}$ alkyl;

$R^8$ is $C_{1-10}$ alkyl, $C_{2-10}$ alkenyl, $C_{2-10}$ alkynyl, $C_{1-10}$ haloalkyl, aryl, cycloalkyl, heteroaryl, or heterocycloalkyl, wherein said $C_{1-10}$ alkyl, $C_{2-10}$ alkenyl, $C_{2-10}$ alkynyl, $C_{1-10}$ haloalkyl, aryl, cycloalkyl, heteroaryl, or heterocycloalkyl is optionally substituted with 1, 2, 3, 4, 5, or 6 substituents independently selected from oxo, hydroxy, halo, $C_{1-4}$ alkyl, $C_{1-4}$alkoxy, $C_{2-4}$ alkenyl, $C_{2-4}$alkynyl, $C_{1-4}$ haloalkyl, $C_{1-4}$ hydroxyalkyl, $C_{1-4}$ cyanoalkyl, Cy', —($C_{1-4}$ alkyl)-Cy', —C(O)—R$^a$, CN, NO$_2$, —(CH$_2$)$_q$—ORa', —(CH$_2$)$_q$—SR$^a'$, —(CH$_2$)$_q$—C(O)R$^{b'}$, —(CH$_2$)$_q$—C(O)NR$^C$R$^{d'}$, —(CH$_2$)$_q$—C(O)OR$^{a'}$, —(CH$_2$)$_q$—S(O)R$^{b'}$, —(CH$_2$)$_q$—S(O)$_2R^{b'}$, and —(CH$_2$)$_q$—S(O)$_2$NR$^C$R$^{d'}$; or $R^8$ is selected from $C_{1-10}$alkyl, —SO$_2C_{1-10}$alkyl, pyridyl or phenyl, unsubstituted or substituted with 1-5 substituents selected from: hydroxy, halo, —O—$C_{1-6}$alkyl, —S—$C_{1-6}$alkyl, CN, —NR$^{12a}R^{12a}$, —NR$^{12a}COR^{13a}$, —$NR^{12a}SO_2R^{14a}$, —$COR^{11a}$, —$CONR^{12a}R^{12a}$, —$SO_2R^{14a}$, heterocycle, =O (where the oxygen is connected via a double bond), phenoxy and phenyl, where the alkyl, phenyl, phenoxy and heterocycle are unsubstituted or substituted with 1-3 substituents selected from: halo, hydroxy, $C_{1-3}$alkyl, $C_{1-3}$alkoxy, —$COR^{11a}$, —CN, —$NR^{12a}R^{12a}SO_2R^{14a}$, —$NR^{12a}COR^{13a}$, —$NR^{12a}SO_2R^{14a}$, and —$CONR^{12a}R^{12a}$, where the alkyl and alkoxy are optionally substituted with 1-5 fluoro; or $R^8$ is a group of formula:

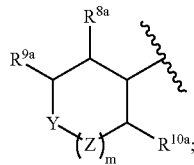

Y and Z are independently selected from —O—, —$NR^{12b}$, —S—, —SO—, —$SO_2$—, —$CR^{12b}R^{12b}$—, $NSO_2R^{14b}$—, —$NCOR^{13b}$—, —$CR^{12b}COR^{11b}$—, —$CR^{12b}OCOR^{13b}$—, —C— and —CO—;

$R^{8a}$ is selected from: hydrogen, $C_{1-6}$alkyl unsubstituted or substituted with 1-6 substituents selected from fluoro, $C_{1-3}$alkoxy, hydroxy and —$COR^{11b}$, fluoro, —O—$C_3$alkyl unsubstituted or substituted with 1-3 fluoro, $C_{3-6}$cycloalkyl, —O—$C_{3-6}$cycloalkyl, hydroxy, —$COR^{11b}$, —$OCOR^{13b}$; or $R^7$ and $R^{8a}$ together are $C_{2-4}$alkyl or $C_{0-2}$alkyl-O—$C_{1-3}$alkyl, forming a 5-7 membered ring;

$R^{9a}$ is selected from: hydrogen, $C_{1-6}$alkyl unsubstituted or substituted with 1-6 substituents selected from fluoro, $C_{1-3}$alkoxy, hydroxy and —$COR^{11b}$, $COR^{11b}$, hydroxy and —O—$C_{1-6}$alkyl unsubstituted or substituted with 1-6 substituents selected from fluoro, $C_{1-3}$alkoxy, hydroxy and —$COR^{11b}$;

or $R^{8a}$ and $R^{9a}$ together are $C_{1-4}$alkyl or $C_{0-3}$alkyl-O—$C_{0-3}$alkyl, forming a 3-6 membered ring;

$R^{10a}$ is selected from: hydrogen, hydroxy, $C_{1-6}$alkyl unsubstituted or substituted with 1-6 fluoro, fluoro, —O—$C_{3-6}$cycloalkyl and —O—$C_{1-3}$alkyl unsubstituted or substituted with 1-6 fluoro;

or $R^{8a}$ and $R^{10a}$ together are $C_{2-5}$alkyl, forming a 5-6 membered ring, where said alkyl is unsubstituted or substituted with 1-3 substituents independently selected from halo, hydroxy, $COR^{11b}$, $C_{1-3}$alkyl and $C_{1-3}$alkoxy;

or $R^{8a}$ and $R^{10a}$ together are O—$C_{1-2}$alkyl-O-$C_{1-2}$alkyl, forming a 6-8 membered ring, where said alkyl is unsubstituted or substituted with 1-3 substituents independently selected from halo, hydroxy, —$COR^{11b}$, $C_{1-3}$alkyl and $C_{1-3}$alkoxy;

or $R^{8a}$ and $R^{10a}$ together are —O—$C_{1-2}$alkyl-O—, forming a 6-7 membered ring, where said alkyl is unsubstituted or substituted with 1-3 substituents independently selected from halo, hydroxy, —$COR^{11b}$, $C_{1-3}$allyl and $C_{1-3}$alkoxy;

$R^{11a}$ and $R^{11b}$ are independently selected from: hydroxy, hydrogen, $C_{1-6}$alkyl, —O—$C_{1-6}$allyl, benzyl, phenyl and $C_{3-6}$cycloalkyl, where said alkyl, phenyl, benzyl and cycloalkyl groups are unsubstituted or substituted with 1-3 substituents independently selected from halo, hydroxy, $C_{1-3}$alkyl, $C_{1-3}$alkoxy, —$CO_2H$, —$CO_2$—$C_{1-6}$ alkyl, and trifluoromethyl;

$R^{12a}$ and $R^{12b}$ are independently selected from: hydrogen, hydroxy, $C_{1-6}$alkyl, benzyl, phenyl, $C_{3-6}$ cycloalkyl, where the alkyl, phenyl, benzyl, and cycloalkyl groups are unsubstituted or substituted with 1-3 substituents independently selected from: halo, hydroxy, $C_{1-3}$alkyl, $C_{1-3}$alkoxy, $CO_2H$, —$CO_2$—$C_{1-6}$alkyl, and trifluoromethyl; or $R^{12a}$ and $R^{12b}$ are selected from: $C_{1-6}$alkyl unsubstituted or substituted with 1-6 substituents selected from fluoro, $C_{1-3}$alkoxy, hydroxy and $COR^{11b}$, fluoro, —O—$C_{1-3}$alkyl unsubstituted or substituted with 1-6 fluoro, $C_{3-6}$cycloalkyl, —O—$C_{3-6}$cycloalkyl, hydroxy, —O—$C_{1-6}$alkyl unsubstituted or substituted with 1-6 substituents selected from fluoro, $C_{1-3}$alkoxy, hydroxy and —$COR^{11b}$;

$R^{13a}$ and $R^{13b}$ are independently selected from: hydrogen, $C_{1-6}$alkyl, —O—$C_{1-6}$alkyl, benzyl, phenyl, $C_{3-6}$ cycloalkyl, where the alkyl, phenyl, benzyl, and cycloalkyl groups are unsubstituted or substituted with 1-3 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^{14a}$ and $R^{14b}$ are independently selected from: hydroxy, $C_{1-6}$alkyl, —O—$C_{1-6}$alkyl, benzyl, phenyl, $C_{3-6}$ cycloalkyl, where the alkyl, phenyl, benzyl, and cycloalkyl groups are unsubstituted or substituted with 1-3 substituents independently selected from: halo, hydroxy, $C_{1-3}$alkyl, $C_{1-3}$alkoxy, $CO_2H$, —$CO_2$—$C_{1-6}$ alkyl, and trifluoromethyl;

Cy and Cy' are, independently, aryl, heteroaryl, cycloalkyl, or heterocycloalkyl, each optionally substituted by 1,2, 3,4 or 5 substituents independently selected from oxo, hydroxy, halo, $C_{1-4}$ alkyl, $C_{2-4}$ alkenyl, $C_{2-4}$ alkynyl, $C_{1-4}$ haloalkyl, CN, $NO_2$, $OR^{a''}$, $SR^{a''}$, $C(O)R^{b''}$, $C(O)NR^{C''}R^{d''}$, $C(O)OR^{a''}$, $OC(O)R^{b''}$, $OC(O)NR^{C''}R^{d''}$, $NR^{c''}R^{d''}$, $NR^{C''}C(O)R^{b''}$, $NR^{C''}C(O)OR^{a''}$, $S(O)R^{b''}$, $S(O)NR^{C''}R^{d''}$, $S(O)_2R^{b''}$, and $S(O)_2NR^{C''}R^{d''}$, aryl, or heteroaryl, cycloalkyl, or heterocycloalkyl;

$R^9$ is H, $C_{1-10}$ alkyl, $C_{1-6}$ haloalkyl, $C_{2-6}$ alkenyl, or $C_{2-6}$ alkynyl, wherein said $C_{1-10}$ alkyl, $C_{1-6}$haloalkyl, $C_{2-6}$ alkenyl, or $C_{2-6}$ alkynyl is optionally substituted with 1, 2, or 3 substituents independently selected from OH, amino, halo, $C_{1-6}$alkyl, $C_{1-6}$haloalkyl, aryl, arylalkyl, heteroaryl, heteroarylalkyl, cycloalkyl and heterocycloalkyl;

$R^{10}$ is H, $C_{1-6}$alkyl, benzyl, phenyl, or $C_{3-6}$cycloalkyl, wherein said $C_{1-6}$ alkyl, benzyl, phenyl, or $C_{3-6}$cycloalkyl is optionally substituted with 1, 2, or 3 substituents independently selected from halo, OH, $C_{1-3}$ alkyl, $C_{1-3}$ haloalkyl, $C_{1-3}$ alkoxy, $C_{1-3}$ haloalkoxy, $CO_2H$, and $CO_2$—($C_{1-6}$alkyl);

$R^{11}$ is H, OH, $C_{1-6}$alkyl, $C_{1-6}$ alkoxy, benzyl, phenyl, benzyloxy, phenyloxy, $C_{3-6}$cycloalkyl or $C_{3-6}$cycloalkyloxy, wherein said $C_{1-6}$alkyl, $C_{1-6}$alkoxy, benzyl, phenyl, benzyloxy, phenyloxy, $C_{3-6}$cycloalkyl or $C_{3-6}$cycloalkyloxy, is optionally substituted with 1, 2 or 3 substituents independently selected from halo, OH, $C_{1-3}$ alkyl, $C_{1-3}$ alkoxy, $CO_2H$, $CO_2$—($C_{1-6}$alkyl) and $CF_3$;

$R^{12}$ is H, $C^{1-6}$alkyl, benzyl, phenyl, or $C^{3-6}$ cycloalkyl, wherein said $C_{1-6}$alkyl, benzyl, phenyl, or $C_{3-6}$cycloalkyl is optionally substituted with 1,2, or 3 substituents independently selected from halo, OH, $C_{1-3}$ alkyl, $C_{1-3}$ haloalkyl, $C_{1-3}$ alkoxy, $C_{1-3}$ haloalkoxy, $CO_2H$, and $CO_2$—($C_{1-6}$alkyl);

$R^a$, $R^{a'}$ and $R^{a''}$ are, independently, H, $C_{1-6}$ alkyl, $C_{1-6}$ alkoxy, $C_{1-6}$ haloalkyl, $C_{2-6}$ alkenyl, $C_{2-6}$alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, amino, halo, $C_{1-6}$alkyl, aryl, arylalkyl, heteroaryl, heteroarylalkyl, cycloalkyl and heterocycloalkyl;

$R^b$, $R^{b'}$ and $R^{b''}$ are, independently, H, $C_{1-6}$ alkyl, $C_{1-6}$ alkoxy, $C_{1-6}$ haloalkyl, $C_{2-6}$ alkenyl, $C_{2-6}$alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, amino, halo, $C_{1-6}$alkyl, $C_{1-6}$haloalkyl, aryl, arylalkyl, heteroaryl, heteroarylalkyl, cycloalkyl and heterocycloalkyl;

$R^C$ and $R^d$ are, independently, H, $C_{1-10}$ alkyl, $C_{1-6}$ alkoxy, $C_{1-6}$ haloalkyl, $C_{2-6}$ alkenyl, $C_{2-6}$alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, amino, halo, $C_{1-6}$alkyl, $C_{1-6}$haloalkyl, aryl, arylalkyl, heteroaryl, heteroarylalkyl, cycloalkyl and heterocycloalkyl;

or $R^C$ and $R^d$ together with the N atom to which they are attached form a 4-, 5-, 6- or 7-membered heterocycloalkyl group optionally substituted with 1, 2, or 3 substituents independently selected from OH, amino, halo, $C_{1-6}$alkyl, $C_{1-6}$ haloalkyl, aryl, arylalkyl, heteroaryl, heteroarylalkyl, cycloalkyl and heterocycloalkyl;

$R^c$, and $R^{d'}$ are, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

or $R^{C'}$ and $R^{d'}$ together with the N atom to which they are attached form a 4-, 5-, 6- or 7-membered heterocycloalkyl group optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

$R^{C''}$ and $R^{d''}$ are, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

or $R^{C''}$ and $R^{d''}$ together with the N atom to which they are attached form a 4-, 5-, 6- or 7-membered heterocycloalkyl group optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

m is 0, 1, or 2;
n is 1;
p is 0 or 1; and
q is 0, 1, 2, or 3.

2. A compound of Formula I:

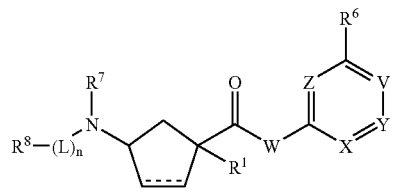

or pharmaceutically acceptable salt thereof, wherein:
a dashed line indicates an optional bond;
W is:

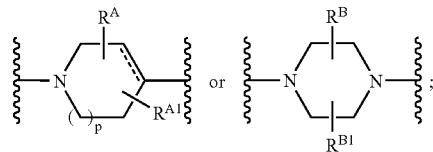

V is N, NO or $CR^5$;
X is N, NO or $CR^2$;
Y is N, NO or $CR^3$;
Z is N, NO or $CR^4$; wherein no more than one of V, X, Y and Z is NO;
L is $C_{1-4}$ alkylenyl, $C_{2-4}$ alkenylenyl, $C_{2-4}$ alkynylenyl, C(O), C(O)$NR^9$, S(O), S($O_2$)$NR^9$, S(O)$_2$, or S(O)$_2NR^9$;
$R^A$, $R^{A1}$, $R^B$ and $R^{B1}$ are each, independently, H, OH, halo, $C_{1-6}$alkyl, $C_{1-6}$alkenyl, $C_{2-6}$alkynyl, $C_{1-6}$haloalkyl, $C_{1-6}$alkoxy, $C_{1-6}$haloalkoxy, heterocyclyl, carbocyclyl, $NR^{10}R^{12}$, $NR^{10}CO_2R^{11}$; $NR^{10}CONR^{10}R^{12}$, $NR^{10}SO_2NR^{10}R^{12}$, $NR^{10}$—$SO_2$—$R^{11}$, CN, $CONR^{10}R^{12}$, $CO_2R^{10}$, $NO_2$, $SR^{10}$, $SOR^{10}$, $SO_2R^{10}$, or $SO_2$—$NR^{10}R^{12}$;

$R^1$ is $C_{1-6}$ alkyl, $C_{1-6}$ haloalkyl, $C_{1-6}$ hydroxyalkyl, —($C_{0-6}$alkyl)-O—($C_{1-6}$ alkyl), —($C_{0-6}$alkyl)-S($C_{1-6}$ alkyl), —($C_{0-6}$alkyl)-($C_{3-7}$cycloalkyl)-($C_{0-6}$ alkyl), OH, $OR^{10}$, $SR^{10}$, $COR^{11}$, $CO_2R^{10}$, $CONR^{10}R^{12}$, carbocyclyl, heterocyclyl, CN, $NR^{10}R^{12}$, $NR^{10}SO_2R^{10}$, $NR^{10}COR^{10}$, $NR^{10}CO_2R^{10}$, $NR^{10}CONR^{12}$, $CR^{10}R^{11}CO_2R^{10}$ or $CR^{10}R^{11}OCOR^{10}$;

$R^2$, $R^3$, $R^4$, $R^5$ and $R^6$ are each, independently, H, OH, halo, $C_{1-6}$alkyl, $C_{1-6}$haloalkyl, $C_{1-6}$alkoxy, $C_{1-6}$ haloalkoxy, $C_{1-6}$ thioalkoxy, $NR^{10}R^{12}$, $NR^{10}CO_2R^{11}$, $NR^{10}CONR^{10}R^{12}$, $NR^{10}SO_2NR^{10}R^{12}$, $NR^{10}$—$SO_2$—$R^{11}$, heterocyclyl, carbocyclyl, carbocyclyloxy, heterocyclyloxy, CN, $NO_2$, $COR^{11}$, $CONR^{10}R^{12}$, $CO_2R^{10}$, $NO_2$, $SR^{10}$, $SO_2R^{10}$, $SO_2R^{10}$; or $SO_2$—$NR^{10}R^{12}$;

$R^7$ is H or $C_{1-8}$ alkyl optionally substituted by 1, 2, 3, 4, 5 or 6 substituents independently selected from halo, $C_{1-10}$ haloalkyl, Cy, CN, $NO_2$, $OR^a$, C(O)$R^b$, C(O)$NR^cR^d$, C(O)$OR^a$, OC(O)$R^b$, OC(O)$NR^cR^d$, $NR^cR^d$, $NR^c$C(O)

$R^b$, $NR^cC(O)NR^d NR^cC(O)OR^a$, $S(O)R^b$, $S(O)NR^cR^d$, $S(O)_2R^b$, $NR^cS(O)_2R^b$, and $S(O)_2NR^cR^d$;

$R^8$ is $C_{1-10}$ alkyl, $C_{2-10}$ alkenyl, $C_{2-10}$ alkynyl, $C_{1-10}$ haloalkyl, aryl, cycloalkyl, heteroaryl, or heterocycloalkyl, wherein said $C_{1-10}$ alkyl, $C_{2-10}$ alkenyl, $C_{2-10}$ alkynyl, $C_{1-10}$ haloalkyl, aryl, cycloalkyl, heteroaryl, or heterocycloalkyl is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, Cy', —($C_{1-4}$ alkyl)-Cy', CN, $NO_2$, —$(CH_2)_q$—$OR^{a'}$, —$(CH_2)_q$—$SR^{a'}$, —$(CH_2)_q$—$C(O)R^{b'}$, —$(CH_2)_q$-$C(O)NR^{c'}R^{d'}$, —$(CH_2)_q$ $C(O)OR^{a'}$, —$(CH_2)_q OC(O)R^{b'}$, —$(CH_2)_q$—$OC(O)NR^{c'}R^{d'}$, —$(CH_2)_q$—$NR^{c'}R^{d'}$, —$(CH_2)_q$—$NR^{c'}C(O)OR^{a'}$, —$(CH_2)_q OC(O)R^{b'}$, —$(CH_2)_q$—$NR^{c'}C(O)OR^{a'}$, —$(CH_2)_q$—$S(O)R^{b'}$, —$(CH_2)_q$—$S(O)NR^{c'}R^{d'}$, —$(CH_2)_q$—$S(O)_2R^{b'}$, —$(CH_2)_q NR^{c'}S(O)_2R^b$, and —$(CH_2)_g S(O)_2 NR^{c'}R^{d'}$;

Cy and Cy' are, independently, aryl, heteroaryl, cycloalkyl, or heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{b''}$, $NR^{c''}C(O)OR^{a''}$, $S(O)R^{b''}$, $S(O)NR^{c''}R^{d''}$, $S(O)_2 R^{b''}$, and $S(O)_2 NR^{c''}R^{d''}$;

$R^9$ is H, $C_{1-10}$ alkyl, $C_{1-6}$ haloalkyl, $C_{2-6}$ alkenyl, or $C_{2-6}$ alkynyl, wherein said $C_{1-10}$ alkyl, $C_{1-6}$ haloalkyl, $C_{2-6}$ alkenyl, or $C_{2-6}$ alkynyl is optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

$R^{10}$ is H, $C_{1-6}$ alkyl, benzyl, phenyl, or $C_{3-6}$ cycloalkyl, wherein said $C_{1-6}$ alkyl, benzyl, phenyl, or $C_{3-6}$ cycloalkyl is optionally substituted with 1, 2, or 3 substituents independently selected from halo, OH, $C_{1-3}$alkyl, $C_{1-3}$haloalkyl, $C_{1-3}$alkoxy, $C_{1-3}$haloalkoxy, $CO_2H$, and $CO_2$—($C_{1-6}$alkyl);

$R^{11}$ is H, OH, $C_{1-6}$ alkyl, $C_{1-6}$ alkoxy, benzyl, phenyl, benzyloxy, phenyloxy, $C_{3-6}$ cycloalkyl or $C_{3-6}$ cycloalkyloxy, wherein said $C_{1-6}$ alkyl, $C_{1-6}$ alkoxy, benzyl, phenyl, benzyloxy, phenyloxy, $C_{3-6}$cycloalkyl or $C_{3-6}$ cycloalkyloxy, is optionally substituted with 1, 2 or 3 substituents independently selected from halo, OH, $C_{1-3}$ alkyl, $C_{1-3}$ alkoxy, COY, $CO_2$—($C_{1-6}$ alkyl) and $CF_3$;

$R^{12}$ is H, $C_{1-6}$ alkyl, benzyl, phenyl, or $C_{3-6}$ cycloalkyl, wherein said $C_{1-6}$ alkyl, benzyl, phenyl, or $C_{3-6}$ cycloalkyl is optionally substituted with 1, 2, or 3 substituents independently selected from halo, OH, $C_{1-3}$ alkyl, $C_{1-3}$ haloalkyl, $C_{1-3}$ alkoxy, $C_{1-3}$ haloalkoxy, $CO_2H$, and $CO_2$—($C_{1-6}$alkyl);

$R^a$, $R^{a'}$ and $R^{a''}$ are, independently, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, amino, halo, $C_{1-6}$ alkyl, aryl, arylalkyl, heteroaryl, heteroarylalkyl, cycloalkyl and heterocycloalkyl;

$R^b$, $R^{b'}$, and $R^{b''}$ are, independently, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

$R^c$ and $R^d$ are, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

or $R^c$ and $R^d$ together with the N atom to which they are attached form a 4-, 5-, 6- or 7-membered heterocycloalkyl group optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

$R^{c'}$ and $R^{d'}$ are, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

or $R^{c'}$ and $R^{d'}$ together with the N atom to which they are attached form a 4-, 5-, 6- or 7-membered heterocycloalkyl group optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

$R^{c''}$ and $R^{d''}$ are, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

or $R^{c''}$ and $R^{d''}$ together with the N atom to which they are attached form a 4-, 5-, 6- or 7-membered heterocycloalkyl group optionally substituted with 1, 2, or 3 substituents independently selected from OH, amino, halo, $C_{1-6}$ alkyl, $C_{1-6}$ haloalkyl, aryl, arylalkyl, heteroaryl, heteroarylalkyl, cycloalkyl and heterocycloalkyl;

n is 0 or 1;

p is 0 or 1; and q is 0, 1, 2, or 3;

wherein when n is 0, $R^8$ is other than substituted or unsubstituted tetrahydropyran-4-yl.

3. The compound of claim 1 wherein W is

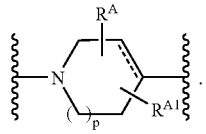

4. The compound of claim 1 wherein W is

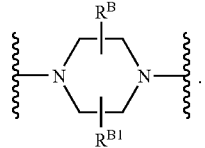

5. The compound of claim 1 wherein V is $CR^5$.
6. The compound of claim 1 wherein X is $CR^2$.
7. The compound of claim 1 wherein Y is $CR^3$.
8. The compound of claim 1 wherein Z is $CR^4$.
9. The compound of claim 1 wherein X is $CR^2$; Y is $CR^3$; and Z is $CR^4$.
10. The compound of claim 1 wherein V is $CR^5$; X is $CR^2$; Y is $CR^3$; and Z is $CR^4$.
11. The compound of claim 1 wherein $R^A$, $R^{A1}$, $R^B$ and $R^{B1}$ are each, independently H, OH, halo, $C_{1-6}$alkyl, $C_{2-6}$alkenyl, $C_{2-6}$alkynyl, $C_{1-6}$haloalkyl, $C_{1-6}$alkoxy or $C_{1-6}$haloalkoxy.
12. The compound of claim 1 wherein $R^A$, $R^{A1}$, $R^B$ and $R^{B1}$ are each, independently H, OH, halo, or $C_{1-6}$alkoxy.
13. The compound of claim 1 wherein $R^A$, $R^{A1}$, $R^B$ and $R^{B1}$ are each, independently H or OH.
14. The compound of claim 1 wherein $R^1$ is $C_{1-6}$alkyl, $C_{1-6}$hydroxyalkyl, —($C_{0-6}$alkyl)-O—($C_{1-6}$allyl), or heterocyclyl.
15. The compound of claim 1 wherein $R^1$ is $C_{1-6}$alkyl.
16. The compound of claim 1 wherein $R^1$ is prop-2-yl.
17. The compound of claim 1 wherein one of $R^5$ and $R^6$ is other than H.
18. The compound of claim 1 wherein one of $R^5$ and $R^6$ is $C_{1-4}$haloalkyl.
19. The compound of claim 1 wherein $R^6$ is $C_{1-4}$haloalkyl.
20. The compound of claim 1 wherein $R^6$ is $CF_3$.
21. The compound of claim 1 wherein $R^7$ is H.
22. The compound of claim 1 wherein $R^1$ is $C_{1-8}$alkyl.
23. The compound of claim 1 wherein $R^8$ is $C_{1-10}$alkyl, aryl, cycloalkyl, heteroaryl, or heterocycloalkyl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, Cy', —($C_{1-4}$alkyl)-Cy', CN, $NO_2$, —$(CH_2)_q$—$OR^{a'}$, —$(CH_2)_q$—$SR^{a'}$, —$(CH_2)_q$—$C(O)R^{b'}$, —$(CH_2)_q$—$C(O)NR^{c'}R^{d'}$, —$(CH_2)_q$—$C(O)OR^{a'}$, —$(CH_2)_q$—$OC(O)R^{b'}$, —$(CH_2)_q$—$OC(O)NR^{c'}R^{d'}$, —$(CH_2)_q$—$NR^{c'}R^{d'}$, —$(CH_2)_q$—$NR^{c'}C(O)R^{b'}$, —$(CH_2)_q$—$NR^{c'}C(O)NR^{c'}R^{d'}$, —$(CH_2)_q$—$NR^{c'}C(O)OR^{a'}$, —$(CH_2)_q$—$S(O)R^{b'}$, —$(CH_2)_q$—$S(O)NR^{c'}R^{d'}$, —$(CH_2)_q$—$S(O)_2R^{b'}$, —$(CH_2)_q$—$NR^{c'}S(O)_2R^{b'}$, and —$(CH_2)_q$—$S(O)_2NR^{c'}R^{d'}$.

24. The compound of claim 1 wherein $R^8$ is $C_{1-10}$ alkyl optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$haloalkyl, $C_{1-4}$ hydroxyalkyl, $C_4$ cyanoalkyl, Cy', —($C_{1-4}$ alkyl)-Cy', CN, $NO_2$, —$(CH_2)_q$—$OR^2$, $(CH_2)_q)SR^{a'}$, —$(CH_2)_q$—$C(O)R^{b'}$, —$(CH_2)_q$—$C(O)NR^{c'}R^{b'}$, —$(CH_2)_q$—$C(O)OR^{a'}$, —$(CH_2)_q$—$OC(O)R^{b'}$, —$(CH_2)_q$—$OC(O)NR^{c'}R^{d'}$, —$(CH_2)_q$—$NR^{c'}R^{d'}$, —$(CH_2)_q$—$NR^{c'}C(O)R^{b'}$, —$(CH_2)_q$—$NR^{c'}C(O)NR^{c'}R^{d'}$, —$(CH_2)_q$—$NRC^{c'}(O)OR^{a'}$, —$(CH_2)_q$—$S(O)R^{b'}$, —$(CH_2)_q$—$S(O)NR^{c'}R^{d'}$, —$(CH_2)_q$—$S(O)_2R^{b'}$, —$(CH_2)_q$—$NR^{c'}S(O)_2R^{b'}$, and —$(CH_2)_q$—$S(O)_2NR^{c'}R^{d'}$.

25. The compound of claim 1 wherein $R^8$ is aryl or heteroaryl, each optionally substituted with 1, 2, 3, 4, 5, or 6 substituents independently selected from halo, $C_{1-4}$ alkyl, $C_{2-4}$ alkenyl, $C_{2-4}$alkynyl, $C_{1-4}$ haloalkyl, $C_{1-4}$ hydroxyalkyl, $C_{1-4}$ cyanoalkyl, Cy', —($C_{1-4}$alkyl)-Cy', CN, $NO_2$, —$(CH_2)_q$—$OR^{a'}$, —$(CH_2)_q$$SR^{a'}$, —$(CH_2)_q$—$C(O)R^{b'}$, —$(CH_2)_q$—$C(O)NR^{c'}R^{d'}$, —$(CH_2)_q$—$C(O)OR^{a'}$, —$(CH_2)_q$—$OC(O)R^{b'}$, —$(CH_2)_q$—$OC(O)NR^{c'}R^{d'}$, —$(CH_2)_q$—$NR^{c'}R^{d'}$, —$(CH_2)_q$—$NR^{c'}C(O)R^{b'}$, —$(CH_2)_q$ q-$NR^{c'}$ $C(O)NR^{c'}R^{d'}$, —$(CH_2)_q$—$NR^{c'}C(O)OR^{a'}$, —$(CH_2)_q$—$S(O)R^{b'}$, —$(CH_2)_q$—$S(O)NR^{c'}R^{d'}$, —$(CH_2)_q$—$S(O)_2R^{b'}$, —$(CH_2)_q$—$NR^{c'}$ $S(O)_2R^{b'}$, and (—$(CH_2)_q$—$S(O)_2NR^{C'}R^{d'}$.

26. The compound of claim 1 wherein $R^8$ is cycloalkyl or heterocycloalkyl, each optionally substituted with 1, 2, 3, 4, 5, or 6 substituents independently selected from halo, $C_{1-4}$ alkyl, $C_{2-4}$alkenyl, $C_{2-4}$ alkynyl, $C_{1-4}$ haloalkyl, $C_{1-4}$ hydroxyalkyl, $C_{1-4}$ cyanoalkyl, Cy', —($C_{1-4}$alkyl)-Cy', CN, $NO_2$, —$(CH_2)_q$—$OR^{a'}$, —$(CH_2)_q$—$SR^{a'}$, —$(CH_2)_q$—$C(O)R^{b'}$, —$(CH_2)_q$—$C(O)NR^{c'}R^{d'}$, —$(CH_2)_q$—$C(O)OR^{a'}$, —$(CH_2)_q$—$OC(O)R^{b'}$, —$(CH_2)_q$—$OC(O)NR^{c'}R'$, —$(CH_2)_q$—$NR^{c'}R^{d'}$, —$(CH_2)_q$—$NR^{c'}C(O)R^{b'}$, —$(CH_2)_q$—$NR^{c'}C(O)NR^{c'}R^{d'}$, —$(CH_2)_q$—$NR^{c'}C(O)OR^{a'}$, —$(CH_2)_q$—$S(O)R^{b'}$, —$(CH_2)_q$—$S(O)NR^{c'}R^{d'}$, —$(CH_2)_q$—$S(O)_2R^{b'}$, —$(CH_2)_q$—$NR^{c'}S(O)_2 R^{b'}$, and —$(CH_2)_q$—$(O)_2NR^{c'}R^{d'}$.

27. The compound of claim 1 wherein $R^8$ is phenyl optionally substituted with 1, 2, 3, 4, 5, or 6 substituents independently selected from halo, $C_{1-4}$ alkyl, $C_{2-4}$alkenyl, $C_{2-4}$ alkynyl, $C_{1-4}$ haloalkyl, $C_{1-4}$ hydroxyalkyl, $C_{1-4}$ cyanoalkyl, Cy', —($C_{1-4}$alkyl)-Cy', CN, $NO_2$, —$(CH_2)_q$—$OR^{a'}$, —$(CH_2)_q$—$SR^{a'}$, —$(CH_2)_q$—$C(O)R^{b'}$, —$(CH_2)_q$—$C(O)NR^{c'}R^{d'}$, —$(CH_2)_q$—$C(O)OR^{a'}$, —$(CH_2)_q$—$OC(O)R^{b'}$, —$(CH_2)_q$—$C(O)NR^{c'}R'$, —$(CH_2)_q$—$NR^{c'}R^{d'}$, —$(CH_2)_q NR^{c'}C(O)R^{b'}$, —$(CH_2)_q$—$NR^{c'}C(O)NR^{c'}R^{d'}$, —$(CH_2)_q$—$NR^{c'}C(O)OR^{a'}$, —$(CH_2)_q$—$S(O)R^{b'}$, —$(CH_2)_q$—$S(O)NR^{c'}R^{d'}$, —$(CH_2)_q$—$S(O)_2R^{b'}$, —$(CH_2)_q$—$NR^{c'}S(O)_2R^{b'}$, and —$(CH_2)_q$—$S(O)_2NR^{c'}R^{d'}$.

28. The compound of claim 1 wherein n is 0 and $R^8$ is $C_{1-8}$alkyl, substituted with 1, 2, or 3 substituents independently selected from OH, halo, and —$(CH_2)_q$—$C(O)R^{b'}$.

29. The compound of claim 1 wherein n is 1, L is $C_{1-4}$alkylenyl, and $R^8$ is aryl or heteroaryl each optionally substituted with 1, 2, or 3 substituents selected from halo, $C_{1-4}$alkyl, $C_{1-4}$haloalkyl, $OR^{a'}$, and —$(CH_2)_q$—$C(O)R^{b'}$.

30. The compound of claim 1 wherein L is $C_{1-4}$alkylenyl.
31. The compound of claim 1 wherein L is methylene.
32. The compound of claim 1 wherein L is C(O) or $S(O)_2$.
33. The compound of claim 1 having Formula Ia:

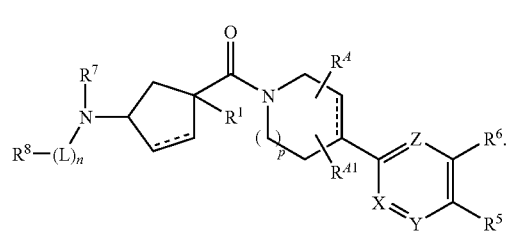

Ia

34. The compound of claim 1 having Formula Ib, Ic or Id:

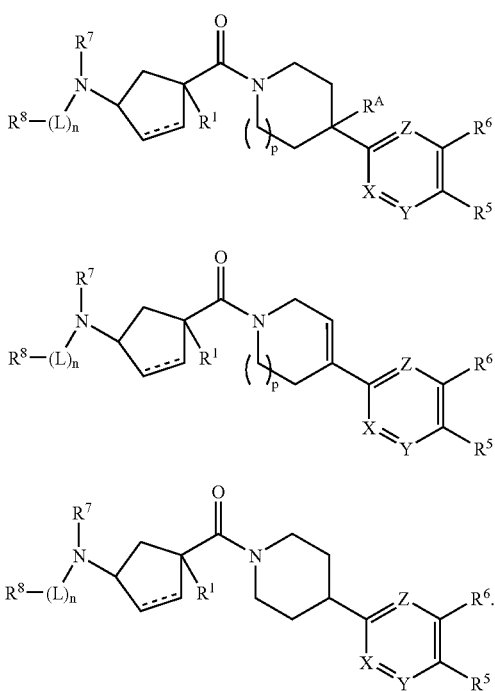

35. The compound of claim 1 having Formula Ie of If:

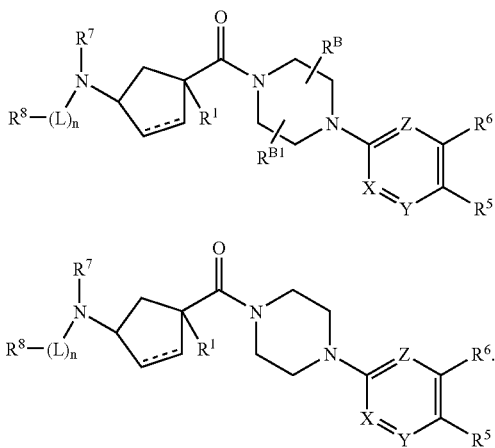

36. The compound of claim 1 having the Formula Ig:

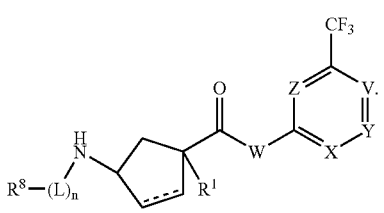

37. The compound of claim 1 selected from

4-{[(1R3S)-3-isopropyl-3-({4-[4-(trifluoromethyl)pyridin-2-yl]piperazin-1yl}carbonyl)cyclopentyl]amino}-1-(5-pyrimidin-2-yl pyridin-2-yl)cyclohexanol;

ethyl 4-{[(1R3S)-3-isopropyl-3-({4-[4-(trifluoromethyl)pyridin-2-yl]piperazin-1yl}carbonyl)cyclopentyl]amino}-3-methoxypiperidine-1-carboxylate;

methyl 4-{[1R3S)-3-isopropyl-3-({4-[4-(trifluoromethyl)pyridin-2-yl]piperazin-1yl}carbonyl)cyclopentyl]amino}-3-methoxypiperidine-1-carboxylate;

((1S,3R)-3-(3-oxa-bicyclo [3.3.1]nonan-9-ylamino)-1-isopropylcyclopentyl)(4-(4(trifluoromethyl)pyridin-2-yl)piperazin-1-yl)methanone;

(1R,3S)-N-[(5-chloro-2-thienyl)methyl]-3-isopropyl-3-({4-[4-(trifluoromethyl)pyridin-2-yl]piperazin-1yl}carbonyl)cyclopentanamine; (1R,3S)-3-isopropyl-N-[(1-pyridin-3-yl-1H-pyrrol-2-yl)methyl]-3-({4-[4-(trifluoromethyl)pyridin-2-yl]piperazin-1-yl}carbonyl)cyclopentanamine;

(1R,3S)-N-[(1-ethyl-1H-pyrazol-4-yl)methyl]-3-isopropyl-3-({4-[4-(trifluoromethyl)pyridin-2yl]piperazin-1-yl}carbonyl)cyclopentanamine; (1R,3S)-3-isopropyl-N-(quinolin-6-ylmethyl)-3-({4-[4-(trifluoromethyl)pyridin-2-yl]piperazin-1yl}carbonyl) cyclopentanamine;

7-({[(1R,3S)-3-isopropyl-3-({4-[4-(trifluoromethyl)pyridin-2-yl]piperazin-1yl}carbonyl)cyclopentyl]amino}methyl)-1H-pyrido[23-b][14]oxazin-2(3H)-one;

(1R,3S)-N-(24-dimethoxybenzyl)-3-isopropyl-3-({4-[4-(trifluoromethyl)pyridin-2-yl]piperazin-1yl}carbonyl) cyclopentanamine;

N-[(1R,3S)-3-isopropyl-3-({4-[4-(trifluoromethyl)pyridin-2-yl]piperazin-1-yl}carbonyl)cyclopentyl]-1pyrimidin-2-ylpiperidin-3-amine;

1-but-2-yn-1-yl-5-{[(1R,3S)-3-isopropyl-3-({4-[4-(trifluoromethyl)pyridin-2-yl]piperazin-1yl}carbonyl)cyclopentyl]amino}azepan-2-one;

N-isopropyl-3-(2-{[(1R,3S)-3-isopropyl-3-({4-[4-(trifluoromethyl)pyridin-2-yl]piperazin-1yl}carbonyl)cyclopentyl]amino}cyclopentyl)propanamide;

N-[(1R3S)-3-isopropyl-3-({4-[4-(trifluoromethyl)pyridin-2-yl]piperazin-1yl}carbonyl)cyclopentyl]indan-2-amine;

N-[(1R,3S)-3-isopropyl-3-({4-[4-(trifluoromethyl)pyridin-2-yl]piperazin-1yl}carbonyl)cyclopentyl]tetrahydro-2H-thiopyran-4-amine 11-dioxide;

(1R,3S)-N-cyclopentyl-3-isopropyl-3-({4-[4-(trifluoromethyl)pyridin-2-yl]piperazin-1yl}carbonyl)cyclopentanamine;

3-(2-{[(1R,3S)-3-isopropyl-3-({4-[4-(trifluoromethyl)pyridin-2-yl]piperazin-1yl}carbonyl)cyclopentyl]amino}cyclopentyl)-N-propylpropanamide;

6,8-difluoro-N-[(1R,3S)-3-isopropyl-3-({4-[4-(trifluoromethyl)pyridin-2-yl]piperazin-1yl}carbonyl)cyclopentyl]-1234-tetrahydronaphthalen-2-amine;

N-[(1R,3S)-3-isopropyl-3-({4-[4-(trifluoromethyl)pyridin-2-yl]piperazin-1-yl}carbonyl)cyclopentyl]1234-tetrahydronaphthalen-2-amine;

2,5-anhydro-1,3,4-trideoxy-3-{[(1R,3S)-3-isopropyl-3-({4-[4-(trifluoromethyl)pyridin-2-yl]piperazin-1yl}carbonyl)cyclopentyl]amino}pentitol;

N-[(1R,3S)-3-isopropyl-3-({4-[4-(trifluoromethyl)pyridin-2-yl]piperazin-1-yl}carbonyl)cyclopentyl]-35-dimethyltetrahydro-2H-pyran-4-amine;

(1R,3S)-3-isopropyl-N-[1-methyl-3-(1H-pyrazol-1-yl)propyl]-3-({4-[4-(trifluoromethyl)pyridin-2yl]piperazin-1yl}carbonyl)cyclopentanamine;

N-[(1R,3S)-3-isopropyl-3-({-[4-(trifluoromethyl)pyridin-2-yl]piperazin-1yl}carbonyl)cyclopentyl]tetrahydrofuran-3-amine;

N-[(1R,3S)-3-isopropyl-3-({4-[4-(trifluoromethyl)pyridin-2-yl]piperazin-1-yl}carbonyl)cyclopentyl]-N-methyltetrahyclrofuran-3-amine;

(1R,3S)-N-(34-dimethoxybenzyl)-3-isopropyl-3-({4-[4-(trifluoromethyl)pyridin-2-yl]piperazin-1yl}carbonyl)cyclopentanamine;

(1R,3S)-N-(1H-indol-5-ylmethyl)-3-isopropyl-3-({4-[4-(trifluoromethyl)pyridin-2-yl]piperazin-1yl}carbonyl)cyclopentanamine;

4-({[(1R,3S)-3-isopropyl-3-({4-[4-(trifluoromethyl)pyridin-2-yl]piperazin-1yl}carbonyl)cyclopentyl]amino}methyl)phenol;

(1R,3S)-N-(4-fluorobenzyl)-3-isopropyl-3-({4-[4-(trifluoromethyl)pyridin-2-yl]piperazin-1yl}carbonyl)cyclopentanamine;

5-({[(1R,3S)-3-isopropyl-3-({4-[4-(trifluoromethyl)pyridin-2-yl]piperazin-1yl}carbonyl)cyclopentyl]amino}methyl)-2-methoxyphenol;

6-({[(1R,3S)-3-isopropyl-3-({4-[4-(trifluoromethyl)pyridin-2-yl]piperazin-1yl}carbonyl)cyclopentyl]amino}methyl)-2H-[4-benzoxazin-3(4H)-one;

(1R,3S)-3-isopropyl-N-(3'-methoxy-4-methylbenzyl)-3-({-[4-(trifluoromethyl)pyridin-2-yl]piperazin-1-yl}carbonyl)cyclopentanamine;

((1S,3R)-3-(benzylamino)-1-isopropylcyclopentyl)(4-(4-(trifluoromethyl)pyridin-2-yl)piperazin-1yl)methanone;

((1S,3R)-3-(4-chlorobenzylamina)-1-isopropylcyclopentyl)(4-(4-(trifluoromethyl)pyridin-2yl) piperazin-1-yl)methanone;

((1S,3R)-3-(4-methoxybenzylamina)-1-isopropylcyclopentyl)(4-(4-(trifluoromethyl)pyridin-2yl) piperazin-1-yl)methanone;

((1S,3R)-3-(4-hydroxy-3-methylbutan-2-ylamina)-1-isopropylcyclopentyl)(4-(4(trifluoromethyl)pyridin-2-yl)piperazin-1-yl)methanone;

((1S,3R)-3-(4-hydroxy-4-methylpentan-2-ylamino)-1-isopropylcyclopentyl)(4-(4(trifluoromethyl)pyridin-2-yl)-5,6-dihydropyridin-1(2H)-yl)methanone;

((1S,3R)-3-(2-(chloromethyl)-3-hydroxy-2-methyl propylamino)-1-isopropylcyclopentyl)(4-(4(trifluoromethyl)pyridin-2-yl)-5,6-dihydropyridin-1(2H)-yl)methanone;

((1S,3R)-1-isopropyl-3-((tetrahydro-2H-pyran-4-yl)methylamino)cyclopentyl)(4(4(trifluoromethyl)pyridin-2-yl)-5,6-dihydropyridin-1(2H)-yl)methanone;

((1S,3R)-1-isopropyl-3-(methyl(neopentyl)amina)cyclopentyl)(4-(4-(trifluoromethyl)pyridin-2yl)piperazin-1-yl)methanone;

N-((1R,3S)-3-isopropyl-3-(1-(4-(trifluoromethyl)pyridin-2-yl)piperazine-4carbonyl)cyclopentyl)benzenesulfonamide;

((1S,3R)-1-isopropyl-3-(1-phenylethylamino)cyclopentyl)(4-(4-(trifluoromethyl)pyridin-2yl)piperazin-1-yl)methanone;

((1S,3R)-1-isopropyl-3-(1-phenylpropylamino)cyclopentyl(4-(4-(trifluoromethyl)pyridin-2yl) piperazin-1-yl)methanone;

((1S,3R)-3-(diethylamina)-1-isopropylcyclopentyl)(4-(5-(trifluoromethyl)pyridin-3-yl)-5,6dihydropyridin-1(2H)-yl)methanone;

((1S,3R)-1-isopropyl-3-(1-(tetrahydro-2H-pyran-4-yl)ethylamino)cyclopentyl)(4-(4(trifluoromethyl)pyrimidin-2-yl)piperazin-1-yl)methanone;

((1S,3R)-1-isopropyl-3-((3-methoxy-tetrahydro-2H-pyran-4-yl)methylamina)cyclopentyl)(4-(6(trifluoromethyl)pyridin-2-yl)piperazin-1-yl)methanone;

((1S,3R)-3-(1,2-diphenylethylamino)-1-isopropylcyclopentyl)(4-(6-(trifluoromethyl)pyrimidin-4yl)piperazin-1-yl)methanone;

((1S,3R)-1-isopropyl-3-(phenethylamino)cyclopentyl)(4-(2-methyl-6-(trifluoromethyl)pyrimidin-4yl)piperazin-1-yl)methanone;

3-fluoro-N-((1R,3S)-3-isopropyl-3-(1(4-(trifluoromethyl)pyridin-2-yl)piperazine-4carbonyl)cyclopentyl)benzenesulfonamide; 3-((1R,3S)-3-(2-hydroxypropan-2-yl)-3-(1-(4(trifluoromethyl)pyridin-2-yl)piperazine-4-carbonyl)cyclopentylamino)-2,2-dimethylpropanoic acid;

((1S,3R)-1-isopropyl-3-(pyridin-3-ylmethylamina)cyclopentyl)(4-(4-(trifluoromethyl)pyridin-2-yl)piperazin-1-yl)methanone;

((1S,3R)-3-(3-hydroxypropylamino)-1-isopropylcyclopentyl)(4-(4-(trifluoromethyl)pyridin-2-yl)piperazin-1-yl)methanone;

((1S,3R)-3-(benzyl(isopropyl)amino)-1-isopropylcyclopentyl)(4-(4-(trifluoromethyl)pyridin-2-yl)piperazin-1-yl)methanone;

N-((1R,3S)-3-isopropyl-3-(1-(4-(trifluoromethyl)pyridin-2-yl)piperazine-4carbonyl)cyclopentyl)benzamide;

N-((1R,3S)-3-isopropyl-3-(1-(4-(trifluoromethyl)pyridin-2-yl)piperazine-4carbonyl)cyclopentyl)cyclohexanecarboxamide;

N-((1R,3S)-3-isopropyl-3-(1-(4-(trifluoromethyl)pyridin-2-yl)piperazine-4-carbonyl)cyclopentyl)-2(tetrahydro-2H-pyran-4-yl)acetamide;

((1S,3R)-1-isopropyl-3-{naphthalen-2-ylmethylamina}cyclopentyl)(4-(4-(trifluoromethyl)pyridin-2-yl)piperazin-1-yl)methanone;

((1S,3R)-3-(4-hydroxy-4-(thiazol-2-yl)cyclohexylamino)-1-isopropylcyclopentyl)(4-(4(trifluoromethyl)pyridin-2-yl)piperazin-1-yl)methanone;

((1S,3R)-3-(4-phenoxybenzylamino)-1-isopropylcyclopentyl)(4-(4-(trifluoromethyl)pyridin-2-yl)piperazin-1-yl)methanone;

((1S,3R)-3-(3,4-dimethoxybenzylamino)-1-isopropylcyclopentyl)(4-(4-(trifluoromethyl)pyridin-2-yl)piperazin-1-yl)methanone;

((1S,3R)-3-(3,5-bis(trifluoromethyl)benzylamina)-1-isopropylcyclopentyl)(4-(4-(trifluoromethyl) pyridin-2-yl) piperazin-1-yl)methanone;

N-((1R,3S)-3-isopropyl-3-(1-(4-(trifluoromethyl)pyridin-2-yl)piperazine-4carbonyl)cyclopentyl)methanesulfonamide;

N-((1R,3S)-3-isopropyl-3-(1-(4-(trifluoromethyl)pyridin-2-yl)piperazine-4-carbonyl)cyclopentyl)-4(trifluoromethyl)benzenesulfonamide; or ((1S,3R)-1-isopropyl-3-(neopentylamino)cyclopentyl)(4-(4-(trifluoromethyl)pyridin-2-yl)piperazin-1yl)methanone.

38. A composition comprising a compound of claim 1, or a pharmaceutically acceptable salt thereof, and a pharmaceutically acceptable carrier.

\* \* \* \* \*